(12) United States Patent
Gillies et al.

(10) Patent No.: US 7,601,814 B2
(45) Date of Patent: Oct. 13, 2009

(54) REDUCING THE IMMUNOGENICITY OF FUSION PROTEINS

(75) Inventors: Stephen D. Gillies, Carlisle, MA (US); Jeffrey Way, Cambridge, MA (US); Anita A. Hamilton, Aberdeen (GB)

(73) Assignee: Merck Patent GmbH, Darmstadt (DE)

( * ) Notice: Subject to any disclaimer, the term of this patent is extended or adjusted under 35 U.S.C. 154(b) by 233 days.

(21) Appl. No.: 11/233,683

(22) Filed: Sep. 23, 2005

(65) Prior Publication Data

US 2006/0025573 A1 Feb. 2, 2006

Related U.S. Application Data

(62) Division of application No. 10/112,582, filed on Mar. 29, 2002, now Pat. No. 6,992,174.

(60) Provisional application No. 60/280,625, filed on Mar. 30, 2001.

(51) Int. Cl.
*C12P 21/08* (2006.01)

(52) U.S. Cl. .............. 530/387.3; 424/134.1; 424/178.1; 424/185.1; 424/192.1; 530/350; 530/388.1

(58) Field of Classification Search ........................ None
See application file for complete search history.

(56) References Cited

U.S. PATENT DOCUMENTS

| | | |
|---|---|---|
| 4,196,265 A | 4/1980 | Koprowski et al. |
| 4,469,797 A | 9/1984 | Albarella |
| 4,522,811 A | 6/1985 | Eppstein et al. |
| 4,667,016 A | 5/1987 | Lai et al. |
| 4,676,980 A | 6/1987 | Segal et al. |
| 4,703,008 A | 10/1987 | Lin |
| 4,732,683 A | 3/1988 | Georgiades et al. |
| 4,737,462 A | 4/1988 | Mark et al. |
| 4,816,567 A | 3/1989 | Cabilly et al. |
| 4,946,778 A | 8/1990 | Ladner et al. |
| 4,975,369 A | 12/1990 | Beavers et al. |
| 5,019,368 A | 5/1991 | Epstein et al. |
| 5,073,627 A | 12/1991 | Curtis et al. |
| 5,082,658 A | 1/1992 | Palladino |
| 5,091,513 A | 2/1992 | Huston et al. |
| 5,114,711 A | 5/1992 | Bell et al. |
| 5,116,964 A | 5/1992 | Capon et al. |
| 5,199,942 A | 4/1993 | Gillis |
| 5,225,538 A | 7/1993 | Capon et al. |
| 5,225,539 A | 7/1993 | Winter |
| 5,258,498 A | 11/1993 | Huston et al. |
| 5,314,995 A | 5/1994 | Fell, Jr. et al. |
| 5,349,053 A | 9/1994 | Landolfi |
| 5,359,035 A | 10/1994 | Habermann |
| 5,399,346 A | 3/1995 | Anderson et al. |
| 5,428,130 A | 6/1995 | Capon et al. |
| 5,441,868 A | 8/1995 | Lin |
| 5,457,038 A | 10/1995 | Trinchieri et al. |
| 5,480,981 A | 1/1996 | Goodwin et al. |
| 5,514,582 A | 5/1996 | Capon et al. |
| 5,538,866 A | 7/1996 | Israeli et al. |
| 5,541,087 A | 7/1996 | Lo et al. |
| 5,543,297 A | 8/1996 | Cromlish et al. |
| 5,547,933 A | 8/1996 | Lin |
| 5,552,524 A | 9/1996 | Basinski et al. |
| 5,585,089 A | 12/1996 | Queen et al. |
| 5,589,466 A | 12/1996 | Felgner et al. |
| 5,601,819 A | 2/1997 | Wong et al. |
| 5,609,846 A | 3/1997 | Goldenberg |
| 5,614,184 A | 3/1997 | Sytkowski et al. |
| 5,618,698 A | 4/1997 | Lin |
| 5,624,821 A | 4/1997 | Winter et al. |
| 5,639,725 A | 6/1997 | O'Reilly et al. |
| 5,645,835 A | 7/1997 | Fell, Jr. et al. |
| 5,650,150 A | 7/1997 | Gillies |
| 5,650,492 A | 7/1997 | Gately et al. |
| 5,667,776 A | 9/1997 | Zimmerman et al. |
| 5,679,543 A | 10/1997 | Lawlis |
| 5,688,679 A | 11/1997 | Powell |
| 5,691,309 A | 11/1997 | Basinski et al. |
| 5,709,859 A | 1/1998 | Aruffo et al. |
| 5,712,120 A | 1/1998 | Rodriguez et al. |
| 5,719,266 A | 2/1998 | DiMarchi et al. |
| 5,723,125 A | 3/1998 | Chang et al. |
| 5,726,044 A | 3/1998 | Lo et al. |

(Continued)

FOREIGN PATENT DOCUMENTS

AU         21725/88         3/1989

(Continued)

OTHER PUBLICATIONS

Patel et al., Curr Hypertens Rep, 2008, 10:131-137, abstract only, 2 pages.*

(Continued)

*Primary Examiner*—Michael Szperka
(74) *Attorney, Agent, or Firm*—Goodwin Procter, LLP

(57) ABSTRACT

Disclosed are compositions and methods for producing fusion proteins with reduced immunogenicity. Fusion proteins of the invention include a junction region having an amino acid change that reduces the ability of a junctional epitope to bind to MHC Class II, thereby reducing its interaction with a T-cell receptor. Methods of the invention involve analyzing, changing, or modifying one or more amino acids in the junction region of a fusion protein in order to identify a T-cell epitope and reduce its ability to interact with a T cell receptor. Compositions and methods of the invention are useful in therapy.

7 Claims, No Drawings

U.S. PATENT DOCUMENTS

| | | |
|---|---|---|
| 5,728,552 A | 3/1998 | Fujisawa et al. |
| 5,733,876 A | 3/1998 | O'Reilly et al. |
| 5,738,852 A | 4/1998 | Robinson et al. |
| 5,756,349 A | 5/1998 | Lin |
| 5,756,461 A | 5/1998 | Stephens |
| 5,759,551 A | 6/1998 | Ladd et al. |
| 5,770,195 A | 6/1998 | Hudziak et al. |
| 5,795,779 A | 8/1998 | McCormick |
| 5,800,810 A | 9/1998 | Doyle et al. |
| 5,807,715 A | 9/1998 | Morrison et al. |
| 5,827,516 A | 10/1998 | Urban et al. |
| 5,827,703 A | 10/1998 | Debs et al. |
| 5,837,682 A | 11/1998 | Folkman et al. |
| 5,837,821 A | 11/1998 | Wu et al. |
| 5,843,423 A | 12/1998 | Lyman et al. |
| 5,854,205 A | 12/1998 | O'Reilly et al. |
| 5,856,298 A | 1/1999 | Strickland |
| 5,858,347 A | 1/1999 | Bauer et al. |
| 5,885,795 A | 3/1999 | O'Reilly et al. |
| 5,886,178 A | 3/1999 | Allen et al. |
| 5,888,772 A | 3/1999 | Okasinski et al. |
| 5,888,773 A | 3/1999 | Jost et al. |
| 5,891,680 A | 4/1999 | Lieschke et al. |
| 5,908,626 A | 6/1999 | Chang et al. |
| 5,922,685 A | 7/1999 | Rakhmilevich et al. |
| 5,955,422 A | 9/1999 | Lin |
| 5,994,104 A | 11/1999 | Anderson et al. |
| 5,994,126 A | 11/1999 | Steinman et al. |
| 6,080,409 A | 6/2000 | Laus et al. |
| 6,086,875 A | 7/2000 | Blumberg et al. |
| 6,100,387 A | 8/2000 | Herrmann et al. |
| 6,169,070 B1 | 1/2001 | Chen et al. |
| 6,171,588 B1 | 1/2001 | Carron et al. |
| 6,231,536 B1 | 5/2001 | Lentz |
| 6,277,375 B1 | 8/2001 | Ward |
| 6,281,010 B1 | 8/2001 | Gao et al. |
| 6,284,536 B1 | 9/2001 | Morrison et al. |
| 6,291,158 B1 | 9/2001 | Winter et al. |
| 6,335,176 B1 | 1/2002 | Inglese et al. |
| 6,340,742 B1 | 1/2002 | Burg et al. |
| 6,348,192 B1 | 2/2002 | Chan et al. |
| 6,406,689 B1 | 6/2002 | Falkenberg et al. |
| 6,429,199 B1 | 8/2002 | Krieg et al. |
| 6,444,792 B1 | 9/2002 | Gray et al. |
| 6,475,717 B1 | 11/2002 | Enssle et al. |
| 6,485,726 B1 | 11/2002 | Blumberg et al. |
| 6,500,641 B1 | 12/2002 | Chen et al. |
| 6,506,405 B1 | 1/2003 | Desai et al. |
| 6,551,592 B2 | 4/2003 | Lindhofer et al. |
| 6,583,272 B1 | 6/2003 | Bailon |
| 6,586,398 B1 | 7/2003 | Kinstler et al. |
| 6,617,135 B1 | 9/2003 | Gillies et al. |
| 6,627,615 B1 | 9/2003 | Debs et al. |
| 6,646,113 B1 | 11/2003 | Dreyfuss et al. |
| 6,838,260 B2 | 1/2005 | Gillies et al. |
| 6,946,134 B1 * | 9/2005 | Rosen et al. ............. 424/192.1 |
| 6,969,517 B2 | 11/2005 | Gillies et al. |
| 6,992,174 B2 | 1/2006 | Gillies et al. |
| 7,067,110 B1 | 6/2006 | Gillies et al. |
| 7,091,321 B2 | 8/2006 | Gillies et al. |
| 7,141,651 B2 | 11/2006 | Gillies et al. |
| 7,148,321 B2 | 12/2006 | Gillies et al. |
| 7,169,904 B2 | 1/2007 | Gillies et al. |
| 7,186,804 B2 | 3/2007 | Gillies et al. |
| 7,211,253 B1 | 5/2007 | Way |
| 7,226,998 B2 | 6/2007 | Gillies et al. |
| 7,323,549 B2 | 1/2008 | Lauder et al. |
| 7,465,447 B2 | 12/2008 | Gillies et al. |
| 2001/0053539 A1 | 12/2001 | Lauffer et al. |
| 2002/0037558 A1 | 3/2002 | Lo et al. |
| 2002/0081664 A1 | 6/2002 | Lo et al. |
| 2002/0142374 A1 | 10/2002 | Gallo et al. |
| 2002/0146388 A1 | 10/2002 | Gillies |
| 2002/0147311 A1 | 10/2002 | Gillies et al. |
| 2002/0192222 A1 | 12/2002 | Blumberg et al. |
| 2002/0193570 A1 | 12/2002 | Gillies et al. |
| 2003/0003529 A1 | 1/2003 | Bayer |
| 2003/0012789 A1 | 1/2003 | Blumberg et al. |
| 2003/0044423 A1 | 3/2003 | Gillies et al. |
| 2003/0049227 A1 | 3/2003 | Gillies et al. |
| 2003/0105294 A1 | 6/2003 | Gillies et al. |
| 2003/0139365 A1 | 7/2003 | Lo et al. |
| 2003/0139575 A1 | 7/2003 | Gillies |
| 2003/0157054 A1 | 8/2003 | Gillies et al. |
| 2003/0166163 A1 | 9/2003 | Gillies |
| 2003/0166877 A1 | 9/2003 | Gillies et al. |
| 2004/0013640 A1 | 1/2004 | Zardi et al. |
| 2004/0033210 A1 | 2/2004 | Gillies |
| 2004/0043457 A1 | 3/2004 | Schumacher et al. |
| 2004/0053366 A1 | 3/2004 | Lo et al. |
| 2004/0072299 A1 | 4/2004 | Gillies et al. |
| 2004/0082039 A1 | 4/2004 | Gillies et al. |
| 2004/0180035 A1 | 9/2004 | Gillies |
| 2004/0180386 A1 | 9/2004 | Carr et al. |
| 2004/0203100 A1 | 10/2004 | Gillies et al. |
| 2005/0042729 A1 | 2/2005 | Lo et al. |
| 2005/0069521 A1 | 3/2005 | Gillies et al. |
| 2005/0137384 A1 | 6/2005 | Gillies et al. |
| 2005/0164352 A1 | 7/2005 | Lauder et al. |
| 2005/0192211 A1 | 9/2005 | Gillies et al. |
| 2005/0202021 A1 | 9/2005 | Gillies |
| 2005/0202538 A1 | 9/2005 | Gillies et al. |
| 2005/0244418 A1 | 11/2005 | Gillies et al. |
| 2005/0261229 A1 | 11/2005 | Gillies et al. |
| 2006/0034836 A1 | 2/2006 | Gillies et al. |
| 2006/0141581 A1 | 6/2006 | Gillies et al. |
| 2006/0194952 A1 | 8/2006 | Gillies et al. |
| 2006/0228332 A1 | 10/2006 | Gillies et al. |
| 2006/0263856 A1 | 11/2006 | Gillies et al. |
| 2007/0036752 A1 | 2/2007 | Gillies et al. |
| 2007/0059282 A1 | 3/2007 | Gillies et al. |
| 2007/0104689 A1 | 5/2007 | Gillies et al. |
| 2007/0154453 A1 | 7/2007 | Webster et al. |
| 2007/0154473 A1 | 7/2007 | Super et al. |
| 2007/0178098 A1 | 8/2007 | Way et al. |
| 2007/0258944 A1 | 11/2007 | Gillies et al. |
| 2007/0287170 A1 | 12/2007 | Davis et al. |
| 2008/0025947 A1 | 1/2008 | Gillies et al. |

FOREIGN PATENT DOCUMENTS

| | | |
|---|---|---|
| CN | 93100115.3 | 7/1993 |
| DE | 37 12985 | 11/1988 |
| DE | 37 12985 A1 | 11/1988 |
| EP | 0 158 198 A1 | 10/1985 |
| EP | 0 211 769 A2 | 2/1987 |
| EP | 0 237 019 A2 | 9/1987 |
| EP | 0 256 714 A2 | 2/1988 |
| EP | 0 294 703 A2 | 12/1988 |
| EP | 0 308 936 131 | 3/1989 |
| EP | 0 314 317 131 | 5/1989 |
| EP | 0 318 554 131 | 6/1989 |
| EP | 0 319 012 A2 | 6/1989 |
| EP | 0 326 120 B1 | 8/1989 |
| EP | 0 350 230 A2 | 1/1990 |
| EP | 0 375 562 B1 | 6/1990 |
| EP | 0 396 387 A2 | 11/1990 |
| EP | 0 439 095 A2 | 7/1991 |
| EP | 0 511 747 A1 | 11/1992 |
| EP | 0 519 596 A1 | 12/1992 |
| EP | 0 601 043 131 | 6/1994 |
| EP | 0 640 619 A1 | 3/1995 |
| EP | 0 668 353 A1 | 8/1995 |
| EP | 0 699 755 A2 | 3/1996 |

| | | |
|---|---|---|
| EP | 0 428 596 B1 | 4/1996 |
| EP | 0 706 799 A2 | 4/1996 |
| EP | 0 428 267 B1 | 12/1996 |
| EP | 0 790 309 A1 | 8/1997 |
| EP | 0 433 827 B1 | 3/1998 |
| EP | 0 668 351 B1 | 9/1999 |
| EP | 1 088 888 A1 | 4/2001 |
| GB | 2 188 638 | 10/1987 |
| GB | 2 292 382 A | 2/1996 |
| JP | 63-267278 | 11/1988 |
| JP | 63-267296 | 11/1988 |
| WO | WO 86/01533 | 3/1986 |
| WO | WO 88/00052 | 1/1988 |
| WO | WO 88/09344 | 12/1988 |
| WO | WO 89/02922 | 4/1989 |
| WO | WO 89/09620 | 10/1989 |
| WO | WO 90/03801 | 4/1990 |
| WO | WO 91/00360 | 1/1991 |
| WO | WO 91/04329 | 4/1991 |
| WO | WO 91/08298 | 6/1991 |
| WO | WO 91/13166 | 9/1991 |
| WO | WO 91/14438 | 10/1991 |
| WO | WO 92/02240 | 2/1992 |
| WO | WO 92/08495 | 5/1992 |
| WO | WO 92/08801 | 5/1992 |
| WO | WO 92/10755 | 6/1992 |
| WO | WO 92/16562 | 10/1992 |
| WO | WO 93/03157 | 2/1993 |
| WO | WO 93/10229 | 5/1993 |
| WO | WO 93/20185 | 10/1993 |
| WO | WO 94/24160 | 10/1994 |
| WO | WO 94/25055 | 11/1994 |
| WO | WO 94/25609 | 11/1994 |
| WO | WO 95/05468 | 2/1995 |
| WO | WO 95/21258 | 8/1995 |
| WO | WO 95/28427 | 10/1995 |
| WO | WO 95/31483 | 11/1995 |
| WO | WO 96/04388 | 2/1996 |
| WO | WO 96/05309 | 2/1996 |
| WO | WO 96/08570 | 3/1996 |
| WO | WO 96/18412 | 6/1996 |
| WO | WO 96/31526 | 10/1996 |
| WO | WO 96/40792 | 12/1996 |
| WO | WO 97/00317 | 1/1997 |
| WO | WO 97/00319 | 1/1997 |
| WO | WO 97/15666 | 5/1997 |
| WO | WO 97/20062 | 6/1997 |
| WO | WO 97/24137 | 7/1997 |
| WO | WO 97/24440 | 7/1997 |
| WO | WO 97/26335 | 7/1997 |
| WO | WO 97/30089 | 8/1997 |
| WO | WO 97/33617 | 9/1997 |
| WO | WO 97/33619 | 9/1997 |
| WO | WO 97/34631 | 9/1997 |
| WO | WO 97/43316 | 11/1997 |
| WO | WO 98/00127 | 1/1998 |
| WO | WO 98/06752 | 2/1998 |
| WO | WO 98/28427 | 7/1998 |
| WO | WO 98/30706 | 7/1998 |
| WO | WO 98/46257 | 10/1998 |
| WO | WO 98/52976 | 11/1998 |
| WO | WO 98/59244 | 12/1998 |
| WO | WO 99/02709 | 1/1999 |
| WO | WO 99/03887 | 1/1999 |
| WO | WO 99/29732 | 6/1999 |
| WO | WO 99/43713 | 9/1999 |
| WO | WO 99/52562 | 10/1999 |
| WO | WO 99/53958 | 10/1999 |
| WO | WO 99/60128 | 11/1999 |
| WO | WO 99/62944 | 12/1999 |
| WO | WO 99/66054 | 12/1999 |
| WO | WO 00/01822 | 1/2000 |
| WO | WO 00/11033 | 3/2000 |
| WO | WO 00/24893 | 5/2000 |
| WO | WO 00/34317 | 6/2000 |
| WO | WO 00/40615 | 7/2000 |
| WO | WO 00/68376 | 11/2000 |
| WO | WO 00/69913 | 11/2000 |
| WO | WO 00/78334 | 12/2000 |
| WO | WO 01/07081 | 2/2001 |
| WO | WO 01/10912 | 2/2001 |
| WO | WO 01/36489 | 5/2001 |
| WO | WO 01/58957 | 8/2001 |
| WO | WO 02/02143 | 1/2002 |
| WO | WO 02/066514 | 8/2002 |
| WO | WO 02/072605 | 9/2002 |
| WO | WO 02/079232 | 10/2002 |
| WO | WO 02/079415 | 10/2002 |
| WO | WO 02/090566 | 11/2002 |
| WO | WO 03/015697 | 2/2003 |
| WO | WO 03/048334 | 6/2003 |
| WO | WO 03/077834 | 9/2003 |

OTHER PUBLICATIONS

U.S. Appl. No. 07/348,237, filed May 5, 1989, Rosenblum et. al.

Lode et. al. *Amplification of T Cell Mediated In name Responses by Antibody-Cytokine Fusion Proteins*. Immunological Investigations 2000, vol. 29, No. 2, pp. 117-120.

Reisfeld et. al. *Lmnunocytokines: a new approach to immunotherapy of melanoma*. Melanoma Research 1997, vol. 7. Suppl. 2, pp. S99-S106.

Abaza et. al., (1992), "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," *Journal of Protein Chemistry*, 11(5):433-444.

Abstract XP-002116766, Lupulescu, (1996), "Prostaglandins, Their Inhibitors and Cancer," *Prostaglandins. Leukotrienes and Essential Fatty Acids*, 54(2):83-94.

Afonso et. al., (1994), "The Adjuvant Effect of Interleukin-12 in a Vaccine Against Leishmania Major," *Science*, 263:235-237.

Angal et. al., (1993), "A Single Amino Acid Substitution Abolishes the Heterogeneity of Chimeric Mouse/Human (IgG4) Antibody," *Molecular Immunology*, 30(1):105-108.

Arenberg et. al., (1996), "Interferon-,y-inducible Protein 10 (IP-10) is an Angiostatic Factor that Inhibits Human Non-small Cell Lung Cancer (NSCLC) Tumorigenesis and Spontaneous Metastases," *J. Exp. Med.*, 184:981-992.

Bacha et. al., (1988), "Interleukin 2 Receptor-Targeted Cytotoxicity: Interleukin 2 Receptor-mediated Action of a Diphtheria Toxin-related Interleukin 2 Fusion Protein," *J. Exp. Med.*, 167:612-622.

Bachelot et. al., (1998), "Retrovirus-Mediated Gene Transfer of an Angiostatin-Endostatin Fusion Protein with Enhanced Anti-Tumor Properties In Vivo," *Proceedings of the Annual Meeting of the American Association for Cancer Research*, 39:271, Abstract #1856 (XP-002089298).

Barnett et. al., (1994), "Purification, Characterization and Selective Inhibition of Human Prostaglandin G/H Synthase 1 and 2 Expressed in the Baculovirus System," *Biochimica et Biophysica Acta*, 1209:130-139.

Baselga et. al., (1998), "Recombinant Humanized Anti-HER2 Antibody (Herceptin TM) Enhances the Antitumor Activity of Paclitaxel and Doxorubicin against HER3/neu Overexpressing Human Breast Cancer Xenografts," *Cancer Research*, 58:2825-2831.

Batova et. al., (1999), "The Ch14.18-GM-CSF Fusion Protein Is Effective at Mediating Antibody-dependent Cellular Cytotoxicity and Complement-dependent Cytotoxicity in Vitro," *Clinical Cancer Research*, 5:4259-4263.

Batra et. al., (1993), "Insertion of Constant Region Domains of Human IgGI into CD4-PE40Increases Its Plasma Half-Life," *Molecular Immunology*, 30(4):379-386.

Becker et. al., (1996), "An Antibody-Interleukin 2 Fusion Protein Overcomes Tumor Heterogeneity by Induction of a Cellular Immune Response," *Proc. Natl. Acad. Sci. USA*, 93:7826-7831.

Becker et. al., (1996), "Eradication of Human Hepatic and Pulmonary Melanoma Metastases in SCID Mice by Antibody-interleukin 2 Fusion Proteins," *Proc. Natl. Acad. Sci. USA*, 93:2702-2707.

Becker et. al., (1996), "Long-lived and Transferable Tumor Immunity in Mice after Targeted Interleukin-2 Therapy," *J. Clin. Invest.*, 98(12):2801-2804.

Becker et. al., (1996), "T Cell-mediated Eradication of Murine Metastatic Melanoma Induced by Targeted Interleukin-2 Therapy," *J. Exp. Med.*, 183(50):2361-2366.

Beutler et. al., (1988), "Tumor Necrosis, Cachexia, Shock, and Inflammation: A Common Mediator," *Annual Rev. Biochem.*, 57:505-518.

Bissery et. al., (1997), "The Taxoids," in *Cancer Therapeutics: Experimental and Clinical Agents*, Teicher (ed.), pp. 175-193.

Bitonti et. al., (2002), "Transepithelial Absorption of an Erythropoietin-Fc Fusion Protein After Delivery to the Central Airways," *Respiratory Drug Delivery*, 8:309-312.

Bjorn et. al., (1985), "Evaluation of Monoclonal Antibodies for the Development of Breast Cancer Immunotoxins," *Cancer Research*, 45:1214-1221.

Boehm et. al., (1997), "Antiangiogenic Therapy of Experimental Cancer Does Not Induce Acquired Drug Resistance," *Nature*, 390:404-407.

Boehm et. al., (1998), "Zinc-Binding of Endostatin Is Essential for Its Antiangiogenic Activity," *Biochemical and Biophysical Research Communications*, 252:190-194.

Boissel et. al., (1993), "Brythropoietin Structure-Function Relationships: Mutant Proteins that Test a Model of Tertiary Structure," *The Journal of Biological Chemistry*, 268(21):15983-15993.

Briggs et. al., (1974), "Hepatic Clearance of Intact and Desialylated Erythropoietin," *American Journal of Physiology*, 227(6):1385-1388.

Brooks et. al., (1994), "Integrin 003 Antagonists Promote Tumor Regression by Inducing Apoptosis of Angiogenic Blood Vessels," *Cell*, 79:1157-1164.

Buchli et. al., (1993), "Structural and Biologic Properties of a Human Aspartic Acid-126 Interleukin-2 Analog," *Archives of Biochemistry and Biophysics*, 307(2):411-415.

Burgess et. al., (1990), "Possible Dissociation of the Heparin-binding and Mitogenic Activities of Heparin Binding (Acidic Fibroblast) Growth Factor-1 from Its Receptor-binding Activities by Site-directed Mutagenesis of a Single Lysine Residue," *Journal of Cell Biology*, 111:2129-2138.

Canfield et. al., (1991), "The Binding Affinity of Human IgG for its High Affinity Fc Receptor is Determined by Multiple Amino Acids in the CH2 Domain and Is Modulated by the Hinge Region," *J. Exp. Med.*, 173(6):1483-1491.

Cao et. al., (1996), "Kringle Domains of Human Angiostatin: Characterization of the Anti-Proliferative Activity of Endothelial Cells," *The Journal of Biological Chemistry*, 271(46):29461-29467.

Cao et. al., (1997), "Kringle 5 of Plasminogen is a Novel Inhibitor of Endothelial Cell Growth," *The Journal of Biological Chemistry*, 272(36):22924-22928.

Capon et. al., (1989), "Designing CD4 Immunoadhesins for AIDS Therapy," *Nature*, 337:525-531.

Caton et. al., (1986), Structural and Functional Implications of a Restricted Antibody Response to a Defined Antigenic Region on the Influenza Virus Hemagglutinin, *The EMBO Journal*, 5(7):15.7_7 15.8.7.

Chan et. al., (1991), "Induction of Interferon ~yProduction by Natural Killer Cell Stimulatory Factor: Characterization of the Responder Cells and Synergy with Other Inducers," *J. Exp. Med.*, 173: 869-879.

Chang et. al., (1989), "Overview of Interleukin-2 as an Immunotherapeutic Agent," *Seminars in Surgical Oncology*, 5:385-390.

Chang et. al., (1996), "A Point Mutation in Interleukin-2 that Alters Ligand Internalization," *Journal of Biological Chemistry*, 271(23):13349-13355.

Chaudhary et. al., (1988), "Selective Killing of HIV-infected Cells by Recombinant Human *CD4-Pseudonionas* Exotoxin Hybrid Protein," *Nature*, 335:370-372.

Chaudhary et. al., (1989), "A Recombinant Immunotoxin Consisting of Two Antibody Variable Domains Fused to *Pseudomonas* Exotoxin," *Nature*, 339:394-397.

Chen et. al., (1997), "Eradication of Murine Bladder Carcinoma by Intratumor Injection of a Bicistronic Adenoviral Vector Carrying cDNAs for the IL-12 Heterodimer and Its Inhibition by the IL-12 p40 Subunit Homodimer," *Journal of Immunology*, 159(1):351-358.

Cheon et. al., (1994), "High-affinity Binding Sites for Related Fibroblast Growth Factor Ligands Reside Within Different Receptor Immunoglobulin-like Domains," *Proc. Natl. Acad. Sci. USA*, 91: 989-993.

Chuang et. al., (1993), "Effect of New Investigational Drug Taxol on Oncolytic Activity and Stimulation of Human Lymphocytes," *Gynecologic Oncology*, 49:291-298.

Chuang et. al., (1994), "Alteration of Lymphocyte Microtubule Assembly, Cytotoxicity, and Activation by the Anticancer Drug Taxol," *Cancer Research*, 54:1286-1291.

Cohen et. al., (1996), "Human Leptin Characterization," *Nature*, 382:589.

Cole et. al., (1997), "Human IgG2 Variants of Chimeric Anti-CD3 Are Nonmitogenic to T Cells," *Journal of Immunology*, 159:3613-3621.

Collins et. al., (1988), "Identification of Specific Residues of Human Interleukin 2 That Affect Binding to the 70-kDa Subunit (p70) of the Interleukin 2 Receptor," *Proc. Natl. Acad. Sci. USA*, 85:7709-7713.

Colombo et. al., (1996), "Amount of Interleukin 12 Available at the Tumor Site is Critical of Tumor Regression," *Cancer Research*, 56:2531-2534.

Cruse et. al., (eds.), (1995), *Illustrated Dictionary of Immunology*, pp. 156-157, CRC Press, NY.

D'Amato et. al., (1994), "Thalidomide is an Inhibitor of Angiogenesis," *Proc. Natl. Acad. Sci. USA*, 91:4082-4085.

D'Andrea et. al., (1992), "Production of Natural Killer Cell Stimulatory Factor (Interleukin 12) by Peripheral Blood Mononuclear Cells," *J. Exp. Med.*, 176:1387-1398.

Darling et. al., (2002), "Glycosylation of Erythropoietin Affects Receptor Binding Kinetics: Role of Electrostatic Interactions," *Biochemistry*, 41:14524-14531.

Davis et. al., (2003), "Immunocytokines: Amplification of Anti-cancer Immunity," *Cancer Immunol. Immunother.*, 52:297-308.

Ding et. al., (1988), "Zinc-Dependent Dimers Observed in Crystals of Human Endostatin," *Proc. Natl. Acad. Sci. USA*, 95:10443-10448.

Dolman et. al., (1998), "Suppression of Human Prostate Carcinoma Metastases in Severe Combined Immunodeficient Mice by Interleukin 2 Imunocytokine Therapy," *Clin. Cancer Research.*, 4(10):2551-2557.

Duncan et. al., (1988), "The Binding Site for Clq on IgG," *Nature*, 332:738-740.

Earnest et. al., (1992), "Piroxicam and Other Cyclooxygenase Inhibitors: Potential for Cancer Chemoprevention," *J. Cell. Biochem., Supp.*, 161:156-166.

Egrie et. al., (2001), "Development and Characterization of Novel Erythropoiesis Stimulating Protein (NESP)," *Nephrol. Dial. Transplant.*, 16(Supp 3):3-13.

Eisenthal, (1990), "Indomethacin Up-regulates the Generation of Lymphokine-Activated Killer-cell Activity and Antibody-dependent Cellular Cytotoxicity Mediated by Interleukin-2," *Cancer Immunol. Immunother.*, 31:342-348.

Elliott et. al., (1997), "Mapping of the Active Site of Recombinant Human Erythropoietin," *Blood*, 89(2):493-502.

Fell et. al., (1991), "Genetic Construction and Characterization of A Fusion Protein Consisting of a Chimeric F(ab') with Specificity for Carcinomas and Human IL-2," *J. Immunology*, 146(7):2446-2452.

Fell et. al., (1992), "Chimeric L6 Anti-tumor Antibody: Genomic Construction, Expression, and Characterization of the Antigen Binding Site," *J. Biological Chemistry*, 267:15552-15558.

Fibi et. al., (1995), "N- and O-Glycosylation Muteins of Recombinant Human Erythropoietin Secreted From B H K-21 Cells," *Blood*, 85(5):1229-1236.

Friedman et. al., (1998), "Leptin and the Regulation of Body Weight in Mammals," *Nature*, 395:763-770.

Frost et. al., (1997), "A Phase I/IB Trial of Murine Monoclonal Anti-GD2 Antibody 14.G2a Plus Interleukin-2 in Children with Refractory Neuroblastoma," *Cancer*, 80(2):317-333.
Gan et. al., (1999), "Specific Enzyme-linked Immunosorbent Assays for Quantitation of Antibody-cytokine Fusion Proteins," *Clinical and Diagnostic Laboratory Immunology*, 6(2):236-42.
Gasson et. al., (1984), "Purified Human Granulocyte Macrophage Colony-Stimulating Factor: Direct Action on Neutrophils," *Science*, 226:1339-1342.
Gately et. al., (1998), "The Interleukin-12/Interleukin-12-Receptor System: Role in Normal and Pathologic Immune Responses," *Annu. Rev. Immunol.*, 16:495-521.
Gillessen et. al., (1995), "Mouse Interleukin-12 (IL-12) p40 Homodimer: A Potent IL-12 Antagonist," *Eur. J. Immunol.*, 25:200-206.
Gillies et. al., (1989), "Expression of Human Anti-Tetanus Toxoid Antibody in Transfected Murine Myeloma Cells," *Bio/Technology*, 7:799-804.
Gillies et. al., (1989), "High-Level Expression of Chimeric Antibodies Using *Adapted cDNA Variable Region* Cassettes,"-7-*Immunol Iylethod* 25:191-202.
Gillies et. al., (1990), "Antigen Binding and Biological Activities of Engineered Mutant Chimeric Antibodies with Human Tumor Specificities," *Hum. Antibod. Hybridomas*, 1(1):47-54.
Gillies et. al., (1991), "Expression of Genetically Engineered Immunoconjugates of Lymphotoxin and a Chimeric Anti-ganglioside GD2 Antibody," *Hybridoma.*, 10(3):347-56.
Gillies et. al., (1992), "Antibody-Targeted Interleukin 2 Stimulates T-Cell Killing of Autologous Tumor Cells," *Proc. Natl. Acad. Sci. USA*, 89:1428-1432.
Gillies et. al., (1993), "Biological Activity and In Vivo Clearance of Antitumor Antibody/Cytokine Fusion Proteins," *Bioconjugate Chem.*, 4(3):230-235.
Gillies et. al., (1998), "Antibody-IL-12 Fusion Proteins are Effective in SCID Mouse Models of Prostate and Colon Carcinoma Metastases," *J. Immunology*, 160:6195-6203.
Gillies et. al., (1999), "Improving the Efficacy of Antibody-Interleukin 2 Fusion Proteins by Reducing Their Interaction with Fc Receptors," *Cancer Research*, 59:2159-2166.
Gillies et. al., (2002), "Bi-functional Cytokine Fusion Proteins for Gene Therapy and Antibody-targeted Treatment of Cancer," *Cancer Immunol. Immunother.*, 51(8):449-60.
Gillies et. al., (2002), "Improved Circulating Half-life and Efficacy of an Antibody-interleukin 2 Immunocytokine Based on Reduced Intracellular Proteolysis," *Clin. Cancer Research*, 8(1):210-216.
Gillis et. al., (1978), "°T Cell Growth Factor: Parameters of Production And A Quantitative Microassay for Activity," *J. Immunology*, 120(6):2027-2032.
Goeddel et. al., (1986), "Tumor Necrosis Factors: Gene Structure and Biological Activities," *Cold Spring Harb. Symp. Quant. Biol.*, 51:597-609.
Greene et. al., (1975), "Neuronal Properties of Hybrid Neuroblastoma X Sympathetic Ganglion Cells," *Proc. Natl. Acad. Sci. USA*, 72(12):4923-4927.
Gren et. al., (1983), "A New Type of Leukocytic Interferon," English Translation of *Dokl. Akad. Nauk. SSSR.*, 269(4):986-990.
Griffon-Etienne et. al., (1999), "Taxane-induced Apoptosis Decompresses Blood Vessels and Lowers Interstitial Fluid Pressure in Solid Tumors: Clinical Implications," *Cancer Research*, 59:3776-3782.
Grimaldi et. al., (1989), "The t(5;14) Chromosomal Translocation in a Case of Acute Lymphocytic Leukemia Joins the Interleukin-3 Gene to the Immunoglobulin Heavy Chain Gene," *Blood*, 73(8):2081-2085.
Guyre et. al., (1997), "Increased Potency of Fc-receptor-targeted Antigens," *Cancer Immunol. Immunother.*, 45:146-148.
Hammerling et. al., (1996), "In Vitro Bioassay for Human Erythropoietin Based on Proliferative Stimulation of an Erythroid Cell Line and Analysis of Carbohydrate-dependent Microheterogeneity," *Journal of Pharmaceutical and Biomedical Analysis*, 14:1455-1469.
Hank et. al., (1996), "Activation of Human Effector Cells by a Tumor Reactive Recombinant Anti-ganglioside GD2 Interleukin-2 Fusion Protein (ch.14.18-IL2)," *Clin Cancer Research*, 2(12):1951-1959.
Hank et. al., (2003), "Determination of Peak Serum Levels and Immune Response to the Humanized Anti-ganglioside Anti body-interleukin-2 Immunocytokine," in *Methods in Molecular Medicine vol. 85: Novel Anticancer Drug Protocols*, Buolamwini et. al., (eds.), pp. 123-131, Humana Press Inc., Totowana, NJ.
Haraguchi, (1994), "Isolation of GD3 Synthase Gene by Expression Cloning of GM3 a-2,8-sialyltransferase cDNA using anti-GD2 Monoclonal Antibody," *Proc. Natl. Acad. Sci. USA*, 91(22):10455-10459.
Harris et. al., (1993), "Therapeutic Antibodies—the Coming of Age," *Trends in Biotechnology*, 11:42-44.
Harris, (1995), "Processing of C-terminal Lysine and Arginine Residues of Proteins Isolated from Mammalian Cell Culture," *J. Chromatography A*, 705:129-134.
Harvill et. al., (1995), "An IgG3-IL2 Fusion Protein Activates Complement, Binds FcγRI, Generates LAK Activity and Shows Enhanced Binding to the High Affinity IL-2R," *Immunotechnology*, 1:95-105.
Harvill et. al., (1996), "In Vivo Properties of an IgG3-IL-2 Fusion Protein: A General Strategy for Immune Potentiation," *J. Immunology*, 157(7):3165-3170.
Hazama et. al., (1993), "Adjuvant-Independent Enhanced Immune Responses to Recombinant Herpes Simplex Virus Type 1 Glycoprotein D by Fusion with Biologically Active Interleukin-2," *Vaccine*, 11(6):629-636.
He et. al., (1998), "Humanization and Pharmacokinetics of a Monoclonal Antibody with Specificity for Both E-and P-Selectin," *J. Immunology*, 160:1029-1035.
Heijnen et. al., (1996), "Antigen Targeting to Myeloid-specific Human FcγRI/CD64 Triggers Enhanced Antibody Responses in Transgenic Mice," *J. Clin. Invest.*, 97(2):331-338.
Heinzel et. al., (1997), "In Vivo Production and Function of IL-12 p40 Homodimers," *J. Immunology*, 158:4381-4388.
Hellstrom et. al., (1986), "Antitumor Effects of L6, an IgG2a Antibody that Reacts with Most Human Carcinomas," *Proc. Natl. Acad. Sci. USA*, 83: 7059-7063.
Henkart, (1985), "Mechanism of Lymphocyte-Mediated Cytotoxicity," *Ann. Rev. Immunol.*, 3:31-58.
Herrmann et. al., (1989), "Hematopoietic Responses With Advanced Malignancy Treated With Recombinant Human Granulocyte-Macrophage Colony-Stimulating Factor," *Journal of Clinical Oncology*, 7(2):159-167.
Hezareh et. al., (2001), "Effector Function Activities of a Panel of Mutants of a Broadly Neutralizing Antibody against Human Immunodeficiency Virus Type 1," *J. Virology*, 75(24):12161-12168.
Hohenester et. al., (1998), "Crystal Structure of the Angiogenesis Inhibitor Endostatin at 1.5 A Resolution," *EMBO Journal*, 17(6):1656-1664.
Holden et. al., (2001), "Augmentation of Anti-Tumor Activity of KS-IL2 Immunocytokine with Chemotherapeutic Agents," *Proceedings of the American Association for Cancer Research*, 42:683, Abstract No. 3675 (XP-002195344).
Holden et. al., (2001), Augmentation of Antitumor Activity of an Antibody-Interleukin 2 Immunocytokine with Chemotherapeutic Agents, *Clinical Cancer Research*, 7:28622869.
Hoogenboom et. al., (1991), "Construction and Expression of Antibody-tumor Necrosis Factor Fusion Proteins," *Molecular Immunology*, 28(9):1027-1037.
Hoogenboom et. al., (1991), "Targeting of Tumor Necrosis Factor to Tumor Cells Secretion by Myeloma Cells of a Genetically Engineered Antibody-Tumor Necrosis Factor Hybrid Molecule," *Biochim. And Biophys. Acta*, 1096(4):345-354 (Abstract).
Hornick et. al., (1999), "Pretreatment with a Monoclonal Antibody/Interleukin-2 Fusion Protein Directed Against DNA Enhances the Delivery of Therapeutic Molecules to Solid Tumors," *Clin. Cancer Research*, 5:51-60.
Hu et. al., (1996), "A Chimeric Lym-1/Interleukin 2 Fusion Protein for Increasing Tumor Vascular Permeability and Enhancing Antibody Uptake," *Cancer Research*, 56:4998-5004.
Huck et. al., (1986), "Sequence of a Human Immunoglobulin Gamma 3 Heavy Chain Constant Region Gene: Comparison With the Other Human Cγ genes," *Nucleic Acids Research*, 14(4):1779-1789.

Huse et. al., (1989), "Generation of a Large Combinatorial Library of the Immunoglobulin Repertoire in Phage Lambda," *Science*, 246:1275-1281.

Idusogie et. al., (2000), "Mapping of the Clq Binding Site on Rituxan, a Chimeric Antibody with a Human IgGI Fc," *J. Immunology*, 164(8):4178-4184.

Imboden et. al., (2001), "The Level of MHC Class I Expression on Murine Adenocarcinoma Can Change the Antitumor Effector Mechanism of Immunocytokine Therapy," *Cancer Research*, 61(4):1500-7.

Ingber et. al., (1990), "Synthetic Analogues of Fumagillin that Inhibit Angiogenesis and Suppress Tumour Growth," *Nature*, 348:555-557.

Jones et. al., (1986), "Replacing the Complementarity-determining Regions in a Human Antibody with Those from a Mouse," *Nature*, 321:522-525.

Ju et. al., (1987), "Structure-Function Analysis of Human Interleukin-2: Identification of Amino Acid Residues for Biological Activity," *Journal of Biological Chemistry*, 262(12):5723-5731.

Jung et. al., (1986), "Activation of Human Peripheral Blood Mononuclear Cells by Anti-T3: Killing of Tumor Target Cells Coated with Anti-target-anti-T3 Conjugates," *Proc. Natl. Acad. Sci. USA*, 83:4479-4483.

Junghans et. al., (1996), The Protection Receptor of IgG Catabolism is the B2-MiGroglobulin-containing Neonatal Intestinal Transport Receptor, *Proc. Natl. Acad. Sci. USA*, 1 93(11):5512-5516.

Kang et. al., (1991), "Antibody Redesign by Chain Shuffling from Random Combinatorial Immunoglobulin Libraries," *Proc. Natl. Acad. Sci. USA*, 88:11120-11123.

Kappel et. al., (1992), "Regulating Gene Expression in Transgenic Animals," *Current Opinion in Biotechnology*, 3:548-553.

Kato et. al., (1997), "Mechanism for the Nonlinear Pharmacokinetics of Erythropoietin in Rats," *The Journal of Pharmacology and Experimental Therapeutics*, 283:520-527.

Kato et. al., (1998), "Pharmacokinetics of Erythopoietin in Genetically Anemic Mice," *Drug Metabolism and Disposition*, 26(2):126-131.

Karpovsky et. al., (1984), "Production of Target-Specific Effector Cells using Hetero-Cross Linked Aggregate Containing Anti-Target Cell and AntiFcy Receptor Antibodies," *Journal of Experimental Medicine*, 1609(6):1686-1701.

Kendra et. al., (1999), "Pharmacokinetics and Stability of the ch14.18-Interleukin-2 Fusion Protein in Mice," *Cancer Immunol. Immunother.*, 48:219-229.

Kim et. al., (1997), "An Ovalbumin-IL-12 Fusion Protein is More Effective than Ovalbumin Plus Free Recombinant IL-12 in Inducing a T Helper Cell Type 1-dominated Immune Response and Inhibiting Antigen-Specific IgE Production," *J. Immunology*, 158(9):4137-4144.

Kim et. al., (1999), "Cytokine Molecular Adjuvants Modulate Immune Responses Induced by DNA Vaccine Constructs for HIV-1 and SIV," *Journal of Interferon and Cytokine Research*, 19:77-84.

Kitamura et. al., (1989), "Establishment and Characterization of a Unique Human Cell Line that Proliferates Dependently on GM-CSF, IL-3, or Erythropoietin," *Journal of Cellular Physiology*, 140:323-334.

Kranz et. al., (1984), "Attachment of an Anti-receptor Antibody to Non-target Cells Renders Them Susceptible to Lysis by a Clone of Cytotoxic T Lymphocytes," *Proc. Natl. Acad. Sci. USA*, 81:7922-7926.

Kuo et. al., (2001), "Oligomerization-dependent Regulation of Motility and Morphogenesis by the Collagen XVIII NC1/Endostatin Domain," *Journal of Cell Biology*, 152(6):1233-1246.

Kushner et. al., (2001), "Phase II Trial of the Anti-GD2 Monoclonal Antibody 3F8 and Granulocyte-Macrophage Colony-Stimulating Factor for Neuroblastoma," *J. Clinical Oncology*, 19(22):4189-94.

LaVallie et. al., (1993), "Cloning and Functional Expression of a cDNA Encoding the Catalytic Subunit of Bovine Enterokinase," *Journal of Biological Chemistry*, 268(31):23311-23317.

Lazar et. al., (1988), "Transforming Growth Factor a: Mutation of Aspartic Acid 47 and Leucine 48 Results in Different Biological Activities," *Molecular and Cellular Biology*, 8(3):1247-1252.

LeBerthon et. al., (1991), "Enhanced Tumor Uptake of Macromolecules Induced by a Novel Vasoactive Interleukin 2 Immunoconjugate," *Cancer Research*, 51:2694-2698.

Lieschke, et. al., (1997), "Bioactive Murine and Human Interleukin-12 Fusion Proteins which Retain Antitumor Activity In Vivo," *Nature Biotechnology*, 15(1):35-40.

Linsley et. al., (1991), "CTLA-4 is a Second Receptor for B Cell Activation Antigen B7," *J. Exp. Med.*, 174(3):561-569.

Liu et. al., (1985), "Heteroantibody Duplexes Target Cells for Lysis by Cytotoxic T Lymphocytes," *Proc. Natl. Acad. Sci. USA*, 82:8648-8652.

Liu et. al., (1988), "Hormone Conjugated with Antibody to CD3 Mediates Cytotoxic T Cell Lysis of Human Melanoma Cells," *Science*, 239:395-398.

Liu et. al., (1998), "Immunostimulatory CpG Oligodeoxynucleotides Enhance the Immune Response to Vaccine Strategies Involving Granulocyte-Macrophage Colony-Stimulating Factor," *Blood*, 92(10):3730-3736.

Lo et. al., (1998), "High Level Expression and Secretion of Fc-X Fusion Proteins in Mammalian Cells," *Protein Engineering*, 11(6):495-500.

Locatelli et. al., (2001), "Darbepoetin alfa Amgen," *Current Opinion in Investigational Drugs*, 2:1097-1104.

Lode et. al., (1997), "Targeted Interleukin-2 Therapy for Spontaneous Neuroblastoma Metastases to Bone Marow," *J. Natl. Cancer Inst.*, 89(21):1586-94.

Lode et. al., (1998), "Immunocytokines: A Promising Approach to Cancer Immunotherapy," *Pharmacol. Ther.*, 80(3):277-292.

Lode et. al., (1998), "Natural Killer Cell-Mediated Eradication of Neuroblastoma Metastases to Bone Marrow by Targeted Interleukin-2 Therapy," *Blood*, 91(5):1706-1715.

Lode et. al., (1999), "Synergy Between an Antiangiogenic Integrin av Antagonist and an Antibody-cytokine Fusion Protein Eradicates Spontaneous Tumor Metastases," *Proc. Natl. Acad. Sci. USA*, 96:1591-1596.

Lode et. al., (1999), "Tumor-targeted IL-2 Amplifies T Cell-mediated Immune Response Induced by Gene Therapy with Single-chain IL-12," *Proc. Natl. Acad. Sci. USA*, 96:8591-8596.

Lode et. al., (2000), "What To Do With Targeted IL-2," *Drugs of Today*, 36(5):321-336.

Lode et. al., (2000), "Melanoma Immunotherapy by Targeted IL-2 Depends on CD4(+) T-cell Help Mediated by CD40/CD40L Interaction," *J. Clin. Invest.*, 105(11):1623-30.

Macdougall, (2002), "Optimizing the Use of Erythropoietic Agents-Pharmacokinetic and Pharmacodynamic Considerations," *Nephrol. Dial. Transplant.*, 17(Supp 5):66-70.

Maloney et. al., (1994), "Phase I Clinical Trial Using Escalating Single-Dose Infusion of Chimeric Anti-CD20 Monoclonal Antibody (IDEC-C2B8) in Patients with Recurrent B-Cell Lymphoma," *Blood*, 84(8):2457-2466.

Mark et. al., (1992), "Expression and Characterization of Hepatocyte Growth Factor Receptor-IgG Fusion Proteins," *Journal of Biological Chemistry*, 267(36):26166-26171.

Martinotti et. al., (1995), "CD4 T Cells Inhibit In Vivo the CD8-Mediated Immune Response Against Murine Colon Carcinoma Cells Transduced with Interleukin-12 Genes," *Eur. J. Immunol.* 25:137-146.

Medesan et. al., (1997), "Delineation of the Amino Acid Residues Involved in Transcytosis and Catabolism of Mouse IgG1," *J. Immunology*, 158(5):2211-2217.

Metelitsa et. al., (2002), "Antidisialoganglioside/granulocyte Macrophage-colony-stimulating Factor Fusion Protein Facilitates Neutrophil Antibody-dependent Cellular Cytotoxicity and Depends on FcyRII (CD32) and Mac-1 (CD1 1b/CD18) for Enhanced Effector Cell Adhesion and Azurophil Granule Exocytosis," *Blood*, 99(11):4166-73.

Mestre et. al., (1997), "Retinoids Suppress Epidermal Growth Factor-induced Transcription of Cyclooxygenase—2 in Human Oral Squamous Carcinoma Cells,"*Cancer Research*, 57:2890-2895.

Mosmann et. al., (1989), "TH1 and TH2 Cells: Different Patterns of Lymphokine Secretion Lead to Different Functional Properties," *Ann. Rev. Immunol.*, 7:145-173.

Mott et. al., (1995), "The Solution Structure of the F42A Mutant of Human Interleukin 2," *J. Mol. Biol.*, 247:979-994.

Mueller et. al., (1997), "Humanized Porcine VCAM-specific Monoclonal Antibodies with Chimeric IgG2/G4 Constant Regions Block Human Leukocyte Binding to Porcine Endothelial Cells," *Molecular Immunology*, 34(6):441-452.

Mullins et. al., (1997), "Taxol-mediated Changes in Fibrosarcoma-induced Immune Cell Function: Modulation of Antitumor Activities," *Cancer Immunol. Immunother*, 45:20-28.

Mullins et. al., (1998), "Interleukin-12 Overcomes Paclitaxel-mediated Suppression of T-cell Proliferation," *Immunopharmacol. Immunotoxicol.*, 20(4):473-492.

Murphy et. al., (1986), "Genetic Construction, Expression, and Melanoma-selective Cytotoxicity of a Diphtheria Toxin-related a-melanocyte-stimulating Hormone Fusion Protein," *Proc. Natl. Acad. Sci. USA*, 83:8258-8262.

Murphy, (1988), "Diphtheria-related Peptide Hormone Gene Fusions: A Molecular Gene Approach to Chimeric Toxin Development," in *Immunotoxins*, pp. 123-140, Frankel (ed.), Kluwer Acad. Pub.

Naramura et. al., (1994), "Mechanisms of Cellular Cytotoxicity Mediated by a Recombinant Antibody-IL2 Fusion Protein Against Human Melanoma Cells," *Immunology Letters*, 39:91-99.

Neal et. al., (2003), "NXS2 Murine Neuroblastomas Express Increased Levels of MHC Class I Antigens upon Recurrence Following NK-dependent Immunotherapy," *Cancer Immunoi. Immunother.*, 53:41-52.

Nedwin et. al., (1985), "Human Lymphotoxin and Tumor Necrosis Factor Genes: Structure, Homology and Chromosomal Localization," *Nucleic Acids Research*, 13(17):6361-6373.

Netti et. al., (1995), "Time-dependent Behavior of Interstitial Fluid Pressure in Solid Tumors: Implications for Drug Delivery," *Cancer Research*, 55:5451-5458.

Netti et. al., (1999), "Enhancement of Fluid Filtration Across Tumor Vessels: Implication for Delivery of Macromolecules," *Proc. Nat. Acad. Sci. USA*, 96:3137-3142.

Neuberger et. al., (1984), "Recombinant Antibodies Prossessing-Novel Effector Functions," *Nature*, 312:604-608.

Ngo et. al., (1994), "Computational Complexity, Protein Structure Prediction, and the Levinthal Paradox," in *The Protein Folding Problem and Tertiary Structure Prediction*, Merz et. al. (eds.), pp. 433-440 and 492-495, Birkhauser, Boston, MA.

Niethammer et. al., (2002) "An Oral DNA Vaccine Against Human Carcinoembryonic Antigen (CED) Prevents Growth and Dissemination of Lewis Lung Carcinoma in CEA Transgenic Mice," *Vaccine*, 20:421-429.

Niethammer et. al., (2001) "Targeted Interleukin 2 Therapy Enhances Protective Immunity Induced by an Autologous Oral DNA Vaccine against Murine Melanoma," *Cancer Research*, 61(16):6178-84.

Nimtz et. al., (1993), "Structures of Sialylated Oligosaccharides of Human Erythropoietin Expressed in Recombinant BHK-21 Cells," *Eur. J. Biochem.*, 213:39-56.

O'Reilly et. al., (1994), "Angiostatin: A Novel Angiogenesis Inhibitor That Mediates the Suppression of Metastases by a Lewis Lung Carcinoma," *Cell*, 79:315-328.

O'Reilly et. al., (1996), "Angiostatin Induces and Sustains Dormancy of Human Primary Tumors in Mice," *Nature Medicine*, 2(6):689-692.

O'Reilly et. al., (1997), "Endostatin: An Endogenous Inhibitor of Angiogenesis and Tumor Growth," *Cell*, 88:277-285.

Park et. al., (2000), "Efficiency of Promoter and Cell Line in High-level Expression of Erythropoietin," *Biotechnol. Appl. Biochem.*, 32:167-172.

Pancook et. al., (1996), "Eradication of Established Hepatic Human Neuroblastoma Metastases in Mice with Severe Combined Immunodeficiency by Antibody-targeted Interleukin-2," *Cancer Immunol. Immunother.*, 42(2):88-92.

Pastan et. al., (1989), "*Pseudomonas* Exotoxin: Chimeric Toxins," *Journal of Biological Chemistry*, 264(26):15157-15160.

Paul et. al., (1988), "Lymphotoxin," *Ann. Rev. Immunol.*, 6:407-438.

Perez et. al., (1986), Specific Targeting of Human Peripheral Blood T Cells by Heteroaggregates-Containing Anti-T3 Crosslinked to Anti-Target Cell Antibodies, *J. Exp. Med.*, 163:166-178.

Perez et. al., (1989), "Isolation and Characterization of a cDNA Encoding the KS 1/4 Epithelial Carcinoma Marker," *J. Immunology*, 142(10):3662-3667.

Polizzi et. al., (1999), "A Novel Taxane with Improved Tolerability and Therapeutic Activity in a Panel of Human Tumor Xenografts," *Cancer Research*, 59:1036-1040.

Putzer et. al., (1997), "Interleukin 12 and 137-1 Costimulatory Molecule Expressed by an Adenovirus Vector Act Synergistically to Facilitate Tumor Regression," *Proc. Natl. Acad. Sci. USA*, 94(20):10889-10894.

Reisfeld et. al., (1996), "Antibody-interleukin 2 Fusion Proteins: A New Approach to Cancer Therapy," *J. Clin. Lab. Anal.*, 10:160-166.

Reisfeld et. al., (1996), "Involvement of B Lymphocytes in the Growth Inhibition of Human Pulmonary Melanoma Metastases in Athymic *nu/nu* Mice by an Antibody-lymphotoxin Fusion Protein," *Cancer Research*, 56(8):1707-1712.

Reisfeld et. al., (1996), "Recombinant Antibody Fusion Proteins for Cancer Immunotherapy," *Current Topics in Microbiology and Immunology*, 213:27-53.

Riethmuller et. al., (1994), "Randomised Trial of Monoclonal Antibody for Adjuvant Therapy of Resected Dukes' C Colorectal Carcinoma," *The Lancet*, 343:1177-1183.

Roessler et. al., (1994), "Cooperative Interactions Between the Interleukin 2 Receptor $\alpha$ and $\beta$ Chains Alter the Interleukin 2-binding Affinity of the Receptor Subunits," *Proc. Natl. Acad. Sci. USA*, 91:3344-3347.

Roitt et. al., (1993), "The Role of TH Cells in the Selection of Effector Mechanisms Directed Against Target Antigens," *Immunology*, P Ed., pp. 8.3-8.4.

Rosenberg, (1988), "Immunotherapy of Cancer Using Interleukin 2: Current Status and Future Prospects," *Immunology Today*, 9(2):58-62.

Rozwarski et. al., (1994), "Structural Comparisons Among the Short-chain Helical Cytokines," *Structure*, 2(3):159-173.

Ruehlmann et. al., (2001), "MIG (CIXCL9) Chemokine Gene Therapy Combines with Antibody-cytokine Fusion Protein to Suppress Growth and Dissemination of Murine Colon Carcinoma," *Cancer Research*, 61(23):8~198=503.

Sabzevari et. al., (1994), "A Recombinant Antibody-interleukin 2 Fusion Protein Suppresses Growth of Hepatic Human Severe Combined Immunodeficiency Mice," *Proc. Natl. Acad. Sci. USA*, 91(20):9626-30.

Santon et. al., (1986), "Effects of Epidermal Growth Factor Receptor Concentration on Tumorigenicity of A431 Cells in Nude Mice," *Cancer Research*, 46:4701-4705.

Sasaki et. al., (1998), "Structure, Function and Tissue Forms of the C-terminal Globular Domain of Collagen XVIII Containing the Angiogenesis Inhibitor Endostatin," *EMBO Journal*, 17(15):4249-4256.

Sauve et. al., (1991), "Localization in Human Interleukin 2 of the Binding Site to the a-chain (p55) of the Interleukin 2 Receptor," *Proc. Natl. Acad. Sci. USA*, 88:4636-4640.

Schnee et. al., (1987), "Construction and Expression of a Recombinant Antibody-targeted Plasminogen Activator," *Proc. Natl. Acad. Sci. USA*, 84:6904-6908.

Schoenhaut et. al., (1992), "Cloning and Expression of Murine IL-12," *J. Immunology*, 148(11):3433-3340.

Seidenfeld et. al., (2001), "Bpoietin Treatment of Anemia Associated with Cancer Therapy: A Systematic Review and Meta-analysis of Controlled Clinical Trials," *Journal of National Cancer Institute*, 93(16):1204-1214.

Senter et. al., (1988), "Anti-tumor Effects of Antibody-alkaline Phosphatase Conjugates in Combination with Etoposide Phosphate," *Proc. Natl. Acad. Sci. USA*, 85(13):4842-4846.

Shanafelt et. al., (2000), "A T-cell-Selective Interleukin 2 Mutein Exhibits Potent Antitumor Activity and is Well Tolerated In Vivo," *Nature Biotechnology*, 18:1197-1202.

Sharma et. al., (1999), T cell-derived IL-10 Promotes Lung Cancer Growth by Suppressing Both T cell and APC Function, *Journal of Immunology*, 163:5020-5028.

Shen et. al., (1986), "Heteroantibody-Mediated Cytotoxicity: Antibody to the High Affinity Fc Receptor for IgG Mediates Cytotoxicity by Human Monocytes That is Enhanced by Interferon-y and is Not Blocked by Human IgG," *J. Immunology*, 137(11):3378-3382.

Shiff et. al., (1995), "Sulindac Sulfide, an Asprin-like Compound, Inhibits Proliferation, Causes Cell Cycle Quiescence, and Induces Apoptosis in HT-29 Colon Adenocarcinoma Cells," *Journal of Clinical Investigation*, 96:491-503.

Shin et. al., (1990), "Expression and Characterization of an Antibody-Binding-Speci.ficity Joined to Insulin-like Growth Factor 1: Potential Applications for Cellular Targeting," *Proc. Natl. Acad. Sci. USA*, 87:5322-5326.

Shinkawa et. al., (2003), "The Absence of Fucose But Not the Presence of Galactose or Bisecting N-Acetylglucosamine of Human IgGI Complex-type Oligosaccharides Shows the Critical Role of Enhancing Antibody-dependent Cellular Cytotoxicity," *J. Biol. Chem.*, 278:3466-3473.

Sim et. al., (1997), "A Recombinant Human Angiostatin Protein Inhibits Experimental Primary and Metastatic Cancer," *Cancer Research*, 57:1329-1334.

Spiekermann et. al., (2002), "Receptor-mediated Immunoglobulin G Transport Across Mucosal Barriers in Adult Life: Functional Expression of FcRn in the Mammalian Lung," *J. Exp. Med.*, 196:303-310.

Stevenson et. al., (1997), "Conjugation of Human Fcy in Closed-Hinge or Open-Hinge Configuration to Fab'y and Analogous Ligands," *J. Immunology*, 158:2242-2250.

Strom et. al., (1996), "Therapeutic Approach to Organ Transplantation," Chapter 36, pp. 451-456, in *Therapeutic Immunology*, Austen et. al., (eds.), Blackwell Science.

Sulitzeanu, (1993), "Immunosuppressive Factors in Human Cancer," pp. 247-266 in *Advances in Cancer Research*. vol. 60, Vande Woude et. al. (eds.), Academic Press, Inc.

Syed et. al., (1998), "Efficiency of Signaling Through Cytokine Receptors Depends Critically on Receptor Orientation," *Nature*, 395:511-516.

Taniguchi et. al., (1983), "Structure and Expression of a Cloned cDNA for Human Interleukin-2," *Nature*, 302:305-309.

Tao et. al., (1989), "Studies of Aglycosylated Chimeric Mouse IgG: Role of Carbohydrate in the Structure and Effector Functions Mediated by the Human IgG Constant Region," *J. Immunology*, 143(8):2595-2601.

Tao et. al., (1993), "Structural Features of Human Immunoglobulin G that Determine Isotype-Differences in Complement Activation," *J. Exp. Med.*, 178(2):661-667.

Teicher et. al., (1994), "Potentiation of Cytotoxic Cancer Therapies by TNP-470 Alone and With Other Anti-Angiogenic Agents," *Int. J. Cancer*, 57:920-925.

*The Merck Manual of Diagnosis and Therapy*, 17th Ed., (1999) pp. 990-993 and 1278-1283.

Thommesen et. al., (2000), "Lysine 322 in the Human IgG3 CH2 Domain is Crucial for Antibody Dependent Complement Activation," *Mol. Immunol.*, 37(16):995-1004.

Till et. al., (1988), "An Assay that Predicts the Ability of Monoclonal Antibodies to Form Potent Ricin A Chain-containing Immunotoxins," *Cancer Research*, 48(5):1119-1123.

Till et. al., (1988), "HIV-Infected Cells are Killed by rCD4-Ricin A Chain," *Science*. 242:1166-1168.

Trinchieri, (1994), "Interleukin-12: A Cytokine Produced by Antigen-Presenting Cells With Immunoregulatory Functions in the Generation of T-Helper Cells Type 1 and Cytotoxic Lymphocytes," *Blood*, 84:4008-4027.

Vagliani et. al., (1996), "Interleukin 12 Potentiates that Curative Effect of a Vaccine Based on Interleukin 2-transduced Tumor Cells," *Cancer Research*, 56:467-470.

Varki et. al., (1984), "Antigens Associated with a Human Lung Adenocarcinoma Defined by Monoclonal Antibodies," *Cancer Research*, 44:681-687.

Verhoeyen et. al., (1988), "Reshaping Human Antibodies: Grafting an Antilysozyme Activity," *Science*, 239:1534-1536.

Villunger et. al., (1997), "Constitutive Expression of Fas (Apo-1/CD95) Ligand on Multiple Myeloma Cells: A Potential Mechanism of Tumor-induced Suppression of Immune Surveillance," *Blood*, 90(1):12-20.

Watanabe et. al., (1997), "Long-term Depletion of Naive T cells in Patients Treated for Hodgkin's Disease," *Blood*, 90(9):3662-3672.

Wells, (1990), "Additivity of Mutational Effect in Proteins," *Biochemistry*, 29(37):8509-8517.

Wen et. al., (1993), "Erythropoietin Structure-Function Relationships: High Degree of Sequence Homology Among Mammals," *Blood*, 82(5):1507-1516.

Williams et. al., (1986), "Production of Antibody-tagged Enzymes by Myeloma Cells: Application to DNA Polymerase I Klenow Fragment," *Gene*, 43:319-324.

Williams et. al., (1987), "Diphtheria Toxin Receptor Binding Domain Substitution with Interleukin-2: Genetic Construction and Properties of a Diphtheria Toxin-related Interleukin-2 Fusion Protein," *Protein Engineering*, 1(6):493-498.

Wooley et. al., (1993), "Influence of a Recombinant Human Soluble Tumor Necrosis Factor Receptor Fc Fusion Protein on Type II Collagen-Induced Arthritis in Mice," *J. Immunology*, 151:6602-6607.

Wu et. al., (1997), "Suppression of Tumor Growth with Recombinant Murine Angiostatin," *Biochemical and Biophysical Research Communications*, 236:651-654.

Xiang et. al., (1997), "Elimination of Established Murine Colon Carcinoma Metastases by Antibody-Interleukin 2 Fusion Protein Therapy," *Cancer Research*, 57:4948-4955.

Xiang et. al., (1998), "Induction of Persistent Tumor-protective Immunity in Mice Cured of Established Colon Carcinoma Metastases," *Cancer Research*, 58(17):3918-3925.

Xiang et. al., (1999) "T Cell Memory against Colon Carcinoma is Long-lived in the Absence of Antigen," *J. Immunology*, 163(7):3676-83.

Xiang et. al., (2001), "A Dual Function DNA Vaccine Encoding Carcinoembryonic Antigen and CD40 Ligand Trimer Induces T Cell-mediated Protective Immunity Against Colon Cancer in Carcinoembryonic Antigen-Transgenic Mice," *J. Immunology*, 167(8):4560-5.

Xiang et. al., (2001), "Protective Immunity Against Human Carcinoembryonic Antigen (CEA) Induced by an Oral DNA Vaccine in CEA-transgenic Mice," *Clinical Cancer Research*, 7(3 Supp):S856-5864.

Xu et. al., (1994), "Residue at Position 331 in the IgGI and IgG4 CH2 Domains Contributes to Their Differential Ability to Bind and Activate Complement," *J. Biol. Chem.*, 269(5):3469-3474.

Yu et. al., (1998), "Phase I Trial of a Human-Mouse Chimeric Anti-Disaloganglioside Monoclonal Antibody ch14.18 in Patients with Refractory Neuroblastoma and Osteosarcoma," *J. Clinical Oncology*, 16(6):2169-80.

Zagozdzon et. al., (1999), "Potentiation of Antitumor Effects of IL-12 in Combination with Paclitaxel in Murine Melanoma Model In Vivo," *International Journal of Molecular Medicine*, 4:645-648.

Zheng et. al., (1995), "Administration of Noncytolytic IL-10/Fc in Murine Models of Lipopolysaccharide-induced Septic Shock and Allogenic Islet Transplantation," *J. Immunology*, 154:5590-5600.

Chapman et. al., (1994), "Mapping Effector Functions of a Monoclonal Antibody to GD3 by Characterization of a Mouse-Human Chimeric Antibody," *Cancer Immuno. Immunother.*, 39:198-204.

Cruse et. al., (eds.), (1995), *Illustrated Dictionary of Immunology*, p. 158, CRC Press, NY.

de la Salle et. al., (1996), "Fc-IR on Human Dendritic Cells," in *Human IgG Receptors*, pp. 39-55, van de Winkel et. al. (eds.), R.G. Landes Co.

Dorai et. al., (1991), "Aglycosylated Chimeric Mouse/Human IgG1 Antibody Retains Some Effector Function," *Hybridoma*, 10(2):211-217.

Dorai et. al., (1992), "Role of Inter-Heavy and Light Chain Disulfide Bonds in the Effector Functions of Human IgG1," *Molecular Immunology*, 29(12):1487-1491.

Elliott et. al., (1996), "Fine-Structure Epitope Mapping of Antierythropoietin Monoclonal Antibodies Reveals a Model of Recombinant Human Erythropoietin Structure," *Blood*, 87(7):2702-2713.

Gillies et. al., (1991), "Targeting Human Cytotoxic T Lymphocytes to Kill Heterologous Epidermal Growth Factor Receptor-Bearing Tumor Cells: Tumor-Infiltrating Lymphocyte/Hormone Receptor/Recombinant Antibody," *J. Immunology*, 146(3):1067-1071.

Handgretinger et. al., (1995), "A Phase I Study of Human/Mouse Chimeric Anti-ganglioside GD2 Antibody ch14.18 in Patients with Neuroblastoma," *European J.Cancer*, 31A(2):261-267.

Hurn et. al., (1980), "Production of Reagent Antibodies," *Methods in Enzymology*, 70: 104-142.

Isenman et. al., (1975), "The Structure and Function of Immunoglobulin Domains: II. The Importance of Interccain Disulfide Bonds and the Possible Role of Molecular Flexibility in the Interaction between Immunoglobulin G and Complement," *J. Immunology*, 114(6):1726-1729.

Lo et. al., (1992), "Expression and Secretion of an Assembled Tetrameric CH2-deleted Antibody in *E. Coli.*," *Hum. Antibod. Hybridomas*, 3:123-128.

Maecker et. al., (1997), "DNA Vaccination with Cytokine Fusion Constructs Biases the Immune Response to Ovalbumin," *Vaccine*, 15(15):1687-1696.

Mueller et. al., (1990), "Enhancement of Antibody-Dependent Cytotoxicity With A Chimeric Anti-GD2 Antibody," *J. Immunology*, 144(4):1382-1386.

Mueller et. al., (1990), "Serum Half-Life and Tumor Localization of a Chimeric Antibody Deleted of the CH2 Domain and Directed Against the Disialoganglioside GD2," *Proc. Natl. Acad. Sci. USA.*, 87:5702-5705.

Naramura et. al., (1993), "Therapeutic Potential of Chimeric and Murine Anit-(Epidermal Growth Factor Receptor~n ibodies in a Metastasis Model for Human Melanoma." *Cancer Immuno Immuno. Immunother.*, 37:343-349.

Reisfeld et. al., (1994), "Potential of Genetically Engineered Anti-Ganglioside GD2 Antibodies for Cancer Immunotherapy," *Prog. Brain Res.*, 101:201-212.

Saleh et. al., (1992), "Phase I Trial of the Chimeric Anti-GD2 Monoclonal Antibody ch14.18 in Patients With Malignant Melanoma," *Hum. Antiob. Hybridomas*, 3:19-24.

Sallusto et. al., (1994), "Efficient Presentation of Soluble Antigen by Cultured Human Dendritic Cells Is Maintained by Granulocyte/Macrophage Colony-stimulating Factor Plus Interleukin 4 and Downregulated by Tumor Necrosis Factor a," *J. Exp. Med.*, 179:1109-1118.

Schlom (1991), "Monoclonal Antibodies: They're More and Less Than You Think," in *Molecular Foundations of Oncology*, pp. 95-133.

Weber et. al., (2001), "Phase I Trial of huKS-IL2 Immunocytokine in Patients with Prostate Carcinoma: Clinical, PK, and Biological PD Results (Abstract)," *American Society of Clinical Oncology Program/Proceedings*, 20(Part 1):259a.

Wen et. al., (1994), "Erythropoietin Structure-Function Relationships: Identification of Functionally Important Domains," *J. Biological Chemistry*, 269(36):22839-22846.

International Preliminary Examination Report for International Application Serial No. PCT/US02/09815, mailed Nov. 28, 2003, 3 pages.

International Search Report for International Application Serial No. PCT/US02/09815, mailed Oct. 1, 2002, 2 pages.

Written Opinion for International Application Serial No. PCT/US02/09815, mailed Jun. 25, 2003, 4 pages.

Aichele et. al., (1994), "Peptide-Induced T-Cell Tolerance to Prevent Autoimmune Diabetes in a Transgenic Mouse Model," *Proc. Natl. Acad. Sci. USA*, 91:444-448.

Altschul et. al., (1990), "Basic Local Alignment Search Tool," *J. Mol. Biol.*, 215:403-10.

Altschul et. al., (1997), "Gapped BLAST and PSI-BLAST: A New Generation of Protein Database Search Programs," *Nucleic Acids Res.*, 25(17):3389-3402.

Anderson et. al., (1980), "Characterization of the Fc Receptor for IgG on a Human Macrophage Cell Line U937," *J. Immunol.*, 125(6):2735-41.

Anderson et. al., (1994), "Effects of Route and Formulation on Clinical Pharmacokinetics of Interleukin-2," *Clin. Pharmacokinet.*, 27(1):19-31.

Baici et. al., (1980), "Kinetics of the Different Susceptibilities of the Four Human Immunoglobulin G Subclasses to Proteolysis by Human Lysosomal Elastase," *Scand. J. Immunol.* 12(1):41-50.

Barbulescu et. al., (1998), "IL-12 and IL-18 Differentially Regulate the Transcriptional Activity of the Human IFN-y Promoter in Primary CD4+ T Lymphocytes," *J. Immunol.*, 160:3642-7.

Bednarek et. al., (1991), "Soluble HLA-A2.1 Restricted Peptides that are Recognized by Influenza Virus Specific Cytotoxic T Lymphocytes," *J. Immunol. Methods*, 139:41-47.

Benacerraf et. al., (1959), "The Clearance of Antigen Antibody Complexes from the Blood by the Reticulo-Endothelial System," *J. Immunol.*, 82:131-7.

Böhm, (1994), "On the Use of LUDI to Search the Fine Chemicals Directory for Ligands of Proteins of Known Three-Dimensional Structure," *J. Comput. Aided Mol. Des.*, 8:623-32.

Böhm, (1994), "The Development of a Simple Empirical Scoring Function to Estimate the Binding Constant for a Protien-Ligand Complex of Known Three-Dimensional Structure," *J. Comput. Aided Mol. Des.*, 8(3):243-56.

Böhm; (1998), "Prediction of Binding Constants of Protein Ligands: A Fast Method for the Prioritization of Hits Obtained from De Novo Design or 3D Database Search Programs," *J. Comput. Aided Mol. Des.*, 12(4):309-23.

Boshart et. al., (1985), "A Very Strong Enhancer is Located Upstream of an Immediate Early Gene of Human Cytomegalovirus," *Cell*, 41:521-530.

Boulianne et. al., (1984), "Production of Functional Chimaeric Mouse/Human Antibody," *Nature*, 312:643-6.

Bourgois et. al., (1974), "Determination of the Primary Structure of a Mouse IgG2a Immunoglobulin Amino Acid Sequence of the Fc Fragment: Implications for the Evolution of Immunoglobulin Structure and Function," *Eur. J. Biochem.*, 43:423-35.

Brambell et. al., (1964), "A Theoretical Model of y-Globulin Catabolism," *Nature*, 203:1352-55.

Brazolot Millan et. al., (1998), "Cpg DNA Can Induce Strong TH1 Humoral and Cell-Mediated Immune Responses against Hepatitis B Surface Antigen in Young Mice," *Proc. Natl. Acad. Sci. USA*, 95:15553-8.

Brekke et. al., (1994), "Human IgG Isotype-Specific Amino Acid Residues Affecting Complement-Mediated Cell Lysis and Phagocytosis," *Eur. J. Immunol.*, 24:2542-2547.

Brem et. al., (1993), "The Combination of Antiangiogenic Agents to Inhibit Primary Tumor Growth and Metastasis," *J. Pediatr. Surg.*, 28(10):1253-7.

Brocklebank et. al., (2001), "Enumeration of CD34+ Cells in Cord Blood: A Variation on a Single-Platform Flow Cytometric Method Based on the ISHAGE Gating Strategy," *Cytometry*, 46(4):254-61.

Brooks et. al., (1983), "CHARMM: A Program for Macromolecular Energy Minimization and Dynamics Calculations," *J. Comput. Chemistry*, 4:187-217.

Broudy et. al., (1988), "Recombinant Human Erythropoietin: Purification and Analysis of Carbohydrate Linkage," *Arch. Biochem. Biophys.*, 265:329-36.

Bubenik et. al., (1995), "Interleukin-2 Gene Therapy of Residual EL-4 Leukaemia Potentiates the Effect of Cyclophosphamide Pretreatment," *J. Cancer Res. Clin. Oncol.*, 121:39-43.

Bumol et. al., (1982), "Unique Glycoprotein-Proteoglycan Complex Defined by Monoclonal Antibody on Human Melanoma Cells," *Proc. Natl. Acad. Sci. USA*, 79:1245-9.

Carnemolla et. al., (1989), "A Tumor-Associated Fibronectin Isoform Generated by Alternative Splicing of Messenger RNA Precursors," *J. Cell. Biol.*, 108:1139-1148.

Carnemolla et. al., (1992), "The Inclusion of the Type III Repeat ED-B in the Fibronectin Molecule Generates Conformational Modifications that Unmask a Cryptic Sequence," *J. Biol. Chem.*, 267(34):24689-24692.

Casadevall et. al., (2002), "Pure Red-Cell Aplasia and Antierythropoietin Antibodies in Patients Treated with Recombinant Erythropoietin," *N. Engl. J. Med.*, 346(7):469-75.

Cazzola et. al., (1998), "Red Blood Cell Precursor Mass as an Independent Determinant of Serum Erythropoietin Level," *Blood*, 91:2139-45.

Chan et. al., (1992), "Mechanisms of IFN-y Induction by Natural Killer Cell Stimulatory Factor (NKSF/IL-12). Role of Transcription and mRNA Stability in the Synergistic Interaction Between NKSF and IL-2," *J. Immunol.*, 148:92-98.

Chappel et. al., (1991), "Identification of the Fc Gamma Receptor Class I Binding Site In Human IgG Through Use of Recombinant IgG1/IgG2 Hybrid and Point-Mutated Antibodies," *Proc. Natl. Acad. Sci. USA*, 88(20):9036-40.

Cheetham, (1998), "NMR Structure of Human Erythropoietin and a Comparison with its Receptor Bound Conformation," *Nat. Struct. Biol.*, 5:861-6.

Ciardiello et. al., (1996), "Antitumor Activity of Combined Blockade of Epidermal Growth Factor Receptor and Protein Kinase A," *J. Natl. Cancer Inst.*, 88:1770-6.

Cirulli et. al., (1998), "KSA Antigen Ep-CAM Mediates Cell-Cell Adhesion of Pancreatic Epithelial Cells: Morphoregulatory Roles in Pancreatic Islet Development," *J. Cell Biol.*, 140:1519-34.

Cohen et. al., (1998), "An Artificial Cell-Cycle Inhibitor Isolated from a Combinatorial Library," *Proc. Natl. Acad. Sci. USA*, 95:14272-7.

Congote et. al., (1984), The Erthrotropins, New Erythroid Cell Stimulate Factors Extracted From Human and Bovine Fetal Tissues, Abstract 364, "Proceedings 71' Intl. Congress of Endocrinology," Quebec City, Quebec, Jul. 1-7, 1984.

Congote, (1983), "Isolation of Two Biologically Active Peptides, Erythrotropin I and Erythrotropin II from Fetal Calf Intestine." *Biochem. Biophys. Res. Commun.*, 115(2):477-83.

Congote, (1984), "Extraction from Fetal Bovine Serum of Erythrotropin, an Erythroid Cell-Stimulating Factor," *Anal. Biochem.*, 140:428-33.

Connor et. al., (2004), "Ex vivo Evaluation of Anti-EpCAM Immunocytokine huKS-IL2 in Ovarian Cancer," *J. Immunotheraoy*, 27:211-219.

Cosenza et. al., (1997), "Disulfide Bond Assignment in Human Interleukin-7 by Matrix-Assisted Laser Desorption/Ionization Mass Spectroscopy and Site-Directed Cysteine to Serine Mutational Analysis," *J. Biol. Chem.*, 272:32995-3000.

Cunningham et. al., (1989), "High-Resolution Epitope Mapping of hGH-Receptor Interactions by Alanine-Scanning Mutagenesis," *Science*, 244:1081-85.

Curiel et. al., (1991), "Adenovirus Enhancement of Transferrin-Polylysine-Mediated Gene Delivery," *Proc. Natl. Acad. Sci. USA*, 88:8850-4.

Dauber-Osguthorpe et. al., (1988), "Structure and Energetics of Ligand Binding to Proteins: *Escherichia coli* Dihydrofolate Reductase-Trimethoprim, A Drug-Receptor System," *Proteins*, 4:31-47.

Daugherty et. al., (1991), "Polymerase Chain Reaction Facilities the Cloning, CDR-Grafting, and Rapid Expression of a Murine Monoclonal Antibody Directed Against the CD18 Component of Leukocyte Integrins," *Nucleic Acid Res.*, 19:2471-2476.

De Bruijn et. al., (1995), "Phagocyte-Induced Antigen-Specific Activation of Unprimed CD8+ T Cells in Vitro," *Eur. J. Immunol.*, 25:1274-85.

Delorme et. al., (1992), "Role of Glycosylation on the Secretion and Biological Activity of Erythropoietin," *Biochemistry*, 31:9871-6.

Desai et. al., (1992), "IL-12 Receptor. II. Distribution and Regulation of Receptor Expression," *J. Immunol.*

Donnelly et. al., (1993), "Targeted Delivery of Peptide Epitopes to Class I Major Histocompatibility Molecules by a Modified Pseudomonas Exotoxin," *Proc. Natl. Acad. Sci. USA*, 90:3530-4.

Donnelly et. al., (1997), "DNA Vaccines," *Annu. Rev. Immunol.*, 15:617-48.

Dube et. al., (1988), "Glycosylation at Specific Sites of Erythropoietin is Essential for Biosynthesis, Secretion, and Biological Function," *J. Biol. Chem.*, 263:17516-21.

Ellison et. al., (1982), "The Nucleotide Sequence of a Human Immunoglobulin C $\gamma_1$ Gene," *Nucleic Acids Res.*, 10:4071-9.

Faas et. al., (1993), "Phenotypically Diverse Mouse Thymic Stromal Cell Lines which Induce Proliferation and Differentiation Of Hematopoietic Cells," *Eur. J. Immunol.*, 23:1201-14.

Farner et. al., (1995), "Distinction Between yc C Detection and Function in YT Lymphoid Cells and in the Granulocyte-Macrophage Colony-Stimulating Factor-Responsive Human Myeloid Cell Line, Tf-1," *Blood*, 86:4568-78.

Fawell et. al., (1994), "Tat-Mediated Delivery of Heterologous Proteins into Cells," *Proc. Natl. Acad. Sci. USA*, 91:664-8.

Fu et. al., (1993), "The Sheep Erythropoietin Gene: Molecular Cloning and Effect of Hemorrhage on Plasma Erythropoietin and Renal/Liver Messenger RNA in Adult Sheep," *Mol. Cell. Endocrinol.*, 93:107-16.

Gainsford et. al., (1996), "Leptin Can Induce Proliferation, Differentiation, and Functional Activation of Hemopoietic Cells," *Proc. Natl. Acad. Sci. USA*, 93:14564-14568.

Gammon et. al., (1992), "Endogenous Loading of HLA-A2 Molecules with an Analog of the Influenza Virus Matrix Protein-Derived Peptide and Its Inhibition By An Exogenous Peptide Antagonist," *J. Immunol.*, 148:7-12.

Ghetie et. al., (1990), "Disseminated or Localized Growth of a Human B-Cell Tumor (Daudi) in SCID Mice," *Intl. J. Cancer*, 45:485.

Ghetie et. al., (1997), "FcRn: The MHC Class I-Related Receptor that is More Than an IgG Transporter," *Immunology Today*, 18(12):592-598.

Goldwasser et. al., (1971), "Purification of Erythropoietin," *Proc. Natl. Acad. Sci. USA*, 68:697-8.

Goldwasser et. al., (1975), "Brythropoeitin: Assay and Study of its Mode of Action," *Methods Enzymol.*, 37(PtB):109-21.

Gurewich et. al., (1988), "Characterization of the Intrinsic Fibrinolytic Properties of Pro-Urokinase Through a Study of Plasmin-Resistant Mutant Forms Produced by Site-Specific Mutagenesis of Lysine," *J. Clin. Invest.*, 82:1956-1962.

Halin et. al., (2002), "Enhancement of the Antitumor Activity of Interleukin-12 by Targeted Delivery to Neovasculature," *Nature Biotechnology*, 20:264-269.

Handgretinger et. al., (2001), "Immunological Aspects of Haploidentical Stem Cell Transplantation in Children," *Ann. NY Acad. Sci.*, 938:340-57.

Hashimoto et. al., (1999), "Differential Antitumor Effects of Administration of Recombinant IL-18 or Recombinant IL-12 are Mediated Primarily by Fas-Fas Ligand- and Perforin-Induced Tumor Apoptosis, Respectively," *J. Immunol.*, 163:583-9.

Henikoff et. al., (1992), "Amino Acid Substitution Matrices from Protein Blocks," *Proc. Natl. Acad. Sci. USA*, 89:10915-10919.

Hilgers et. al., (1999), "Sulfolipo-Cyclodextrin in Squalane-In-Water as a Novel and Safe Vaccine Adjuvant," *Vaccine*, 17:219-28.

Hori et. al., (1987), "Establishment of an Interleukin 2-Dependent Human T Cell Line from a Patient with T Cell Chronic Lymphocytic Leukemia Who is Not Infected with Human T Cell Leukemia/Lymphoma Virus," *Blood*, 70:1069-72.

Hulett et. al., (1994), "Molecular Basis of Fc Receptor Function," *Adv. Immunol.*, 57:1127.

Huston et. al., (1988), "Protein Engineering of Antibody Binding Sites: Recovery of Specific Activity in an Anti-Digoxin Single-Chain Fv Analogue Produced in *Escherichia coli*," *Proc. Natl. Acad. Sci. USA*, 85:5879-5883.

Jacobs et. al., (1985), "Isolation and Characterization of Genomic And cDNA Clones of Human Erythropoietin," *Nature*, 313:806-10.

Jefferis et. al., (1990), "Molcular Definition of Interaction Sites of Human IgG for Fc Receptors huFcyR," *Mol. Immunol.*, 27(12):1237-1240.

Karlin et. al., (1990), "Methods for Assessing the Statistical Significance of Molecular Sequence Features by Using General Scoring Schemes," *Proc. Natl. Acad. Sci. USA*, 87:2264-8.

Karlin et. al., (1993), "Applications and Statistics for Multiple High-Scoring Segments in Molecular Sequences," *Proc. Natl. Acad. Sci. USA*, 90:5873-7.

Karpusas et. al., (1997), "The Crystal Structure of Human Interferon P at 2.2-A Resolution," *Proc. Natl. Acad. Sci. USA*, 94:11813-11818.

Kelner et. al., (1994), "Lymphotactin: A Cytokine that Represents a New Class of Chemokine," *Science*, 266:1395-9.

Kirkman et. al., (1989), "Prolongation of Cardiac Allograft Survival in Murine Recipients Treated with a Diphtheria Toxin-Related Interleukin-2 Fusion Protein," *Transplantation*, 47(2):327-330.

King et. al., (2004), "Phase I Clinical Trial of the Immunocytokine EMD 273063 in Melanoma Patients," *J. Clin. Oncol.*, 22(22):4463-73.

Klinman et. al., (1997), "Contribution of CpG Motifs to the Immunogenicity of DNA Vaccines," *J. Immunol.*, 158:3635-9.

Ko et. al., (2004), "Safety, Pharmacokinetics, and Biological Pharmacodynamics of the Immunocytokine EMD 273066 (huKS-IL2)," *J. Immunotherapy*, 27:232-239.

Kuntz et. al., (1982), "A Geometric Approach to Macromolecule-Ligand Interactions," *J. Mol. Biol.*, 161:269-88.

Kurtz, (1982), "A New Candidate for the Regulation of Erythropoietis. Insulin-Like Growth Factor I," *FEBLAL.*, 149(1):105-8.

Lai et. al., (1986), "Structural Characterization of Human Erythropoietin," *J. Biol. Chem.*, 261:3116-21.

Lai et. al., (1998), "DNA Vaccines," *Crit. Rev. Immunol.*, 18:449-84.

Lanza et. al., (1993), "Active Immunity against the CD4 Receptor by Using an Antibody Antigenized with Residues 41-55 of the First Extracellular Domain," *Proc. Natl. Acad. Sci. USA*, 90:11683-7.

Lawn et. al., (1981), "DNA Sequence of a Major Human Leukocyte Interferon Gene," *Proc. Natl. Acad. Sci. USA*, 78:5435-9.

Lin et. al., (1985), "Cloning and Expression of the Human Erythropoietin Gene," *Proc. Natl. Acad. Sci. USA*, 82:7580-4.

Lin et. al., (1986), "Monkey Erythropoietin Gene: Cloning, Expression and Comparison with the Human Erythropoietin Gene," *Gene*, 44:201-9.

Lode et. al., (1998), "Gene Therapy with a Single Chain Interleukin 12 Fusion Protein Induces T Cell-Dependent Protective Immunity in a Syngeneic Model of Murine Neuroblastoma," *Proc. Natl. Acad. Sci. USA*, 95:2475-80.

Lorenz et. al., (1999), "Induction of Anti-Tumor Immunity Elicited by Tumor Cells Expressing a Murine LFA-3 Analog Via a Recombinant Vaccinia Virus," *Hum. Gene Ther.*, 10:623-31.

Lotze et. al., (1996), "Cytokine Gene Therapy of Cancer Using Interleukin-12: Murine and Clinical Trials," *Ann. NY Acad. Sci.*, 795:440-54.

MacLean et. al., (1996), "Enhancing the Effect of Theratope STn-KLH Cancer Vaccine in Patients with Metastatic Breast Cancer by Pretreatment with Low-Dose Intravenous Cyclophosphamide," *J. Immunother.*, 19(4):309-316.

Maghazachi et. al., (1997), "Interferon-Inducible Protein-10 and Lymphotactin Induce the Chemotaxis and Mobilization of Intracellular Calcium in Natural Killer Cells through Pertussis Toxin-Sensitive and -Insensitive Heterotrimeric G-Proteins," *FASEB J.*, 11:765-74.

Maloy et. al., (2001), "Regulatory T Cells in the Control of Immune Pathology," *Nature Immunol.*, 2:816-22.

Mariani et. al., (1997), "Tumor Targeting Potential of the Monoclonal Antibody BC-1 against Oncofetal Fibronectin in Nude Mice Bearing Human Tumor Implants," *Cancer*, 80:2378-84.

Marshall et. al., (1994), "Role of the Polymorphic Residues in HLA-DR Molecules in Allele-Specific Binding of Peptide Ligands," *J. Immunol.*, 152:4946-57.

Marshall et. al., (1995), "Prediction of Peptide Affinity to HLA-DR Molecules," *Biomed. Pept. Proteins Nucleic Acids*, 1(3):157-62.

Martin et. al., (2001), "Crystal Structure at 2.8 A of an FcRn/Heterodimeric Fc Complex: Mechanism of pH-Dependent Binding," *Mol. Cell.*, 7(4):867-77.

McDonald, (1986), "Cloning, Sequencing, and Evolutionary Analysis of the Mouse Erythropoietin Gene," *Mol. Cell. Biol.*, 6:842-8.

McGonigle et. al., (1984), "Erythropoietin Deficiency and Inhibition of Erythropoiesis in Renal Insufficiency," *Kidney Int.*, 25(2):437-44.

McMahan et. al., (1991), "A Novel IL-1 Receptor, Cloned From B-Cells by Mammalian Expression is Expressed in Many Cell Types," *EMBO J.*, 10:2821-32.

McMahon et. al., (1990), "Pharmacokinetics and Effects of Recombinant Human Erythropoietin after Intravenous and Subcutaneous Injections in Healthy Volunteers," *Blood*, 76:1718-22.

Mehrotra et. al., (1993), "Effects of IL-12 on the Generation of Cytotoxic Activity in Human CD8+ T Lymphocytes," *J. Immunol.*, 151:2444-52.

Menard et. al., (1983), "Generation of Monoclonal Antibodies Reacting with Normal and Cancer Cells of Human Breast," *Cancer Res.*, 43:1295-300.

Miyake et. al., (1977), "Purification of Human Erythropoietin," *J. Biol. Chem.*, 252:5558-64.

Miyake et. al., (1988), "Synthesis of Recombinant Human Single-Chain Urokinase-Type Plasminogen Activator Variants Resistant to Plasmin and Thrombin," *J. Biochem.*, 104:643-647.

Morrison et. al., (1984), "Chimeric Human Antibody Molecules: Mouse Antigen-Binding Domains with Human Constant Region Domains," *Proc. Natl. Acad. Sci. USA*, 81:6851-5.

Nagao et. al., (1992), "Nucleotide Sequence of Rat Erythropoietin," *Biochim. Biophys. Acta*, 1171(1):99-102.

Nastala et. al., (1994), "Recombinant IL-12 Administration Induces Tumor Regression in Association with IFN-r Production," *J. Immunol.*, 153:1697-706.

Naughton et. al., (1983), "Evidence for an Erythropoietin-Stimulating Factor in Patients with Renal and Hepatic Disease," *Acta. Haemat.*, 69:171-9.

Neal et. al., (2004), "Enhanced Activity of Hu14.18-IL2 Immunocytokine against Murine NXS2 Neuroblastoma when Combined with Interleukin-2 Therapy," *Clin. Cancer. Res.*, 10:4839-4847.

Nelles et. al., (1987), "Characterization of Recombinant Human Single Chain Urokinase-Type Plaminogen Activtor Mutants Produced by Site-Specific Mutagenesis of Lysine 158," *J. Biol. Chem.*, 262(12):5682-5689.

Noguchi et. al., (1994), "A Mouse Mutant P53 Product Recognized by CD4+ and CD8+ T Cells," *Proc. Natl. Acad. Sci. USA*, 91:3171-5.

Orlandi et. al., (1989), "Cloning Immunoglobulin Variable Domains for Expression by the Polymerase Chain Reaction," *Proc. Natl. Acad. Sci. USA*, 86:3833-7.

Palmer et. al., (2001), "Phase I Study of the BLP 25 (MUCI Peptide) Liposomal Vaccine for Active Specific Immunotherapy in Stage IIIB/IV Non-Small-Cell Lung Cancer," *Clinical Lung Cancer*, 3(1):49-57.

Palucka et. al., (1998), "Dendritic Cells as the Terminal Stage of Monocyte Differentiation," *J. Immunol.*, 160:4587-95.

Panina-Bordignon et. al., (1989), "Universally Immunogenic T Cell Epitopes: Promiscuous Binding to Human MHC Class II and Promiscuous *Recognition* by T Cells," *Eur. J. Immunol.*, 19:2237-42.

Pavlović-Kentera et. al., (1980), "Effects of Prostaglandin Synthetase Inhibitors, Salt Overload and Renomedullary Dissection on the Hypoxia Stimulated Erythropoietin Production in Rats," *Exp. Hematol.*, 8(Supp. 8):283-92.

Pedley et. al. (1999), "Enhancement of Antibody-Directed Enzyme Prodrug Therapy in Colorectal Xenografts by an Antivascular Agent," *Cancer Res.*, 59:3998-4003.

Perussia et. al., (1992), "Natural Killer (NK) Cell Stimulatory Factor or IL-12 Has Differential Effects on the Proliferation of TCR-ap+, TCR-yS+ T Lymphocytes, and NK Cells," *J. Immunol.*, 149:3495-502.

Pluschke et. al., (1996), "Molecular Cloning of a Human Melanoma-Associated Chondroitin Sulfate Proteoglycan," *Proc. Natl. Acad. Sci. USA*, 93:9710-5.

Poon et. al., (1995), "Structure and Function of Several Anti-Dansyl Chimeric Antibodies Formed by Domain Interchanges Between Human IgM and Mouse IgG2b," *J. Biol. Chem.*, 270:8571-7.

Queen et. al., (1989), "A Humanized Antibody that Binds to the Interleukin 2 Receptor," *Proc. Natl. Acad. Sci. USA*, 86:10029-33.

Radhakrishnan et. al., (1996), "Zinc Mediated Dimer of Human Interferon-alb Revealed by X-Ray Crystallography," *Structure* 4(12):1453-63.

Ramachandran et. al., (1968)"Conformation of Polypeptides and Proteins," *Adv. Prot. Chem.*, 23:283-294.

Rarey et. al., (1995), "Time-Efficient Docking of Flexible Ligands into Active Sites Of Proteins," *Proc. Int. Conf. Intell. Syst. Mol. Biol.* 3:300-8.

Resegotti et. al., (1981), "Treatment of Aplastic Anaemia with Methenolone, Stanozolol and Nandrolone. A Report of 130 Cases," *Pan. Med.*, 23:243-8.

Riechmann et. al., (1988), "Reshaping Human Antibodies for Therapy," *Nature*, 332:323-7.

Robinson et. al., (1998), "Optimizing the Stability of Single-Chain Proteins by Linker Length and Composition Mutagenesis," *Proc. Natl. Acad. Sci. USA*, 95:5929-34.

Rothmann et. al., (1982), "Brythropoietin-Dependent Erythrocytosis associated with Hepatic Angiosarcoma," *J. Surg. Oncol.*, 20:105-8.

Runkel et. al., (1998), "Structural and Functional Differences Between Glycosylated and Non-Glycosylated Forms of Human Interferon-8 (IFN-R)," *Pharmaceutical Res.*, 15:641-649.

Sakano et. al., (1980), "Two Types of Somatic Recombination are Necessary for the Generation of Complete Immunoglobin Heavy-Chain Genes," *Nature*, 286:676-683.

Sali et. al., (1993), "Comparative Protein Modelling by Satisfaction of Spatial Restraints," *J. Mol. Biol.*, 234:779-815.

Schecter et. al., (1997), "Tissue Factor is Induced by Monocyte Chemoattractant Protein-1 in Human Aortic Smooth Muscle and THP-1 Cells," *J. Biol. Chem.*, 272:28568-73.

Senior et. al., (2000), "Cleavage of a Recombinant Human Immunoglobulin A2 (igA2)-IgA1 Hybrid Antibody by Certain Bacterial IgA1 Proteases," *Infect. Immun.*, 68(2):463-9.

Sharp et. al., (1988), "Codon Usage Patterns in *Escherichia coli, Bacillus subtilis, Saccharomyces cerevisiae, Schizosaccharonryces pombe, Drosophila melanogaster* and *Homo sapiens*; a Review of the Consdierable Within-Species Diversity," *Nucleic Acids Res.*, 16(17):8207-8211.

Simonsen et. al., (1983), "Isolation and Expression of an Altered Mouse Dihydrofolate Reductase cDNA," *Proc. Natl. Acad. Sci. USA*, 80:2495-2499.

Smith et. al., (1981), "Identification of Common Molecular Subsequences," *J. Mol. Biol.*, 147:195-197.

Soligo et. al., (1998), "Expansion of Dendritic Cells Derived from Human CD34+ Cells in Static And Continuous Perfusion Cultures," *Br. J. Haematol.*, 101:352-63.

Spivak et. al., (1989), "The In Vivo Metabolism of Recombinant Human Erythropoietin in The Rat," *Blood*, 73:90-9.

Sturniolo et. al., (1999), "Generation of Tissue-Specific and Promiscuous HLA Ligand Databases Using DNA Microarrays and Virtual HLA Class II Matrices," *Nat. Biotech.*, 17(6):555-61.

Suliman et al., (1996), "Cloning of a cDNA Encoding Bovine Erythropoietin and Analysis of Its Transcription in Selected Tissues," *Gene*, 171:275-80.

Takahashi et al., (2000), "Immunologic Self-Tolerance Maintained by CD25+ CD4+ Regulatory T Cells Constitutively Expressing Cytotoxic T Lymphocyte-Associated Antigen 4," *J. Exp. Med.*, 192(2):303-309.

Takai, (2002), "Roles of Fc Receptor-s-in-Autoimmunity" *Nat. Rev. Immunol.*, 2(8):580-92.

Taniguchi et al., (1980), "Expression of the Human Fibroblast Interferon Gene in *Escherichia coli*," *Proc. Natl. Acad. Sci. USA*, 77:5230-5233.

Thurner, (1999), "Generation of Large Numbers of Fully Mature and Stable Dendritic Cells from Leukapheresis Products for Clinical Application," *J. Immunol. Methods*, 223:1-15.

Tiruppathi et al., (1996), "Isolation and Characterization of a Cell Surface Albumin-Binding Protein from Vascular Endothelial Cells," *Proc. Nat. Acad. Sci. USA*, 93:250-4.

Van Den Eynde et al., (1989), "Presence on a Human Melanoma of Multiple Antigens Recognized By Autologous CTL," *Int. J. Cancer*, 44:634-40.

Van Der Bruggen et al., (1991), "A Gene Encoding an Antigen Recognized by Cytolytic T Lymphocytes on a Human Melanoma," *Science*, 254:1643-7.

Van Heyningen et al., (1982), "Human MHC Class II Molecules as Differentiation Markers," *Immunogenetics*, 16:459-69.

Voest et al., (1995), "Inhibition of Angiogenesis in Vivo by Interleukin 12," *J. Natl. Canc. Inst.*, 87:581-6.

Von Heijne et al., (1986), "A New Method for Predicting Signal Sequence Cleavage Sites," *Nucleic Acid Res.*, 14:4683-4690.

Ward et al., (1995), "The Effector Functions of Immunoglobulins: Implications for Therapy," *Therapeutic. Immunology*, 2:77-94.

Watson et al., (1984), "Compilation of Published Signal Sequences," *Nucleic Acid Res.*, 12:5145-5164.

Weitkamp et al., (1973), "Additional Data on the Population Distribution of Human Serum Albumin Genes; Three New Variants," *Ann. Hum. Genet.*, 37:219-26.

Wetzel et. al., (2001), "BAY50-4798, an Interleukin-2 (IL—2) Variant, Demonstrates Selective Activation of Human and Chimpanzee T Cells Relative to NK Cells but Shows Less Selectivity for T Cells from Monkeys and Rodents," *ASCO 2001 Annual Meeting*, Abstract #1051.

Woof et al., (1986), "Localisation of the Monocyte-Binding Region on Human Immunoglobulin G," *Mol. Immunol.*, 23:319-30.

Wyatt et al., (1998), "The Antigenic Structure of the HIV gp120 Envelope Glycoprotein," *Nature*, 393:705-11.

Wysocka et al., (1995), "Interleukin-12 is Required for Interferon-y Production and Lethality in Lipopolysaccharide-Induced Shock in Mice," *Eur. J. Immunol.*, 25:672-6.

Yan et al., (1996), "Characterization of an IgVH Idiotope that Results in Specific Homophilic Binding and Increased Avidity for Antigen," *J. Immunol..*, 157:1582-8.

Yeh et al., (1992), "Design of Yeast-Secreted Albumin Derivatives for Human Therapy: Biological and Antiviral Properties of a Serum Albumin-CD4 Genetic Conjugate," *Proc. Natl. Acad. Sci. USA*, 89:1904-8.

Zhang et al., (1994), "Structure/Activity Analysis of Human Monocyte Chemoattractant Protein-1 (MCP-1) by Mutagenesis," *J. Biol. Chem.*, 269:15918-24.

Zhu et al., (2001), "MHC Class I-Related Neonatal Fc Receptor for IgG is Functionally Expressed in Monocytes, Intestinal Macrophages and Dendritic Cells," *J. Immunol.*, 166:3266-3276.

Zuckier et al., (1988), "Chimeric Human-Mouse IgG Antibodies with Shuffled Constant Region Exons Demonstrate that Multiple Domains Contribute to In Vivo Half-Life," *Cancer Res.*, 58(17):3905-8.

Isaacs et al., (1998), "Therapy with Monoclonal Antibodies," *J. Immunol.*, 161:3862-3869.

\* cited by examiner

REDUCING THE IMMUNOGENICITY OF FUSION PROTEINS

RELATED APPLICATIONS

This application is a divisional application of U.S. patent application Ser. No. 10/112,582, filed Mar. 29, 2002, which claims priority to and the benefit of U.S. provisional patent application 60/280,625, filed Mar. 30, 2001, the entire disclosures of which are incorporated herein by reference.

FIELD OF THE INVENTION

The present invention relates generally to methods and compositions for making and using modified fusion proteins with reduced or no immunogenicity as therapeutic agents. More specifically, the invention relates to fusion proteins, made less immunogenic by identifying candidate T-cell epitopes and modifying the amino acid sequence to eliminate such epitopes.

BACKGROUND OF THE INVENTION

Many therapeutic proteins are normal human proteins. For example, interleukin-2, erythropoietin, and growth hormone are all human proteins that are given to humans who already usually make endogenous levels of these proteins. In general, immune responses against completely normal human proteins are rare when these proteins are used as therapeutics.

Recently it has become apparent that many fusion proteins with artificial activities are useful as therapeutic proteins. For example, Enbrel is a fusion of the extracellular domain of a TNF receptor with an IgG1 Fc region. Enbrel is used to treat rheumatoid arthritis, and is thought to function by titrating TNF and preventing TNF action. However, a significant incidence of anti-Enbrel antibodies have been noted in patients treated with Enbrel.

Another example of a therapeutically useful class of fusion proteins is the immunocytokines. These proteins include an antibody moiety and a cytokine moiety, and are useful for targeting cytokines to diseased cells, such as cancer cells. However, the therapeutic use of many of these fusion proteins is curtailed due to their immunogenicity in mammals, especially humans.

Therefore, there is a need to generate fusion proteins with reduced immunogenicity in order to use these proteins in therapy.

SUMMARY OF THE INVENTION

The present invention features methods and compositions useful for producing fusion proteins with reduced immunogenicity for use in therapy. For example, the invention features immunocytokines, immunofusins, immunoligands, other antibody and Fc fusion proteins, cytokine-cytokine fusion proteins, and albumin fusion proteins with decreased immunogenicity.

The invention relates in part to the insight that fusion proteins contain sequences that are "non-self." For example, even in a fusion between two human proteins, the region surrounding the fusion junction comprises a peptide sequence that is not normally present in the human body. For example, a protein drug such as Enbrel is derived from two normal human proteins: TNF receptor and IgG1. However, the junction between TNF receptor and IgG1 is a peptide sequence that is not normally found in the human body.

Preferred methods of the invention involve reducing the immunogenicity of a fusion protein by reducing the ability of a junctional epitope (junctional peptide) to interact with a T-cell receptor by reducing its ability to bind (its binding affinity) to MHC molecules. According to the invention, the junctional epitope or peptide is preferably "non-self." In general, proteins, including therapeutic proteins, are immunogenic, in part because proteins are endocytosed by antigen-presenting cells and proteolyzed, and the resulting peptides bind to molecules called major histocompatibility complex (MHC) that present the peptides to T cells. The antigenic peptide-MHC complex on the surface of an antigen presenting cell (APC) activates T-cells to proliferate, differentiate and release cytokines. In parallel, B-cell differentiation and antibody production is induced which may further limit the therapeutic protein's effectiveness due to clearance. Thus, the antigenic peptide, if derived from a therapeutic protein, is capable of inducing a series of undesired immune responses. The therapeutic protein's effectiveness is limited due to titration by antibodies, and the induction of T-cell and B-cell responses is often deleterious due to inflammatory and allergic reactions in the patient.

The invention provides (1) the identification of novel amino acid sequences in the region of the immunoglobulin-target protein junction with one or more candidate T-cell epitopes; and (2) the modification of these amino acid sequences to reduce or eliminate the presence of peptides, derived from the junction sequence, that function as T-cell epitopes.

The invention provides two general classes of compositions and methods relating to the reduction of immunogenicity. According to one embodiment of the invention, potential non-self T-cell epitopes are identified in sequences that span a fusion junction. For example, potential non-self T-cell epitopes are identified by computational methods based on modeling peptide binding to MHC Class II molecules. Substitutions are then made such that the ability of peptides deriving from the junction region to bind to MHC Class II is reduced or eliminated. This process of identifying and modifying peptides which bind to MHC Class II is termed "de-immunization" and the resultant modified protein molecules are termed "de-immunized."

According to another embodiment of the invention, one or more glycosylation sites is introduced at a fusion junction. An N-linked glycosylation site is preferably used, although an O-linked glycosylation site may also be used. According to a preferred embodiment, amino acids in a junction region surrounding a fusion junction of wild-type sequence are mutated such that the last amino acid of the N-terminal fusion partner is mutated to an asparagine, and the first two amino acids of the second fusion partner are mutated to a glycine followed by a serine or a threonine.

According to the invention, removal of MHC Class II binding is preferred in situations where a protein is to be produced in bacteria or in an organism that does not generate a mammalian glycosylation pattern, such as yeast or insect cells.

The introduction of glycosylation sites may be preferred when the protein is to be produced in a mammalian cell line or in a cell line that creates a glycosylation pattern that is innocuous to mammals.

In a preferred embodiment, a component of the fusion protein is a cytokine. The term "cytokine" is used herein to describe naturally occurring or recombinant proteins, analogs thereof, and fragments thereof that elicit a specific response in a cell that has a receptor for that cytokine. Preferably, cytokines are proteins that may be produced and excreted by a cell.

Preferably, cytokines include interleukins such as interleukin-2 (IL-2), IL-3, IL-4, IL-5, IL-6, IL-7, IL-10, IL-12, IL-13, IL-14, IL-15, IL-16 and IL-18, hematopoietic factors such as granulocyte-macrophage colony stimulating factor (GM-CSF), G-CSF and erythropoietin, tumor necrosis factors (TNF) such as TNFα, lymphokines such as lymphotoxin, regulators of metabolic processes such as leptin, and interferons such as interferon α, interferon β, and interferon γ and chemokines. Preferably, the antibody-cytokine fusion protein of the present invention displays a cytokine specific biological activity.

In another preferred embodiment, a component of the fusion protein is an anti-obesity cytokine. For example, a component is leptin, CNTF, or a portion of Acrp30.

In an alternative preferred embodiment, a component of the fusion protein is a hormone. For example, a component may be insulin, growth hormone, or glucagon-like peptide 1 (GLP-1).

In yet another alternative embodiment, a component of the fusion protein is a ligand-binding protein with biological activity. In a preferred embodiment, an extracellular domain of TNF receptor is used.

According to one series of embodiments, a fusion protein of the invention comprises the N-terminus of a non-antibody moiety fused to the C-terminus of an antibody moiety. According to another series of embodiments, a fusion protein of the invention comprises the C-terminus of a non-antibody moiety fused to the N-terminus of an antibody moiety. According to the invention, an antibody moiety can be an intact immunoglobulin or a portion of an intact immunoglobulin. A portion of an immunoglobulin can include a variable region or a constant region or both. Preferred immunoglobulins include Fc regions or portions thereof. A preferred embodiment of the invention includes an IgG1 immunoglobulin isotype, or a portion thereof, modified to be less immunogenic and/or to have a longer serum half-life. For example, an IgG1 with modification of amino acid residues near the CH3-cytokine junction is preferred. For certain applications, antibody moieties from IgG2 or IgG4 isotypes are preferred.

Immunocytokines are only one example of a tumor-targeted fusion protein therapy. Other tumor-toxic molecules can also be targeted to tumors by fusion to tumor-specific antibodies. In addition, antibody fusion proteins can attack other types of diseased cells, such as virus-infected cells. Another approach to engineering targeted fusion proteins has been use of Fc-X and X-Fc technology where X is a polypeptide. These technologies utilize the knowledge that production and collection of a target protein is improved if the polypeptide of interest is linked to the Fc portion of an immunoglobulin. For Fc-X fusion proteins, a signal peptide, followed by the Fc fragment of an immunoglobulin gene is the N-terminal fusion partner to the target protein. In some instances it is specifically advantageous to engineer a fusion protein in the X-Fc orientation. With these constructs the target protein is the N-terminal fusion protein and the Fc fragment follows. For some proteins this approach is useful, as has been shown with lymphocyte cell surface glycoprotein (LHR) (U.S. Pat. No. 5,428,130), and glucagon-like peptide (GLP-1).

Accordingly, methods and compositions of the invention provide forms of Fc-X and X-Fc fusion proteins with reduced-immunogenicity. According to the invention, the immunogenicity of a fusion protein can be assayed according to a method known in the art or disclosed herein.

Methods and compositions of the invention also provide albumin fusion proteins with reduced immunogenicity. Human serum albumin (HSA), due to its remarkably long half-life, its wide in vivo distribution and its lack of enzymatic or immunological functions, has been used as a carrier for therapeutic peptides/proteins (Yeh et al, PNAS 89:1904-1908, 1992). A genetic fusion of a bioactive peptide to HSA is useful for recovery of a secreted therapeutic HSA derivative. However, according to the invention, albumin fusion proteins such as HSA-CD4 have a novel junction which generally contains one or more T-cell epitopes capable of being presented on MHC class II molecules. The invention provides less immunogenic forms of albumin fusion proteins, and general methods for reducing the immunogenicity of albumin fusion proteins. According to the invention, useful albumin proteins include species, allelic, and mutant variants of albumin, including fragments thereof. Preferred albumin proteins retain the structural and functional properties of a wild-type albumin protein such as HSA.

In another aspect, the invention provides de-immunized antibody fusion proteins with normal, mutant, or hybrid isotypes that comprise useful mutations. These mutations may be near the junction or at positions distinct from the region of the junction.

For example, the invention provides a de-immunized immunocytokine, modified at the junction, with a point mutation at the junction between the IgG and non-IgG moieties. The cytokine moiety includes any cytokine but preferably IL-2 or IL-12. In one embodiment, the amino acid changes involve changing the C-terminal lysine of the antibody moiety to a hydrophobic amino acid such as alanine or leucine. A key advantage of combining such mutations with a de-immunizing modification of the invention is that the mutations act together to increase serum half-life and to decrease immunogenicity. The methods described herein for combining de-immunization of a fusion junction with a serum-half-life altering mutation are useful to improve significantly the clinical efficacy of these fusion proteins.

In another aspect, the invention provides immunocytokines comprising a hybrid antibody moiety that includes domains from different Ig isotypes, preferably from both IgG1 and IgG2 isotypes, and a de-immunizing modification at the fusion junction. For example, the invention provides a de-immunized, junction-modified immunocytokine using an IgG2 and an IgG2h hybrid (IgG2 modified in the hinge region to IgG1). In a preferred embodiment, the hybrid fusion protein consists of a de-immunized immunoglobulin moiety composed of an IgG (γ1:CH1-H)(γ2:CH2-CH3) and a cytokine moiety.

In another aspect, the invention provides novel nucleic acid sequences that encode fusion proteins with reduced immunogenicity or facilitate the expression, production, and secretion of fusion proteins with reduced immunogenicity. Such nucleic acids are generated according to standard recombinant DNA techniques.

In a preferred embodiment, a nucleic acid molecule encodes an immunocytokine fusion protein. A preferred immunocytokine includes a cytokine, for example, Interleukin 2, and a tumor specific monoclonal antibody such as an antibody to human epithelial cell adhesion molecule KSA (EP-CAM)(huKS).

In another preferred embodiment, nucleic acid molecules encode Fc fusion proteins in various configurations. The nucleic acid molecule encodes serially in a 5' to 3' direction, (i) a signal sequence, an immunoglobulin Fc region and a target protein sequence or (ii) a signal sequence, a target protein, and an immunoglobulin Fc region, or (iii) a signal sequence, a first target protein, an immunoglobulin Fc region, and a second target protein. The resulting nucleic acid molecule thereby encodes an Fc-X, X-Fc, or X-Fc-Y structure where X and Y are a target protein. In an alternative embodiment, a nucleic acid encodes an Fc-X, X-Fc, or X-Fc-Y protein without a signal sequence.

In another preferred embodiment, a nucleic acid of the invention encodes an Ig fusion protein with mutant or hybrid isotypes. Specifically, the nucleic acid provides antibody moieties with hybrid isotypes, or alternatively with altered hinge regions. For example, the fusion protein consists of an IgG2, modified to contain fewer disulfide bonds in the hinge region, or an IgG2 CH2 and CH3 region in which the hinge region derives from another antibody, preferably a normal or mutant IgG1 hinge region.

A nucleic acid of the invention is preferably incorporated in operative association into a replicable expression vector which is then introduced into a mammalian host cell competent to produce the fusion protein. The resultant fusion protein is produced efficiently and secreted from the mammalian host cell. The secreted fusion protein is subsequently collected from the culture media without lysing the mammalian host cell. The protein product is assayed for activity and/or purified using common reagents as desired, and/or cleaved from the fusion partner, all using conventional techniques.

Thus, the invention also provides methods for producing fusion proteins with reduced immunogenicity.

Methods and compositions of the invention are also useful to provide therapeutic treatment using a fusion protein that has been rendered less immunogenic. An overall object of the invention is to provide processes that are both efficient and inexpensive as well as proteins that are less immunogenic. Preferred therapeutic compositions of the invention include a therapeutically effective amount of de-immunized fusion protein. Preferably, the de-immunized fusion protein is administered along with a pharmaceutically acceptable carrier.

The foregoing and other aspects, features and advantages of the present invention will be made more apparent from the detailed description, drawings, and claims that follow.

DETAILED DESCRIPTION OF THE INVENTION

All proteins, including antibodies, that are administered to a patient for therapeutic use have the potential to induce an immune response in the recipient host. This immune response is mediated by T-lymphocytes (T-cells) which then trigger B-lymphocytes (B-cells) to make antibodies. Antibody production against the therapeutic agent is detrimental since it leads to more rapid elimination of the therapeutic agent and may induce an allergic response.

The present invention provides methods of reducing the immunogenicity of fusion proteins. According to one method of this invention, potential T-cell epitopes are identified in the junction region of a fusion junction in a fusion protein. T-cell epitopes are identified by a variety of computer and non-computer methods, including prediction based on structure-based computer modeling or by synthesis of peptides and testing for binding to specific MHC Class II molecules or in an immunogenicity assay.

According to the invention, a fusion junction is defined as the position between the last (C-terminal) amino acid of a first protein or peptide and the first (N-terminal) amino acid of a second protein or peptide in a fusion protein. Accordingly, a fusion junction includes any amino acids between the last amino acid of one protein and the first amino acid of a second protein. In one embodiment, the fusion junction includes a linker.

According to the invention, a junction region is the region of a fusion protein surrounding or spanning the fusion junction between two proteins. A junction region preferably includes between 1 and about 100 amino acids, more preferably between 1 and about 50 amino acids, or between 1 and about 25 amino acids, and even more preferably between 1 and about 15 amino acids, or between 1 and 9 amino acids. In one embodiment, a junction region comprises a spacer or linker peptide inserted at the junction point between the two proteins. According to the invention, a junction region including a spacer or linker peptide can also be de-immunized to minimize the response of a patient to a fusion protein including the spacer or linker.

According to the invention, a junctional T-cell epitope is defined as a peptide sequence capable of binding an MHC Class II containing at least one amino acid derived from each of at least two different fusion partner proteins. For example, Paul (*Fundamental Immunology*, Chapter 8, Table 8, p. 276 [2000] 4$^{th}$ ed.) illustrates segments of 10 amino acids that can bind to an MHC Class II molecule. In a junctional T-cell epitope, these 10 amino acid peptides are derived from different fusion partners. According to the invention a potential or candidate T-cell epitope that spans a fusion junction (a candidate junctional T-cell epitope) preferably includes 1 to 8 amino acids from either side of the junction, and more preferably 1 to 10 or 1 to 11 amino acids from either side of the junction. Candidate epitopes are preferably 9, 11, or 12 amino acids long. Accordingly, since a junctional T-cell epitope of the invention includes at least one amino acid from each side of the junction, preferred candidate T-cell epitopes are junctional epitopes that include 1-8 (or 1-10, or 11) amino acids from one side of the junction and also include a complementary number of amino acids from the other side of the junction to result in an epitope having 9-12 amino acids, and most preferably 9 amino acids.

According to the invention, anchor residues within a junctional T-cell epitope are then mutated to prevent binding to an MHC Class II molecule. In general, care is taken to not introduce additional potential T-cell epitopes, and to preserve the function of each fusion partner.

According to the invention, a fusion of wild-type sequences is a fusion in which the sequences at the N-terminal and C-terminal sides of the fusion junction are derived directly from naturally occurring sequences.

According to the invention, a de-immunized fusion junction is a junction sequence in which one or more substitution mutations have been introduced relative to a junction of wild-type sequences. In a most preferred embodiment, deimmunization of a fusion junction does not involve introduction of a linker, such as a 'non-immunogenic' Gly-Ser linker, and the spatial relationship between the fusion partners is not altered in a de-immunized fusion protein. According to the invention, one or more amino acids can be substituted or changed in the junction region either N-terminally to the fusion junction, C-terminally to the fusion junction, or both N-terminally and C-terminally to the fusion junction.

According to the invention, a potential T-cell epitope is a sequence that, when considered as an isolated peptide, is predicted to bind to an MHC Class II molecule or an equivalent in a non-human species. A potential T-cell epitope is defined without consideration of other aspects of antigen processing, such as the efficiency of protein uptake into antigen-presenting cells, the efficiency of cleavage at sites in an intact protein to yield a peptide that can bind to MHC Class II, and so on. Thus, the set of T-cell epitopes that are actually presented on MHC Class II after administration of a protein to an animal is a subset of the potential T-cell epitopes.

According to the invention, a T-cell epitope is an epitope on a protein that interacts with an MHC class II molecule. Without wishing to be bound by theory, it is understood that a T-cell epitope is an amino acid sequence in a protein or a fusion protein, that failed to undergo the negative T-cell selection process during T-cell development and therefore will be expected to be presented by an MHC Class II molecule and recognized by a T-cell receptor. In a preferred embodiment of the invention, the non-self T-cell epitopes are present in the junction region at the fusion junction of two proteins that form a fusion protein.

The invention provides non-computer methods for reducing or eliminating the number of T-cell epitopes in a fusion protein junction without requiring elaborate computer simulations or protein three-dimensional structures. In one embodiment, a method of the invention takes advantage of the fact that a core segment of nine amino acids interacts with both the MHC class II molecule as well as the T-cell receptor during antigen presentation. The N-terminal most amino acid is called an "anchor" position residue that binds to a deep pocket within the MHC class II molecule. One of the following amino acids is typically present at the anchor position which is important for binding to an MHC class II molecule: Leucine, Valine, Isoleucine, Methionine, Phenylalanine, Tyrosine and Tryptophan. According to the invention, an additional 2 to 3 amino acids adjacent to the core 9 amino acids also affect the interaction with MHC molecules. In addition, the C-terminal most amino acid in the first protein of the fusion protein can generally be substituted. This is useful especially when the N-terminal fusion partner or first protein is known to be active when fused to the C-terminal fusion partner or second protein at the C-terminus of the first protein.

A general method of the invention includes mutating any Leucines, Valines, Isoleucines, Methionines, Phenylalanines, Tyrosines or Tryptophans that occur in the C-terminal most eight amino acids of an N-terminal fusion partner in a fusion protein. In one embodiment, one or more of these amino acids in a candidate junctional T-cell epitope amino acids is preferentially mutated to a Threonine, an Alanine or a Proline. This retains some of the hydrophobic nature of the amino acid that is replaced. In further embodiments of the invention, one more of the above-mentioned amino acids is deleted from a candidate or potential junctional T-cell epitope, or replaced with an appropriate amino acid analog. According to the invention, if an amino acid is deleted to destroy a potential T-cell epitope, care is taken not to generate a new T-cell epitope that includes amino acids near the deletion.

According to the invention, it is often useful to construct a generalized expression plasmid construction intermediate comprising the coding sequence for an N-terminal fusion partner containing a mutation of one or more hydrophobic residues in the last eight amino acids. Generally, such a plasmid has one or more convenient restriction enzyme sites at or near the DNA encoding the C-terminus of the N-terminal fusion partner.

The purpose of a plasmid construction intermediate is to construct expression plasmids encoding a fusion protein in which one or more N-terminal fusion partners has one or more substitutions of a Leucine, Valine, Isoleucine, Methionine, Phenylalanine, Tyrosine, or Tryptophan to another amino acid in the eight C-terminal amino acids. The construction of such final expression plasmids may be accomplished by a variety of other methods well known in the art, such as generation of PCR fragments or synthetic nucleic acids, followed by ligation of the fragment into an appropriated vector or attachment with other sequences through well-known PCR techniques.

Specific preferred embodiments include Fc-X fusion plasmids, albumin-X fusion plasmids, scFv-X fusion plasmids, and Fab-X fusion plasmids. In the Fc(gamma)-X case, it is useful to introduce mutations into the coding sequence to bring about amino acid substitutions of the Leucine-Serine-Leucine-Serine segment near C-terminus the Fc region of an IgG1, IgG2, IgG3, or IgG4 molecule, as diagrammed here for IgG1: Amino acid sequences of human Fc regions derived from IgG1, IgG2, IgG3 and IgG4 are depicted in SEQ ID NOs: 1, 2, 3 and 4 respectively.

In one example, KSLSLSPGK (SEQ ID NO: 5) is changed to KSATATPGK (SEQ ID NO: 6). This mutation is designed to eliminate potential junctional T-cell epitopes and also remove a T-cell epitope in which the upstream Phenylalanine or Tyrosine serves as a position 1 anchor residue.

Alternatively, it is sometimes useful to combine mutations that remove candidate junctional T-cell epitopes with a mutation that extends the serum half-life. For example, by changing KSLSLSPGK (SEQ ID NO: 5) to KSATATPGA (SEQ ID NO: 7).

Other embodiments include substitutions in the LSLS segment to other amino acids such as Glycine or Proline.

In the case of expression vectors used for making IgA fusion proteins, it is useful to delete some of the C-terminal amino acids, so that the cysteine near the C-terminus that is involved in oligomerization of IgA is deleted. For example, fifteen amino acids can be deleted, such that the IgA heavy chain sequence ends with Proline-Threonine-Histidine before being fused to a second protein. In addition, it is useful to introduce the following changes near the C-terminus of CH3 domain of the IgA Fc region:

```
QKTIDRLAGKPTH          (SEQ ID NO: 8)
changed to

QKTADRTAGKPTH          (SEQ ID NO: 9)
```

Additional de-immunized sequences in an IgA-X fusion protein are,

```
QKTPTRTAGKPTH          (SEQ ID NO: 10)

QKTPTRPAGKPTH          (SEQ ID NO: 11)

QKTATRPAGKPTH.         (SEQ ID NO: 12)
```

In the case of an albumin-X fusion, it is useful to introduce the following changes in an albumin-X expression plasmid such that the C-terminus of albumin is modified as follows:

```
KKLVAASQAALGL          (SEQ ID NO: 13)
changed to

KKLVAASQAATTA.         (SEQ ID NO: 14)
```

Thus, the invention provides nucleic acid sequences and proteins that are useful in construction of less immunogenic fusion proteins. Specifically, the invention provides proteins with mutations of any Leucines, Valines, Isoleucines, Methionines, Phenylalanines, Tyrosines, or Tryptophans in the last eight amino acids. The proteins are preferably human proteins with sequences that generally correspond to sequences found in the human body. The invention also provides nucleic acid sequences encoding such proteins. The nucleic acid sequences for this aspect of the invention may exist as plasmids, PCR-generated fragments, or nucleic acids produced by chemical synthesis.

The invention also provides expression plasmids encoding a fusion protein in which one or more N-terminal fusion partners has one or more mutations of a Leucine, Valine, Isoleucine, Methionine, Phenylalanine, Tyrosine, or Tryptophan to another amino acid in the eight C-terminal amino acids.

For example, plasmids encoding an Fc-IL2 or whole-antibody-IL2 fusion protein in which the Fc region is mutated as described above are provided by the invention. In addition, fusions comprising an Fc region mutated as described above to normal or mutated forms of erythropoietin, such as the forms of erythropoietin described in WO01/36489, are provided by the invention.

The invention also provides a method for reducing immunogenicity of a fusion protein junction by introducing an N-linked or O-linked glycosylation site near, or preferably, at a fusion junction. For example, the amino acids Asparagine, Serine or Threonine, and a third residue are introduced as follows. Consider a sequence in which X's represent amino acids of an N-terminal fusion partner, and Z's represent amino acids of a C-terminal fusion partner.

$$X_1X_2X_3X_4X_5X_6Z_1Z_2Z_3Z_4Z_5Z_6Z_7Z_8Z_9$$

$$X_1X_2X_3X_4X_5N\ G\ S\ Z_3Z_4Z_5Z_6Z_7Z_8Z_9$$

According to this method, binding of a junction peptide is not necessarily blocked by introduction of the glycosylation site. However, any peptide that is bound in the MHC Class II groove and has the glycosylated asparagine C-terminal to the N-terminal-most anchor residue will not function as a T-cell epitope. The presence of the large glycosylation moiety will sterically hinder recognition of the MHC Class II/peptide complex. A preferred glycosylation site includes the sequence Asn-X-Ser or Asn-X-Thr wherein X is preferably Gly, but can be any amino acid.

Furthermore, the introduction of mutations introducing Glycine and Serine residues does not create new T-cell epitopes. Neither Glycine nor Serine can act as an anchor residue. During antigen processing, a fusion protein, in principle, is cleaved between the glycosylated Asparagine and the Glycine or between the Glycine and the Serine. In either case, the resulting peptides have the mutant Glycine and/or Serine residues N-terminal to an anchor residue, and thus the mutant Glycine and/or Serine residues are not recognized by a T cell receptor, since residues N-terminal to an anchor residue are outside the region recognized by the TCR.

In a variation of this method, a fusion junction region already contains a Serine or Threonine preceded by an amino acid residues such as Glycine, Serine, Alanine, etc. The second method is preferably used when a junction region is flexible and displaced from the hydrophobic core of each fusion partner, so that the novel N-linked glycosylation does not interfere with the folding or function of either fusion partner.

It is a straightforward matter for those skilled in the art of protein engineering to determine when introduction of a glycosylation site is feasible. For example, the three-dimensional structure of each fusion partner, or close homologs of the fusion partners, may be known. It is often the case that a few amino acids at the N-terminus or C-terminus of a protein are not resolved in an X-ray structure, or exhibit many possible conformations in an NMR structure. In cases where three or more amino acids are disordered on either side of a glycosylation site, there is some confidence that the resulting fusion protein will fold correctly and both partners will be active. Some routine experimentation is necessary to determine whether a given fusion protein construct will be functional.

In preferred embodiments of the invention, both the N-terminal and the C-terminal partner of the fusion protein are human proteins. Potential T-cell epitopes in such fusion proteins are created from the final 8 amino acids of the N-terminal partner (first protein) combined with the first 8 amino acids of the C-terminal partner (second protein). This provides a series of 8 hybrid 9-mers created from the first and second proteins. Any aliphatic or aromatic residue (Leucine, Valine, Isoleucine, Methionine, Phenylalanine, Tryptophan or Tyrosine) in the last 8 amino acids of the first protein presents a high risk of creating an MHC binding peptide with the amino acid in the first position (anchor position) that binds the pocket of the MHC molecule. Therefore, substitution of any of the above-mentioned amino acids, with an amino acid that is not one of the above-mentioned amino acids, and preferably with Alanine, Proline, or Threonine, will remove a candidate T-cell epitope.

For example, in the case of an Fc fusion protein containing the sequence:

HNHYTQKSLSLSPGKGGGGSGGGGSGGGGS, (SEQ ID NO: 15)

the leucine residues create two potential epitopes. Therefore, the sequence can be de-immunized as;

HNHYTQKSATATPGKGGGGSGGGGSGGGGS, (SEQ ID NO: 16)

by changing L to A and S to T. These changes remove epitopes with Leucine as the first amino acid in the MHC binding pocket and Tyrosine as the first amino acid in the MHC binding pocket, respectively.

These substitutions for deimmunization work in humans for all Fc fusion proteins, both with and without linker sequences, preferably when 1) both proteins in the fusion protein are human proteins; 2) the MHC binding peptides in the natural sequences of both proteins are ignored; and 3) the 9-mers identical to the original sequences are also ignored.

Methods of the invention are generally applicable in all vertebrate organisms, preferably in mammals and most preferably in humans. The invention is illustrated further by the following non-limiting examples.

EXAMPLES

Example 1

Deduction of Immunogenic Reactive Epitopes of huKS-IL2 Immunocytokine

HuKS-IL2 consists of humanized $V_H$ and $V_L$ regions combined with human H and L chain constant regions. The H chain was fused at its carboxyl terminus to the mature sequence of human IL-2 as described previously. This H chain is of the γ1 isotype and has high affinity for Fc receptors. Because of this high affinity HuKS-IL2 was cleared quickly from the circulation. Without wishing to be bound by theory, the clearance of HuKS-IL2 presumably occurs via FcR-bearing cells in the liver (Kupffer cells) and spleen (antigen presenting cells).

It was previously established that certain patients had made immune responses to some portion of the huKS-IL2 molecule, however, the epitopes recognized by these antibodies are not known. To deduce the reactive epitopes, relative reactivities of patient sera with huKS-IL2 were compared to other related proteins:

(1) Hu14.18-IL2, a molecule with completely different humanized V regions but exactly the same C regions and fusion junction with IL-2;

(2) VH1, a de-immunized form of huKS-IL2 with no T-cell epitopes in the VH and VL regions, derived from mouse V regions with surface-exposed mouse B-cell epitopes veneered to human residues.

(3) VH2, a de-immunized form of huKS-IL2 with one remaining T-cell epitope in CDR3, derived from mouse V regions with surface-exposed mouse B-cell epitopes veneered to human residues, in which the VH contains one T-cell epitope.

(4) 425-IL2 constructed with either KOL or EU Cγ1 regions (rather than KS) (to compare allotypic reactivity);

(5) huKS-mIL2—a molecule with the huKS V regions fused to mouse C regions and mouse IL-2;

(6) human Fc-IL2;

(7) human Fc only;

(8) human IL-2 only.

Immunoglobulin fusion proteins and fragments were purified by protein A Sepharose chromatography and were coated on 96-well plates in bicarbonate buffer and then blocked with 1% goat serum containing 1% BSA. Dilutions of patient sera were incubated and then unbound material was removed by three washes with PBS-Tween. Bound human antibodies from the patient sera were detected with various HRP-conjugated antibodies depending on the bound protein. Generally, goat anti-human λ chain HRP conjugate was used because most of the plate-bound proteins consisted of human Fc and human κ chains.

Certain patient sera showed a clear reactivity to huKS-IL2 that was not detectable in pre-injection sera from the same patients. Preimmune antisera was used to establish a baseline non-immunized control. Reactivity seen in patient sera can be attributed to (1) anti-IL2 reactivity, (2) anti Fc (allotypic) reactivity, (3) reactivity to the novel junction sequence or (4) anti-idiotypic reactivity with the KS idiotype, or a combination of reactivities.

No patient serum reacted significantly with recombinant IL-2 or to the Fc region (1 and 2 above). Some patients showed anti-idiotypic reactivity to the KS V regions. All patient sera showed reactivity with Fc-IL2. Three of four patients showed reactivity to Fc-IL2. The presence of reactivity against Fc-IL2 but not against either Fc or IL2 suggests that the junction between Fc and IL2 was recognized by the patients' anti-sera.

Example 2

Modification of Amino Acid Residues at the Junction of an Antibody-Cytokine Fusion Protein to Reduce Immunogenicity by Elimination of MHC Class II Binding Motifs Peptide threading analysis identified two overlapping peptide segments with strong MHC binding potential at the junction between the Fc and IL2 portion of the immunocytokine. The peptide threading and identification of potential T-cell epitopes was performed as disclosed in Carr (WO00/34317).

Amino acid changes were introduced such that the existing potential MHC Class II binding epitopes were eliminated, but new potential MHC Class II epitopes were not introduced.

Modification of a junction sequence LSLSPGK-AP (SEQ ID NO: 17) to ATATPGA-AP (SEQ ID NO: 18)("LSLS to ATAT"), where the hyphen is the immunocytokine huKS-IL2 junction, made junction-derived peptide sequences incapable of binding to any human MHC Class II with an affinity high enough to result in immunogenicity.

Example 3

Modification of Amino Acid Residues at the Junction of Immunocytokine Fusion Proteins to Reduce Immunogenicity Modification of a junction sequence LSLSPGK-AP (SEQ ID NO: 17) to LNLSPGA-AP (SEQ ID NO: 19)("LSLS to LNLS"), where the hyphen is the immunocytokine huKS-IL2 junction, results in junction-derived peptide sequences that are still capable of binding to certain MHC Class II molecules. However, when the KS-IL2 protein is expressed in mammalian cells and secreted, the protein is N-glycosylated near the junction because of the NXS/T sequence.

The resulting junction-derived peptides are not effective as T-cell epitopes, because when the junction-derived peptides are presented to T cells by MHC Class II, the large N-glycosylation moiety prevents specific docking between a T cell-receptor and MHC Class II.

Example 4

Characterization of the Immune Reactivity of Antigen Presenting Cells to Immunocytokine huKs-IL2 in Comparison to a De-Immunized huKS-IL2 Immunocytokine Reduction of immunogenicity due to modification of the reactive epitope by mutating LSLS to ATAT is directly tested as follows. Synthetic peptides mimicking this sequence alter the immune response of a classic antigen presenting cell such as a dendritic cell (DC). The following synthetic peptides

```
KSLSLSPGK-APTS        (SEQ ID NO: 20)
and

KSATATPGK-APTS,       (SEQ ID NO: 21)
``` where the hyphen is the KS-IL2 junction, are used to stimulate DC-mediated antigen presentation to autologous T cells. The ability of those T cells to proliferate in response to a subsequent challenge with the peptide antigen serves as a measure of immunogenicity of that peptide.

Specifically, peripheral blood mononuclear cells (PBMC) are isolated from leukopacks by standard density gradient techniques. Mononuclear cells are resuspended in serum-free Aim V culture media and allowed to adhere. After 2 h at 37° C. nonadherent cells are removed. Adherent cells are cultured for 7 days in media containing human GM-CSF (50 ng/ml) and IL-4 (20 ng/ml) to derive immature dendritic cells (DC). After 7 days, the cells are harvested and phenotypically characterized by flow cytometry with appropriate FITC-labeled Abs for MHC class I, MHC class II, CD80 and CD40 to confirm the immature DC phenotype.

Non-adherent cells are cultured with IL2 and IL7 to obtain autologous effector cells (T-cells) to be used in subsequent functional studies. For functional studies, T-cells are added to immature dendritic cells (10:1 ratio) and co-cultured with huKS, de-immunized huKS, peptide junction 13 mer (K S L S L S P G K-APTS) (SEQ ID NO: 20) and the modified, de-immunized 13 mer peptide (K S A T A T P G K-A P T S) (SEQ ID NO: 21). Comparison of the proliferation index, as measured by tritiated thymidine incorporation after exposure to each of the immunocytokines or immunogenic and modified de-immunized peptides demonstrates the degree of immunogenicity of each molecule. Namely, an increase in radioactive incorporation is roughly proportional to the ability of each peptide to be bind to a class II MHC molecule on DC and be presented to T cells.

Example 5

Deduction of Immunogenic Reactive Epitopes Found in Albumin Fusion Proteins and Modification of Amino Acid Residues at a Fusion Junction to Reduce Immunogenicity Human serum albumin (HSA), due to its remarkably long half-life, its wide in vivo distribution and its lack of enzymatic or immunological functions, has been used as a carrier for therapeutic peptides/proteins. A genetically engineered HSA-CD4 hybrid has been shown to block the entry of the human immunodeficiency virus into CD4+ cells while exhibiting antiviral in vitro properties similar to those of soluble CD4 (Yeh et al, PNAS 89:1904-1908, 1992). Thus, the genetic fusion of bioactive peptides to HSA is useful for designing and recovering secreted therapeutic HSA derivatives. However, as with all fusion proteins, HSA-CD4 has a novel junction which can be immunogenic and contains T-cell epitopes capable of being presented on MHC class II molecules. Analysis of the junction between HSA and CD4 using the methods of Examples 1, 2, 3, and 4 identifies peptides with MHC binding potential. The potentially immunogenic sequences are modified to decrease or eliminate potential T and B-cell epitopes in order to reduce immunogenicity. Similarly, a novel glycosylation site can be introduced into the junction region in order to reduce immunogenicity.

```
 Albumin sequence        CD4 sequence
                                             (SEQ ID NO: 22)
 TCFAEEGKKLVAASQAALGL  -  KKVVLGKKGDTVELTCTAS.
```

It is contemplated by the invention that the HSA-IFNalpha fusion protein junction region contains three candidate T-cell epitopes,

```
 KKLVAASQAALGL;      (SEQ ID NO: 13)

KLVAASQAALGLC;      (SEQ ID NO: 23)
 and

LGLCDLPQTHSLG.      (SEQ ID NO: 24)
```

The T-cell epitopes depicted in SEQ ID NOs: 13 and 23 overlap and can be de-immunized by changing LV (in bold) to anything except F, I, L, M, V, W and Y. Alternatively, the peptide threading score can be reduced significantly by changing LG to TT. The T-cell epitope in SEQ ID NO: 24 can be de-immunized by changing the second L (in bold) to an A.

Furthermore, it is contemplated that in the case of an HSA-X fusion, wherein X can be any protein, deimmunization of the fusion junction is achieved by changing the amino acid sequence AALGL (SEQ ID NO: 25) to TATTA (SEQ ID NO: 26).

```
 CFAEEGKKLVAASQTATTA.      (SEQ ID NO: 27)
```

Example 6

X-Fc Fusion Proteins and Modification of Amino Acid Residues at a Fusion Junction to Reduce Immunogenicity In some instances it is specifically advantageous to engineer a fusion protein in the X-Fc orientation. With these constructs, a target protein is a N-terminal fusion protein and a Fc fragment follows. For example, the glucagon-like peptide (GLP-1) requires a free N-terminus for its activity, so a GLP-1-Fc fusion is useful.

A GLP-1-Fc fusion protein is constructed according to standard techniques described in the art. This fusion protein has the C-terminus of GLP-1 joined to the hinge of the γ1 heavy chain. The γ1 hinge sequence containing a Cys to Ser mutation (residue 5) which eliminates the Cys residue that forms a disulphide bond with the light chain in IgG1 (Lo et al., (1998) Protein Engineering 11:495-500) is used. The non-mutant Fc sequence is

```
 EPKSCDKTHTCPPCPAPELLG      (SEQ ID NO: 28)
``` with the hinge region being underlined, followed by the start of the CH2 domain sequence.

The fusion junction between GLP-1 (7-37) and mutant Fc is:

```
                                              (SEQ ID NO: 29)
 HAEGTFTSDVSSYLEGQAAKEFIAWLVKGRG - EPKSSDKTHTCPPCPA
 PELLG.
```

The fusion junction between GLP-1 (7-37) and normal Fc is:

```
                                              (SEQ ID NO: 30)
   SYLEGQAAKEFIAWLVKGRG - EPKSCDKTHTCPPCPAPELLG
```

Three potential epitopes are identified by peptide threading at the GLP-1-Fc fusion junction.

```
 KEFIAWLVKGRGE         (SEQ ID NO: 31)

EFIAWLVKGRGEP         (SEQ ID NO: 32)

AWLVKGRGEPKSS.        (SEQ ID NO: 33)
```

Analysis of fusion junctions between GLP-1 (bold text) and Fc (plain text), performed as in Examples 1-3, identifies peptides with MHC binding potential. After identification of potential sites by peptide threading analysis, the potentially immunogenic sequences are modified by amino acid substitution to reduce or eliminate potential T and B-cell binding epitopes and decrease immunogenicity.

The above-mentioned potential T-cell epitopes depicted in SEQ ID NOs: 31, 32 and 33 are de-immunized by making single amino acid substitutions. For example, peptide shown in SEQ ID NO: 31 is de-immunized by changing the Lysine (shown in bold) to a Threonine and the Arginine (shown in bold) to a Threonine. The peptide shown in SEQ ID NO: 32 is de-immunized by replacing the Isoleucine (shown in bold) with an Alanine or a Proline and the peptide in SEQ ID NO: 33 is de-immunized by replacing the Leucine with an Alanine or a Proline. The resulting de-immunized junction is:

HAEGTFTSDVSSYLEGQAAKEFAAWAVTGTG - (SEQ ID NO: 34)
EPKSSDKTHTCPPCPAPELLG.

According to an exemplary method for introducing a glycosylation site at a fusion junction the following changes are introduced:

SYLEGQAAKEFIAWLVKGRN - (SEQ ID NO: 35)
GSKSSDKTHTCPPCPAPELLG.

Example 7

Deduction of Immunogenic Reactive Epitopes of Enbrel, a TNFR-Fc Fusion Protein and Modification of Amino Acid Residues at a Fusion Junction to Reduce Immunogenicity ENBREL or etanercept, a X-Fc fusion protein approved by the FDA, is a tumor necrosis factor (TNF) inhibitor used to treat rheumatoid arthritis. ENBREL is a dimeric fusion protein consisting of an extracellular-ligand-binding domain of TNF receptor linked to an Fc protein of human IgG1. TNFR-Fc competitively inhibits binding of TNF to its receptor and renders the bound TNF biologically inactive, resulting in significant reduction in inflammatory activity. As described above for GLP-1-Fc, TNFR-Fc has a novel junction which contains potential T-cell epitopes.

The junction between a direct fusion of a C-terminus portion of TNF-R (bold text) to the N-terminus of the g1 hinge (plain text with the underline region representing the hinge region) is

STSFLLPMGPSPPAEGSTGD - (SEQ ID NO: 36)
EPKSCDKTHTCPPCPAPELLG

Analysis of a junction between TNF-R and Fc, performed as in Examples 1-4, identifies peptides with MHC binding potential. After identification of potential sites by peptide threading analysis, the potentially immunogenic sequences are modified by amino acid substitution to reduce or eliminate potential T and B-cell binding epitopes and decrease immunogenicity.

According to an exemplary method for introducing a glycosylation site at a fusion junction the following changes are introduced:

STSFLLPMGPSPPAEGSTGN - (SEQ ID NO: 37)
GSKSCDKTHTCPPCPAPELLG.

Example 8

Deduction of Immunogenic Reactive Epitopes for Fc-X-Y Fusion Proteins Such as Fc-IL12-IL2 and Modification of Amino Acid Residues at the Fusion Junction to Reduce Immunogenicity Fusion proteins of a Fc-X-Y orientation such as Fc-IL12-IL2 have multiple novel fusion junctions which are potentially immunogenic. For instance, Fc-IL12 has a fusion junction similar to other Fc-X fusion proteins or immunocytokines (Example 1) but is novel due to the usage of the cytokine IL12. The fusion junction is analyzed for immunogenic binding sites and modified accordingly. Secondly, there is an X-Y fusion junction comparable to that described in Example 5, with two different cytokines constituting a fusion protein. Peptide thread analysis is used for each of the fusion junctions.

Analysis of the junctions:

(1) MHEALHNHYTQKSLSLSPGK - (SEQ ID NO: 38)
RNLPVATPDPGMFPCLHH SQ between the C-terminus of Fc (bold text) and the N-terminus of IL12p35 (plain text), and (2) RAQDRYYSSSWSEWASVPCS - (SEQ ID NO: 39)
APTSSSTKKTQLQLEHLLLD between the C-terminus of IL12p40 (bold text) and the N-terminus of IL2 (plain text) by peptide threading identifies peptides with MHC binding potential. The potentially immunogenic sequences are modified to decrease or eliminate potential T-cell epitopes.

For example, in sequence (1) above, the following changes are made:

(SEQ ID NO: 40)
MHEALHNHYTQKSATATPGK - RNLPVATPDPGMFPCLHHSQ.

These changes reduce or eliminate MHC Class II-binding potential of several T cell epitopes at a junction of Fc and the p35 subunit of IL12.

In another example, sequence (2) above is modified to introduce a glycosylation site by introducing an Asparagine and Glycine at the first two positions within IL-2. This strategy uses the naturally occurring Threonine at position 3 of mature IL-2. In addition, it is important to not disrupt the formation of a disulfide bond in the p40 moiety, so it is useful to separate the glycosylation site by at least one or two amino acids from the Cysteine in p40.

(SEQ ID NO: 41)
RAQDRYYSSSWSEWASVPCS - NGTSSSTKKTQLQLEHLLLD.

In the case of the IL12p40-IL2 fusion, introduction of a glycosylation site as discussed above creates the following potential T-cell epitopes.

SEWASVPCSNGTS (SEQ ID NO: 42)

ASVPCSNGTSSST (SEQ ID NO: 43)

Example 9

Deduction of Immunogenic Reactive Epitopes in Junction of an X-Fc-Y Fusion Protein and Modification of Amino Acid Residues at a Fusion Junction to Reduce MHC Class II Binding Fusion proteins of the X-Fc-Y configuration, such as IL4-Fc-GMCSF, have multiple novel fusion junctions that contain potential T-cell epitopes. The IL4-Fc is a junction analogous to other X-Fc fusion proteins (Examples 6 and 7) but is novel due to the use of the cytokine IL4. For example, a form of Fc using a hinge region, CH2, and CH3 domain from human γ1 is used. As stated above, a γ1 hinge sequence in pdCs-huFcγ1 may contain a Cys to Ser mutation (underlined) that eliminates the Cys residue that forms a disulphide bond with a light chain in IgG1 (Lo et al., (1998) Protein Engineering 11:495-500), thereby creating a third potentially immunogenic fusion junction for analysis. The fusion junction is analyzed for potential T-cell epitopes and modified according to the methods of Examples 1-4.

There is an Fc-Y fusion junction comparable to that described in Example 1 for the immunocytokine huKS-IL2, with a different cytokine GMCSF constituting a fusion protein. This fusion junction is also analyzed for potential T-cell epitopes and modified according to the methods of Examples 1-4.

Specifically, analysis of the junctions (SEQ ID NO: 44)
(1) ENFLERLKTIMREKYSKCSS - epks<u>c</u>dkthtcppcpapellg between the C-terminus of IL4 (bold text) and the N-terminus of Fc (plain text), and (SEQ ID NO: 45)
(2) MHEALHNHYTQKSLSLSPGK - parspspstqpwehvnaiqe between the C-terminus of Fc (bold text) and the N-terminus of GMCSF (plain text) by peptide threading identifies peptides with MHC binding potential. The potential T-cell epitopes are modified to decrease or eliminate potential T epitopes in order to reduce immunogenicity.

A candidate T-cell epitope at the junction of IL4-Fc fusion protein is, EKYSKCSSEPKSC (SEQ ID NO: 46), where changing E (in bold) to T reduces the peptide threading score or the MHC Class II binding potential significantly. The sequence of the modified IL4-Fc fusion is as follows:

(SEQ ID NO: 47)
ENFLERLKTIMREKYSKCSS - <u>t</u>pkscdkthtcppcpapellg.

The Fc-GMCSF fusion junction is de-immunized by changing the sequence LSLS to ATAT as shown below.

(SEQ ID NO: 48)
MHEALHNHYTQKS<u>ATAT</u>PGK - parspspstqpwehvnaiqe.

Example 10

Modification of Amino Acid Residues at a Fusion Junction of Immunocytokines and Immunofusins Prepared with a Hybrid Isotype to Remove T-Cell Epitopes It is often useful to construct an antibody or antibody-based fusion protein with a hybrid isotype, so that useful features of different isotypes may be combined into a single molecule. Fusion proteins with hybrid isotypes may be modified according to the invention to reduce immunogenicity.

An antibody fusion protein with the following components is constructed by standard recombinant DNA techniques: a light chain and a heavy chain, the V regions recognizing a tumor-specific antigen, the light chain being a typical light chain, and the heavy chain comprising CH1, CH2, and CH3 domains from IgG2 and a hinge region from IgG1, with a cytokine fused to the C-terminus of the heavy chain involving a fusion junction as described above.

This protein contains novel junctions between CH1g2 and hinge-g1, and hinge-g1 and CH2g2. The identification and modification of potential T-cell epitopes in these junctions is performed as follows. For immunocytokines and Fc-X fusion proteins prepared with either an IgG2 or an IgG2h isotype, these modifications are identical to those set forth in Examples 1, 2, 3, and 8 above. For X-Fc IgG2h immunofusins, the novel junction is also identical since the N-terminus of the Fc is located within the hinge region of the IgG2h protein which has been modified to an IgG1 type. However, there are two novel fusion junctions in that the IgG1 hinge inserted into a IgG2 immunoglobulin creates two novel junctions between the IgG2 CH1 and IgG1 hinge and the IgG1 hinge and the IgG2 CH2.

IgG2 CH1-IgG1 hinge-IgG2 CH2-IgG2 CH3-target protein.

Thus, analysis of the junctions (SEQ ID NO: 49)
qtytcnvdhkpsntkvdktv - epks<u>c</u>dkthtcppcp between the C-terminus of IgG2 CH1 (bold text) and the N-terminus of the IgG1 hinge (plain text), and (SEQ ID NO: 50)
epks<u>c</u>dkthtcppcp - appvagpsvflfppkpkdtl between the C-terminus of the IgG1 hinge (bold text) and the N-terminus of IgG2 CH2 F (plain text) by peptide threading should identify peptides with MHC binding potential. The potentially immunogenic sequences are modified to decrease or eliminate potential T and B-cell epitopes in order to reduce immunogenicity.

Two potential T-cell epitopes in the IgG2CH1-IgG1 hinge fusion junction are,

TKVDKTVEPKSCD    (SEQ ID NO: 51)

and

KTVEPKSCDKTHT.   (SEQ ID NO: 52)

The IgG2CH1-IgG1 hinge fusion junction is de-immunized by changing the V (in bold) to an A, a T or a P. The sequence of the modified fusion junction is depicted in SEQ ID NO: 53.

```
                                                    (SEQ ID NO: 53)
    qtytcnvdhkpsntkadkta - epkscdkthtcppcp.
```

As stated above, the γ1 hinge sequence in pdCs-huFcγ1 may contain a Cys to Ser mutation (underlined) that eliminates the Cys residue that forms a disulphide bond with the light chain in IgG1 (Lo et al., (1998) Protein Engineering 11:495-500), thereby creating two additional potentially immunogenic fusion junctions for analysis and modification:

```
                                                    (SEQ ID NO: 54)
   (3) qtytcnvdhkpsntkvdktv - epksSdkthtcppcp
                                                    (SEQ ID NO: 55)
   (4) epksSdkthtcppcp - appvagpsvflfppkpkdtl.
```

Example 11

Generation of Fc-EPO Fusion Protein Using Hybrid Isotype Fc Components of IgG1 and IgG4

To generate an Fc-erythropoietin fusion protein, the following expression plasmid was constructed using standard molecular biology techniques. An XmaI-XhoI DNA fragment containing a form of the human erythropoietin coding sequence with mutations resulting in the amino acid substitutions His32Gly, Cys33Pro, Trp88Cys, and Pro90Ala, as disclosed in WO01/36489, was used. The corresponding protein sequence is shown in SEQ ID NO: 56.

APPRLICDSRVLERYLLEAKEAENITTGCAEGPSLNENITVPDTKVNFYA

WKRMEVGQQAVEVWQGLALLSEAVLRGQALLVNSSQPCEGLQLHVDKAVS

GLRSLTTLLRALGAQKEAISPPDAASAAPLRTITADTFRKLFRVYSNFLR

GKLKLYTGEACRTGDR

This XmaI-XhoI DNA fragment was inserted into a plasmid vector that encodes a hinge region from IgG1 and a CH2 and CH3 region from IgG2, except that there were two sets of mutations that resulted in amino acid substitutions in the region of the CH3 C-terminus, such that the sequence at the junction of the CH3 C-terminus and the Epo N-terminus is as follows:

```
   . . . TQKSATATPGA-APPRLI . . .         (SEQ ID NO: 57)
```

The first set of mutations, which change the sequence KSLSLSPG (SEQ ID NO: 58) of the IgG2 CH3 region to KSATATPG (SEQ ID NO: 59), is disclosed in U.S. Patent Application Ser. No. 60/280,625. The effect of the substitution of Leu-Ser-Leu-Ser (position 3 to position 6 of SEQ ID NO: 58) with Ala-Thr-Ala-Thr (position 3 to position 6 of SEQ ID NO: 59) is to remove potential human non-self T-cell epitopes that may arise because the junction between human Fc and human erythropoietin contains non-self peptide sequences. The second set consisting of the single amino acid substitution K to A at the C-terminal amino acid of the CH3 region, is disclosed in U.S. patent application Ser. No. 09/780,668.

The resulting plasmid was transfected into NS/0 cells and the Fc-Epo fusion protein was expressed and purified according to the procedures known in the art. After purification based on binding to protein A, the huFcγ2h-huEpo protein containing the IgG2 CH3 and erythropoietin substitutions described above was characterized by size exclusion chromatography and found to consist of 97% monomer and 90% monomer in two independent preparations. The huFcγ2h-huEpo protein containing the IgG2 CH3 and erythropoietin substitutions described above was found to be about as active, on a molar basis, as human erythropoietin in a cell-based assay that measured the ability of an erythropoietin protein to stimulate TF-1 cell division. The assay was performed as described in WO01/36489.

In addition, fusions of non-mutant human erythropoietin to the C-terminus of an Fc region consisting of either IgG1 (hinge-CH2-CH3), IgG2(hinge-CH2-CH3), or IgG1(hinge)-IgG2(CH2-CH3) were characterized. Expression plasmids comprising non-mutant human Fc sequences and non-mutant erythropoietin sequences were constructed analogously to the plasmid described above. NS/0 cells were transfected with the Fcγ1-Epo, Fcγ2-Epo, and Fcγ2h-Epo expression plasmids, and stable clones were isolated after screening an approximately equal number of clones for each plasmid. The best-producing clones yielded 50 μg/ml for Fcγ1-Epo, 20 μg/ml for Fcγ2-Epo, and 120 μg/ml for Fcγ2h-Epo.

The following example describes in detail a preferred method for identification of immunogenic sequence regions (T-cell epitopes) within the sequences of the fusion proteins as disclosed in this invention. However, it should be pointed out, that said molecules can be obtained by other known methods.

Example 12

Identification of T-Cell Epitopes by Computational Methods

According to the invention, epitopes in a junction region of a fusion protein can be modified using methods for introducing mutations into proteins to modulate their interaction with the immune system. According to the invention, known methods in the art that can be adapted according to the invention include those described in the prior art (WO 92/10755 and WO 96/40792 (Novo Nordisk), EP 0519 596 (Merck & Co.), EP 0699 755(Centro de Immunologia Molecular), WO 98/52976 and WO 98/59244 (Biovation Ltd.) or related methods.

Advantageous mutant proteins, however, can be obtained if the identification of said epitopes is realized by the following new method which is described herewith in detail and applied to the junction region of fusion proteins according to the invention.

There are a number of factors that play important roles in determining the total structure of a protein, polypeptide or immunoglobulin. First, the peptide bond, i.e., that bond which joins the amino acids in the chain together, is a covalent bond. This bond is planar in structure, essentially a substituted amide. An "amide" is any of a group of organic compounds containing the grouping —CONH—.

The planar peptide bond linking Cα of adjacent amino acids may be represented as depicted below:

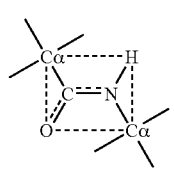

Because the O═C and the C—N atoms lie in a relatively rigid plane, free rotation does not occur about these axes. Hence, a plane schematically depicted by the interrupted line is sometimes referred to as an "amide" or "peptide plane" plane wherein lie the oxygen (O), carbon (C), nitrogen (N), and hydrogen (H) atoms of the peptide backbone. At opposite corners of this amide plane are located the Cα atoms. Since there is substantially no rotation about the O═C and C—N atoms in the peptide or amide plane, a polypeptide chain thus comprises a series of planar peptide linkages joining the Cα atoms.

A second factor that plays an important role in defining the total structure or conformation of a polypeptide or protein is the angle of rotation of each amide plane about the common Cα linkage. The terms "angle of rotation" and "torsion angle" are hereinafter regarded as equivalent terms. Assuming that the O, C, N, and H atoms remain in the amide plane (which is usually a valid assumption, although there may be some slight deviations from planarity of these atoms for some conformations), these angles of rotation define the N and R polypeptide's backbone conformation, i.e., the structure as it exists between adjacent residues. These two angles are known as $\phi$ and $\psi$. A set of the angles $\phi_i$, $\psi_i$, where the subscript i represents a particular residue of a polypeptide chain, thus effectively defines the polypeptide secondary structure. The conventions used in defining the $\phi$, $\Psi$ angles, i.e., the reference points at which the amide planes form a zero degree angle, and the definition of which angle is $\phi$, and which angle is $\Psi$, for a given polypeptide, are defined in the literature. See, e.g., Ramachandran et al. *Adv. Prot. Chem.* 23:283-437 (1968), at pages 285-94, which pages are incorporated herein by reference.

The present method can be applied to any protein, and is based in part upon the discovery that in humans the primary Pocket 1 anchor position of MHC Class II molecule binding grooves has a well designed specificity for particular amino acid side chains. The specificity of this pocket is determined by the identity of the amino acid at position 86 of the beta chain of the MHC Class II molecule. This site is located at the bottom of Pocket 1 and determines the size of the side chain that can be accommodated by this pocket. Marshall, K. W., *J. Immunol.,* 152:4946-4956 (1994). If this residue is a glycine, then all hydrophobic aliphatic and aromatic amino acids (hydrophobic aliphatics being: valine, leucine, isoleucine, methionine and aromatics being: phenylalanine, tyrosine and tryptophan) can be accommodated in the pocket, a preference being for the aromatic side chains. If this pocket residue is a valine, then the side chain of this amino acid protrudes into the pocket and restricts the size of peptide side chains that can be accommodated such that only hydrophobic aliphatic side chains can be accommodated. Therefore, in an amino acid residue sequence, wherever an amino acid with a hydrophobic aliphatic or aromatic side chain is found, there is the potential for a MHC Class II restricted T-cell epitope to be present. If the side-chain is hydrophobic aliphatic, however, it is approximately twice as likely to be associated with a T-cell epitope than an aromatic side chain (assuming an approximately even distribution of Pocket 1 types throughout the global population).

A computational method embodying the present invention profiles the likelihood of peptide regions to contain T-cell epitopes as follows: (1) The primary sequence of a peptide segment of predetermined length is scanned, and all hydrophobic aliphatic and aromatic side chains present are identified. (2) The hydrophobic aliphatic side chains are assigned a value greater than that for the aromatic side chains; preferably about twice the value assigned to the aromatic side chains, e.g., a value of 2 for a hydrophobic aliphatic side chain and a value of 1 for an aromatic side chain. (3) The values determined to be present are summed for each overlapping amino acid residue segment (window) of predetermined uniform length within the peptide, and the total value for a particular segment (window) is assigned to a single amino acid residue at an intermediate position of the segment (window), preferably to a residue at about the midpoint of the sampled segment (window). This procedure is repeated for each sampled overlapping amino acid residue segment (window). Thus, each amino acid residue of the peptide is assigned a value that relates to the likelihood of a T-cell epitope being present in that particular segment (window). (4) The values calculated and assigned as described in Step 3, above, can be plotted against the amino acid coordinates of the entire amino acid residue sequence being assessed. (5) All portions of the sequence which have a score of a predetermined value, e.g., a value of 1, are deemed likely to contain a T-cell epitope and can be modified, if desired.

This particular aspect of the present invention provides a general method by which the regions of peptides likely to contain T-cell epitopes can be described. Modifications to the peptide in these regions have the potential to modify the MHC Class II binding characteristics.

According to another aspect of the present invention, T-cell epitopes can be predicted with greater accuracy by the use of a more sophisticated computational method which takes into account the interactions of peptides with models of MHC Class II alleles.

The computational prediction of T-cell epitopes present within a peptide according to this particular aspect contemplates the construction of models of at least 42 MHC Class II alleles based upon the structures of all known MHC Class II molecules and a method for the use of these models in the computational identification of T-cell epitopes, the construction of libraries of peptide backbones for each model in order to allow for the known variability in relative peptide backbone alpha carbon (Cα) positions, the construction of libraries of amino-acid side chain conformations for each backbone dock with each model for each of the 20 amino-acid alternatives at positions critical for the interaction between peptide and MHC Class II molecule, and the use of these libraries of backbones and side-chain conformations in conjunction with a scoring function to select the optimum backbone and side-chain conformation for a particular peptide docked with a particular MHC Class II molecule and the derivation of a binding score from this interaction.

Models of MHC Class II molecules can be derived via homology modeling from a number of similar structures found in the Brookhaven Protein Data Bank ("PDB"). These may be made by the use of semi-automatic homology modeling software (Modeller, Sali A. & Blundell T L., 1993. *J. Mol Biol* 234:779-815) which incorporates a simulated annealing function, in conjunction with the CHARMm forcefield for energy minimization (available from Molecular Simulations Inc., San Diego, Calif.). Alternative modeling methods can be utilized as well.

The present method differs significantly from other computational methods which use libraries of experimentally derived binding data of each amino-acid alternative at each position in the binding groove for a small set of MHC Class II molecules (Marshall, K. W., et al., *Biomed. Pept. Proteins Nucleic Acids,* 1(3):157-162) (1995) or yet other computational methods which use similar experimental binding data in order to define the binding characteristics of particular types of binding pockets within the groove, again using a relatively small subset of MHC Class II molecules, and then 'mixing and matching' pocket types from this pocket library to artificially create further 'virtual' MHC Class II molecules (Sturniolo T., et al., *Nat. Biotech*, 17(6): 555-561 (1999). Both prior methods suffer the major disadvantage that, due to the complexity of the assays and the need to synthesize large numbers of peptide variants, only a small number of MHC Class II molecules can be experimentally scanned. Therefore the first prior method can only make predictions for a small number of MHC Class II molecules. The second prior method also makes the assumption that a pocket lined with similar amino-acids in one molecule will have the same binding characteristics when in the context of a different Class II allele and suffers further disadvantages in that only those MHC Class II molecules can be 'virtually' created which contain pockets contained within the pocket library. Using the modeling approach described herein, the structure of any number and type of MHC Class II molecules can be deduced, therefore alleles can be specifically selected to be representative of the global population. In addition, the number of MHC Class II molecules scanned can be increased by making further models further than having to generate additional data via complex experimentation.

The use of a backbone library allows for variation in the positions of the $C\alpha$ atoms of the various peptides being scanned when docked with particular MHC Class II molecules. This is again in contrast to the alternative prior computational methods described above which rely on the use of simplified peptide backbones for scanning amino-acid binding in particular pockets. These simplified backbones are not likely to be representative of backbone conformations found in 'real' peptides leading to inaccuracies in prediction of peptide binding. The present backbone library is created by superposing the backbones of all peptides bound to MHC Class II molecules found within the Protein Data Bank and noting the root mean square (RMS) deviation between the $C\alpha$ atoms of each of the eleven amino-acids located within the binding groove. While this library can be derived from a small number of suitable available mouse and human structures (currently 13), in order to allow for the possibility of even greater variability, the RMS figure for each $C''-\alpha$ position is increased by 50%. The average $C\alpha$ position of each amino-acid is then determined and a sphere drawn around this point whose radius equals the RMS deviation at that position plus 50%. This sphere represents all allowed $C\alpha$ positions.

Working from the $C\alpha$ with the least RMS deviation (that of the amino-acid in Pocket 1 as mentioned above, equivalent to Position 2 of the 11 residues in the binding groove), the sphere is three-dimensionally gridded, and each vertex within the grid is then used as a possible location for a $C\alpha$ of that amino-acid. The subsequent amide plane, corresponding to the peptide bond to the subsequent amino-acid is grafted onto each of these $C\alpha$s and the $\phi$ and $\psi$ angles are rotated step-wise at set intervals in order to position the subsequent $C\alpha$. If the subsequent $C\alpha$ falls within the 'sphere of allowed positions' for this $C\alpha$ than the orientation of the dipeptide is accepted, whereas if it falls outside the sphere then the dipeptide is rejected. This process is then repeated for each of the subsequent $C\alpha$ positions, such that the peptide grows from the Pocket 1 $C\alpha$ 'seed', until all nine subsequent $C\alpha$s have been positioned from all possible permutations of the preceding $C\alpha$s. The process is then repeated once more for the single $C\alpha$ preceding pocket 1 to create a library of backbone $C\alpha$ positions located within the binding groove.

The number of backbones generated is dependent upon several factors: The size of the 'spheres of allowed positions'; the fineness of the gridding of the 'primary sphere' at the Pocket 1 position; the fineness of the step-wise rotation of the $\phi$ and $\psi$ angles used to position subsequent $C\alpha$s. Using this process, a large library of backbones can be created. The larger the backbone library, the more likely it will be that the optimum fit will be found for a particular peptide within the binding groove of an MHC Class II molecule. In as much as all backbones will not be suitable for docking with all the models of MHC Class II molecules due to clashes with amino-acids of the binding domains, for each allele a subset of the library is created comprising backbones which can be accommodated by that allele. The use of the backbone library, in conjunction with the models of MHC Class II molecules creates an exhaustive database consisting of allowed side chain conformations for each amino-acid in each position of the binding groove for each MHC Class II molecule docked with each allowed backbone. This data set is generated using a simple steric overlap function where a MHC Class II molecule is docked with a backbone and an amino-acid side chain is grafted onto the backbone at the desired-position. Each of the rotatable bonds of the side chain is rotated step-wise at set intervals and the resultant positions of the atoms dependent upon that bond noted. The interaction of the atom with atoms of side-chains of the binding groove is noted and positions are either accepted or rejected according to the following criteria: The sum total of the overlap of all atoms so far positioned must not exceed a pre-determined value. Thus the stringency of the conformational search is a function of the interval used in the step-wise rotation of the bond and the pre-determined limit for the total overlap. This latter value can be small if it is known that a particular pocket is rigid, however the stringency can be relaxed if the positions of pocket side-chains are known to be relatively flexible. Thus allowances can be made to imitate variations in flexibility within pockets of the binding groove. This conformational search is then repeated for every amino-acid at every position of each backbone when docked with each of the MRC Class II molecules to create the exhaustive database of side-chain conformations.

A suitable mathematical expression is used to estimate the energy of binding between models of MHC Class II molecules in conjunction with peptide ligand conformations which have to be empirically derived by scanning the large database of backbone/side-chain conformations described above. Thus a protein is scanned for potential T-cell epitopes by subjecting each possible peptide of length varying between 9 and 20 amino-acids (although the length is kept constant for each scan) to the following computations: An MHC Class II molecule is selected together with a peptide backbone allowed for that molecule and the side-chains corresponding to the desired peptide sequence are grafted on. Atom identity and interatomic distance data relating to a particular side-chain at a particular position on the backbone are collected for each allowed conformation of that amino-acid (obtained from the database described above). This is repeated for each side-chain along the backbone and peptide scores derived using a scoring function. The best score for that backbone is retained and the process repeated for each allowed backbone for the selected model. The scores from all allowed backbones are compared and the highest score is deemed to be the peptide score for the desired peptide in that MHC Class II model. This process is then repeated for each model with every possible peptide derived from the protein being scanned, and the scores for peptides versus models are displayed.

In the context of the present invention, each ligand presented for the binding affinity calculation is an amino-acid segment selected from a peptide or protein as discussed above. Thus, the ligand is a selected stretch of amino acids about 9 to 20 amino acids in length derived from a peptide, polypeptide or protein of known sequence. The terms "amino acids" and "residues" are hereinafter regarded as equivalent terms. The ligand, in the form of the consecutive amino acids of the peptide to be examined grafted onto a backbone from the backbone library, is positioned in the binding cleft of an MHC Class II molecule from the MHC Class II molecule model library via the coordinates of the C"-α atoms of the peptide backbone and an allowed conformation for each sidechain is selected from the database of allowed conformations. The relevant atom identities and interatomic distances are also retrieved from this database and used to calculate the peptide binding score. Ligands with a high binding affinity for the MHC Class II binding pocket are flagged as candidates for site-directed mutagenesis. Amino-acid substitutions are made in the flagged ligand (and hence in the protein of interest) which is then retested using the scoring function in order to determine changes which reduce the binding affinity below a predetermined threshold value. These changes can then be incorporated into the protein of interest to remove T-cell epitopes.

Binding between the peptide ligand and the binding groove of MHC Class II molecules involves non-covalent interactions including, but not limited to: hydrogen bonds, electrostatic interactions, hydrophobic (lipophilic) interactions and Van der Waal's interactions. These are included in the peptide scoring function as described in detail below. It should be understood that a hydrogen bond is a non-covalent bond which can be formed between polar or charged groups and consists of a hydrogen atom shared by two other atoms. The hydrogen of the hydrogen donor has a positive charge where the hydrogen acceptor has a partial negative charge. For the purposes of peptide/protein interactions, hydrogen bond donors may be either nitrogens with hydrogen attached or hydrogens attached to oxygen or nitrogen. Hydrogen bond acceptor atoms may be oxygens not attached to hydrogen, nitrogens with no hydrogens attached and one or two connections, or sulphurs with only one connection. Certain atoms, such as oxygens attached to hydrogens or imine nitrogens (e.g. C═NH) may be both hydrogen acceptors or donors. Hydrogen bond energies range from 3 to 7 Kcal/mol and are much stronger than Van der Waal's bonds, but weaker than covalent bonds. Hydrogen bonds are also highly directional and are at their strongest when the donor atom, hydrogen atom and acceptor atom are co-linear. Electrostatic bonds are formed between oppositely charged ion pairs and the strength of the interaction is inversely proportional to the square of the distance between the atoms according to Coulomb's law. The optimal distance between ion pairs is about 2.8 Å. In protein/peptide interactions, electrostatic bonds may be formed between arginine, histidine or lysine and aspartate or glutamate. The strength of the bond will depend upon the pKa of the ionizing group and the dielectric constant of the medium although they are approximately similar in strength to hydrogen bonds.

Lipophilic interactions are favorable hydrophobic-hydrophobic contacts that occur between he protein and peptide ligand. Usually, these will occur between hydrophobic amino acid side chains of the peptide buried within the pockets of the binding groove such that they are not exposed to solvent. Exposure of the hydrophobic residues to solvent is highly unfavorable since the surrounding solvent molecules are forced to hydrogen bond with each other forming cage-like clathrate structures. The resultant decrease in entropy is highly unfavorable. Lipophilic atoms may be sulphurs which are neither polar nor hydrogen acceptors and carbon atoms which are not polar.

Van der Waal's bonds are non-specific forces found between atoms which are 3-4 Å apart. They are weaker and less specific than hydrogen and electrostatic bonds. The distribution of electronic charge around an atom changes with time and, at any instant, the charge distribution is not symmetric. This transient asymmetry in electronic charge induces a similar asymmetry in neighboring atoms. The resultant attractive forces between atoms reaches a maximum at the Van der Waal's contact distance but diminishes very rapidly at about 1 Å to about 2 Å. Conversely, as atoms become separated by less than the contact distance, increasingly strong repulsive forces become dominant as the outer electron clouds of the atoms overlap. Although the attractive forces are relatively weak compared to electrostatic and hydrogen bonds (about 0.6 Kcal/mol), the repulsive forces in particular may be very important in determining whether a peptide ligand may bind successfully to a protein.

In one embodiment, the Böhm scoring function (SCORE1 approach) is used to estimate the binding constant. (Böhm, H. J., *J. Comput Aided Mol. Des.,* 8(3):243-256 (1994) which is hereby incorporated in its entirety). In another embodiment, the scoring function (SCORE2 approach) is used to estimate the binding affinities as an indicator of a ligand containing a T-cell epitope (Böhm, H. J., *J. Comput Aided Mol. Des.,* 12(4):309-323 (1998) which is hereby incorporated in its entirety). However, the Böhm scoring functions as described in the above references are used to estimate the binding affinity of a ligand to a protein where it is already known that the ligand successfully binds to the protein and the protein/ligand complex has had its structure solved, the solved structure being present in the Protein Data Bank ("PDB"). Therefore, the scoring function has been developed with the benefit of known positive binding data. In order to allow for discrimination between positive and negative binders, a repulsion term must be added to the equation. In addition, a more satisfactory estimate of binding energy is achieved by computing the lipophilic interactions in a pairwise manner rather than using the area based energy term of the above Böhm functions. Therefore, in a preferred embodiment, the binding energy is estimated using a modified Böhm scoring function. In the modified Böhm scoring function, the binding energy between protein and ligand ($\Delta G_{bind}$) is estimated considering the following parameters: The reduction of binding energy due to the overall loss of translational and rotational entropy of the ligand ($\Delta G_0$); contributions from ideal hydrogen bonds ($\Delta G_{hb}$) where at least one partner is neutral; contributions from unperturbed ionic interactions ($\Delta G_{ionic}$); lipophilic interactions between lipophilic ligand atoms and lipophilic acceptor atoms ($\Delta G_{lipo}$); the loss of binding energy due to the freezing of internal degrees of freedom in the ligand, i.e., the freedom of rotation about each C—C bond is reduced ($\Delta G_{rot}$); the energy of the interaction between the protein and ligand ($E_{VdW}$). Consideration of these terms gives equation 1:

$$(\Delta G_{bind})=(\Delta G_0)+(\Delta G_{hb}\times N_{hb})+(\Delta G_{ionic}\times N_{ionic})+(\Delta G_{lipo}\times N_{lipo})+(\Delta G_{rot}+N_{rot})+(E_{VdW})$$

Where N is the number of qualifying interactions for a specific term and, in one embodiment, $\Delta G_0$, $\Delta G_{hb}$, $\Delta G_{ionic}$, $\Delta G_{lipo}$ and $\Delta G_{rot}$ are constants which are given the values: 5.4, −4.7, −4.7, −0.17, and 1.4, respectively.

The term $N_{hb}$ is calculated according to equation 2:

$$N_{hb}=\Sigma_{h\text{-}bonds} f(\Delta R,\Delta\alpha)\times f(N_{neighb})\times f_{pcs}$$

$f(\Delta R, \Delta\alpha)$ is a penalty function which accounts for large deviations of hydrogen bonds from ideality and is calculated according to equation 3:

$$f(\Delta R,\Delta-\alpha)=f1(\Delta R)\times f2(\Delta\alpha)$$

Where:

f1($\Delta R$)=1 if $\Delta R$<=TOL or =1-($\Delta R$-TOL)/0.4 if $\Delta R$<=0.4+TOL or =0 if $\Delta R$>0.4+TOL And:

f2($\Delta\alpha$)=1 if $\Delta\alpha$<30° or =1-($\Delta\alpha$-30)/50 if $\Delta\alpha$<=80° or =0 if $\Delta\alpha$>80°

TOL is the tolerated deviation in hydrogen bond length=0.25 Å

$\Delta R$ is the deviation of the H—O/N hydrogen bond length from the ideal value=1.9 Å $\Delta\alpha$ is the deviation of the hydrogen bond angle $\angle_{N/O-H\ldots O/N}$ from its idealized value of 180°

$f(N_{neighb})$ distinguishes between concave and convex parts of a protein surface and therefore assigns greater weight to polar interactions found in pockets rather than those found at the protein surface. This function is calculated according to equation 4 below:

$$f(N_{neighb})=(N_{neighb}/N_{neighb,0})^\alpha \text{ where } \alpha=0.5$$

$N_{neighb}$ is the number of non-hydrogen protein atoms that are closer than 5 Å to any given protein atom.

$N_{neighb,0}$ is a constant=25

$f_{pcs}$ is a function which allows for the polar contact surface area per hydrogen bond and therefore distinguishes between strong and weak hydrogen bonds and its value is determined according to the following criteria:

$$f_{pcs}=\beta \text{ when } A_{polar}/N_{HB}<10 \text{ Å}^2$$

$$\text{or } f_{pcs}=1 \text{ when } A_{polar}/N_{HB}>10 \text{ Å}^2$$

$A_{polar}$ is the size of the polar protein-ligand contact surface $N_{HB}$ is the number of hydrogen bonds $\beta$ is a constant whose value=1.2

For the implementation of the modified Böhm scoring function, the contributions from ionic interactions, $\Delta G_{ionic}$, are computed in a similar fashion to those from hydrogen bonds described above since the same geometry dependency is assumed.

The term $N_{lipo}$ is calculated according to equation 5 below:

$$N_{lipo}=\Sigma_{1L}f(r_{1L})$$

$f(r_{1L})$ is calculated for all lipophilic ligand atoms, 1, and all lipophilic protein atoms, L, according to the following criteria:

$$f(r_{1L})=1 \text{ when } r_{1L}<=R1 f(r_{1L})=(r_{1L}-R1)/(R2-R1) \text{ when } R2<r_{1L}>R1$$

$$f(r_{1L})=0 \text{ when } r_{1L}>=R2$$

Where: $R1=r_1^{vdw}+r_L^{vdw}+0.5$ and $R2=R1+3.0$ and $r_1^{vdw}$ is the Van der Waal's radius of atom 1 and $r_L^{vdw}$ is the Van der Waal's radius of atom L

The term $N_{rot}$ is the number of rotable bonds of the amino acid side chain and is taken to be the number of acyclic sp$^3$-sp$^3$ and sp$^3$-sp$^2$ bonds. Rotations of terminal —CH$_3$ or —NH$_3$ are not taken into account.

The final term, $E_{VdW}$, is calculated according to equation 6 below:

$$E_{VdW}=\in_1\in_2((r_1^{vdw}+r_2^{vdw})^{12}/r^{12}-(r_1^{vdw}+r_2^{vdw})^6/r^6),$$
where:

$\in_1$ and $\in_2$ are constants dependent upon atom identity $r_1^{vdw}+r_2^{vdw}$ are the Van der Waal's atomic radii r is the distance between a pair of atoms.

With regard to Equation 6, in one embodiment, the constants $\in_1$ and $\in_2$ are given the atom values: C: 0.245, N: 0.283, O: 0.316, S: 0.316, respectively (i.e. for atoms of Carbon, Nitrogen, Oxygen and Sulphur, respectively). With regards to equations 5 and 6, the Van der Waal's radii are given the atom values C: 1.85, N: 1.75, O: 1.60, S: 2.00 Å.

It should be understood that all predetermined values and constants given in the equations above are determined within the constraints of current understandings of protein ligand interactions with particular regard to the type of computation being undertaken herein. Therefore, it is possible that, as this scoring function is refined further, these values and constants may change hence any suitable numerical value which gives the desired results in terms of estimating the binding energy of a protein to a ligand may be used and hence fall within the scope of the present invention.

As described above, the scoring function is applied to data extracted from the database of side-chain conformations, atom identities, and interatomic distances. For the purposes of the present description, the number of MHC Class II molecules included in this database is 42 models plus four solved structures. It should be apparent from the above descriptions that the modular nature of the construction of the computational method of the present invention means that new models can simply be added and scanned with the peptide backbone library and side-chain conformational search function to create additional data sets which can be processed by the peptide scoring function as described above. This allows for the repertoire of scanned MHC Class II molecules to easily be increased, or structures and associated data to be replaced if data are available to create more accurate models of the existing alleles.

The present prediction method can be calibrated against a data set comprising a large number of peptides whose affinity for various MHC Class II molecules has previously been experimentally determined. By comparison of calculated versus experimental data, a cut of value can be determined above which it is known that all experimentally determined T-cell epitopes are correctly predicted.

It should be understood that, although the above scoring function is relatively simple compared to some sophisticated methodologies that are available, the calculations are performed extremely rapidly. It should also be understood that the objective is not to calculate the true binding energy per se for each peptide docked in the binding groove of a selected MHC Class II protein. The underlying objective is to obtain comparative binding energy data as an aid to predicting the location of T-cell epitopes based on the primary structure (i.e. amino acid sequence) of a selected protein. A relatively high binding energy or a binding energy above a selected threshold value would suggest the presence of a T-cell epitope in the ligand. The ligand may then be subjected to at least one round of amino-acid substitution and the binding energy recalculated. Due to the rapid nature of the calculations, these manipulations of the peptide sequence can be performed interactively within the program's user interface on cost-effectively available computer hardware. Major investment in computer hardware is thus not required.

It would be apparent to one skilled in the art that other available software could be used for the same purposes. In particular, more sophisticated software which is capable of docking ligands into protein binding-sites may be used in conjunction with energy minimization. Examples of docking software are: DOCK (Kuntz et al., *J. Mol. Biol.*, 161:269-288 (1982)), LUDI (Böhm, H. J., *J. Comput Aided Mol. Des.*, 8:623-632 (1994)) and FLEXX (Rarey M., et al., ISMB, 3:300-308 (1995)). Examples of molecular modeling and manipulation software include: AMBER (Tripos) and CHARMm (Molecular Simulations Inc.). The use of these computational methods would severely limit the throughput of the method of this invention due to the lengths of processing time required to make the necessary calculations. However, it is feasible that such methods could be used as a 'secondary screen' to obtain more accurate calculations of binding energy for peptides which are found to be 'positive binders' via the method of the present invention. The limitation of processing time for sophisticated molecular mechanic or molecular dynamic calculations is one which is defined both by the design of the software which makes these calculations and the current technology limitations of computer hardware. It may be anticipated that, in the future, with the writing of more efficient code and the continuing increases in speed of computer processors, it may become feasible to make such calculations within a more manageable timeframe. Further information on energy functions applied to macromolecules and consideration of the various interactions that take place within a folded protein structure can be found in: Brooks, B. R., et al., *J. Comput. Chem.*, 4:187-217 (1983) and further information concerning general protein-ligand interactions can be found in: Dauber-Osguthorpe et al., *Proteins* 4(1):31-47(1988), which are incorporated herein by reference in their entirety. Useful background information can also be found, for example, in Fasman, G. D., ed., *Prediction of Protein Structure and the Principles of protein Conformation*, Plenum Press, New York, ISBN: 0-306 4313-9.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

INCORPORATION BY REFERENCE

All patents, patent applications, and scientific publications mentioned herein above are incorporated by reference into this application in their entirety.

What is claimed is:

1. A fusion protein with reduced immunogenicity comprising:
    a non-immunoglobulin protein and
    an immunoglobulin protein fused to said non-immunoglobulin protein via a fusion junction,
    wherein the amino acid sequence of a junction region surrounding the fusion junction is modified by substitution or deletion of one or more amino acids to remove a non-self T-cell epitope,
    wherein the junction region comprises an IgG region wherein the LSLS amino acid sequence (amino acids 3-6 of SEQ ID NO:5) is mutated.

2. The fusion protein of claim 1, wherein a C-terminus of the immunoglobulin protein is fused to the N-terminus of the non-immunoglobulin protein.

3. The fusion protein of claim 1, wherein the junction region comprises an IgG sequence having an ATAT amino acid sequence (amino acids 3-6 of SEQ ID NO:6) instead of an LSLS amino acid sequence (amino acids 3-6 of SEQ ID NO:5).

4. The fusion protein of claim 1, wherein the junction region comprises an IgG region wherein the LSLS amino acid sequence (amino acids 3-6 of SEQ ID NO:5) is mutated without generating a T-cell epitope.

5. The fusion protein of claim 1 wherein the immunoglobulin moiety comprises two immunoglobulin isotypes.

6. The fusion protein of claim 1, wherein the mutation comprises a substitution of a leucine to a threonine, alanine or proline.

7. The fusion protein of claim 1, wherein the mutation comprises an amino acid substitution to glycine or proline.

* * * * *

UNITED STATES PATENT AND TRADEMARK OFFICE
CERTIFICATE OF CORRECTION

PATENT NO. : 7,601,814 B2
APPLICATION NO. : 11/233683
DATED : October 13, 2009
INVENTOR(S) : Gillies et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 618 days.

Signed and Sealed this

Fifth Day of October, 2010

David J. Kappos
*Director of the United States Patent and Trademark Office*

SEQUENCE LISTING

```
<160> NUMBER OF SEQ ID NOS: 59

<210> SEQ ID NO 1
<211> LENGTH: 330
<212> TYPE: PRT
<213> ORGANISM: Homo sapiens
<220> FEATURE:
<221> NAME/KEY: misc_feature
<223> OTHER INFORMATION: human Ig gamma heavy chain C region

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
```

```
                        180                 185                 190
His Gln Asp Trp Leu Asn Gly Lys Glu Tyr Lys Cys Lys Val Ser Asn
                195                 200                 205
Lys Ala Leu Pro Ala Pro Ile Glu Lys Thr Ile Ser Lys Ala Lys Gly
            210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 2
<211> LENGTH: 326
<212> TYPE: PRT
<213> ORGANISM: Homo sapiens
<220> FEATURE:
<221> NAME/KEY: misc_feature
<223> OTHER INFORMATION: human Ig gamma-2 chain C region

<400> SEQUENCE: 2

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
            100                 105                 110
Pro Val Ala Gly Pro Ser Val Phe Leu Phe Pro Pro Lys Pro Lys Asp
        115                 120                 125
Thr Leu Met Ile Ser Arg Thr Pro Glu Val Thr Cys Val Val Val Asp
    130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
        195                 200                 205
```

```
Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 3
<211> LENGTH: 362
<212> TYPE: PRT
<213> ORGANISM: Homo sapiens
<220> FEATURE:
<221> NAME/KEY: misc_feature
<223> OTHER INFORMATION: human Ig3 constant region

<400> SEQUENCE: 3

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Ala Pro Glu Leu Leu Gly Gly Pro Ser Val Phe Leu Phe Pro Pro
145                 150                 155                 160

Lys Pro Lys Asp Thr Leu Met Ile Ser Arg Thr Pro Glu Val Thr Cys
                165                 170                 175

Val Val Val Asp Val Ser His Glu Asp Pro Glu Val Gln Phe Lys Trp
            180                 185                 190

Tyr Val Asp Gly Val Glu Val His Asn Ala Lys Thr Lys Pro Trp Glu
        195                 200                 205

Glu Gln Tyr Asn Ser Thr Phe Arg Val Val Ser Val Leu Thr Val Leu
    210                 215                 220

His Gln Asp Trp Leu Asn Gly Lys Glu Tyr Lys Cys Lys Val Ser Asn
225                 230                 235                 240
```

```
Lys Ala Leu Pro Ala Pro Ile Glu Lys Thr Ile Ser Lys Thr Lys Gly
            245                 250                 255

Gln Pro Arg Glu Pro Gln Val Tyr Thr Leu Pro Pro Ser Arg Glu Glu
            260                 265                 270

Met Thr Lys Asn Gln Val Ser Leu Thr Cys Leu Val Lys Gly Phe Tyr
            275                 280                 285

Pro Ser Asp Ile Ala Met Glu Trp Glu Ser Ser Gly Gln Pro Glu Asn
            290                 295                 300

Asn Tyr Lys Thr Thr Pro Pro Val Leu Asp Ser Asp Gly Ser Phe Phe
305                 310                 315                 320

Leu Tyr Ser Lys Leu Thr Val Asp Lys Ser Arg Trp Gln Gln Gly Asn
            325                 330                 335

Ile Phe Ser Cys Ser Val Met His Glu Ala Leu His Asn His Tyr Thr
            340                 345                 350

Gln Lys Ser Leu Ser Leu Ser Pro Gly Lys
            355                 360

<210> SEQ ID NO 4
<211> LENGTH: 327
<212> TYPE: PRT
<213> ORGANISM: Homo sapiens
<220> FEATURE:
<221> NAME/KEY: misc_feature
<223> OTHER INFORMATION: Ig gamma-4 chain C region

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
```

```
                    225                 230                 235                 240
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 5
<211> LENGTH: 9
<212> TYPE: PRT
<213> ORGANISM: Artificial sequence
<220> FEATURE:
<223> OTHER INFORMATION: potential T cell epitope

<400> SEQUENCE: 5

Lys Ser Leu Ser Leu Ser Pro Gly Lys
1               5

<210> SEQ ID NO 6
<211> LENGTH: 9
<212> TYPE: PRT
<213> ORGANISM: Artificial sequence
<220> FEATURE:
<223> OTHER INFORMATION: mutated potential T cell epitope

<400> SEQUENCE: 6

Lys Ser Ala Thr Ala Thr Pro Gly Lys
1               5

<210> SEQ ID NO 7
<211> LENGTH: 9
<212> TYPE: PRT
<213> ORGANISM: Artificial sequence
<220> FEATURE:
<223> OTHER INFORMATION: mutated potential T cell epitope

<400> SEQUENCE: 7

Lys Ser Ala Thr Ala Thr Pro Gly Ala
1               5

<210> SEQ ID NO 8
<211> LENGTH: 13
<212> TYPE: PRT
<213> ORGANISM: Artificial sequence
<220> FEATURE:
<223> OTHER INFORMATION: sequence near the C-terminus of CH3 domain of
      the IgA Fc region

<400> SEQUENCE: 8

Gln Lys Thr Ile Asp Arg Leu Ala Gly Lys Pro Thr His
1               5                   10

<210> SEQ ID NO 9
<211> LENGTH: 13
<212> TYPE: PRT
<213> ORGANISM: Artificial sequence
<220> FEATURE:
```

```
<223> OTHER INFORMATION: mutated sequence near the C-terminus of CH3
      domain of the IgA Fc region

<400> SEQUENCE: 9

Gln Lys Thr Ala Asp Arg Thr Ala Gly Lys Pro Thr His
1               5                   10

<210> SEQ ID NO 10
<211> LENGTH: 13
<212> TYPE: PRT
<213> ORGANISM: Artificial sequence
<220> FEATURE:
<223> OTHER INFORMATION: deimmunized sequence in an IgA-X fusion

<400> SEQUENCE: 10

Gln Lys Thr Pro Thr Arg Thr Ala Gly Lys Pro Thr His
1               5                   10

<210> SEQ ID NO 11
<211> LENGTH: 13
<212> TYPE: PRT
<213> ORGANISM: Artificial sequence
<220> FEATURE:
<223> OTHER INFORMATION: deimmunized sequence in an IgA-X fusion

<400> SEQUENCE: 11

Gln Lys Thr Pro Thr Arg Pro Ala Gly Lys Pro Thr His
1               5                   10

<210> SEQ ID NO 12
<211> LENGTH: 13
<212> TYPE: PRT
<213> ORGANISM: Artificial sequence
<220> FEATURE:
<223> OTHER INFORMATION: deimmunized sequence in an IgA-X fusion

<400> SEQUENCE: 12

Gln Lys Thr Ala Thr Arg Pro Ala Gly Lys Pro Thr His
1               5                   10

<210> SEQ ID NO 13
<211> LENGTH: 13
<212> TYPE: PRT
<213> ORGANISM: Artificial sequence
<220> FEATURE:
<223> OTHER INFORMATION: potential T cell epitope in the HSA-IFNalpha
      junction

<400> SEQUENCE: 13

Lys Lys Leu Val Ala Ala Ser Gln Ala Ala Leu Gly Leu
1               5                   10

<210> SEQ ID NO 14
<211> LENGTH: 13
<212> TYPE: PRT
<213> ORGANISM: Artificial sequence
<220> FEATURE:
<223> OTHER INFORMATION: modified C-terminus of albumin

<400> SEQUENCE: 14

Lys Lys Leu Val Ala Ala Ser Gln Ala Ala Thr Thr Ala
1               5                   10

<210> SEQ ID NO 15
<211> LENGTH: 30
<212> TYPE: PRT
<213> ORGANISM: Artificial sequence
```

```
<220> FEATURE:
<223> OTHER INFORMATION: sequence in an Fc fusion protein

<400> SEQUENCE: 15

His Asn His Tyr Thr Gln Lys Ser Leu Ser Leu Ser Pro Gly Lys Gly
1               5                   10                  15

Gly Gly Gly Ser Gly Gly Gly Ser Gly Gly Gly Ser
            20                  25                  30

<210> SEQ ID NO 16
<211> LENGTH: 30
<212> TYPE: PRT
<213> ORGANISM: Artificial sequence
<220> FEATURE:
<223> OTHER INFORMATION: modified sequence in an Fc fusion protein

<400> SEQUENCE: 16

His Asn His Tyr Thr Gln Lys Ser Ala Thr Ala Thr Pro Gly Lys Gly
1               5                   10                  15

Gly Gly Gly Ser Gly Gly Gly Ser Gly Gly Gly Ser
            20                  25                  30

<210> SEQ ID NO 17
<211> LENGTH: 9
<212> TYPE: PRT
<213> ORGANISM: Artificial sequence
<220> FEATURE:
<223> OTHER INFORMATION: junction sequence

<400> SEQUENCE: 17

Leu Ser Leu Ser Pro Gly Lys Ala Pro
1               5

<210> SEQ ID NO 18
<211> LENGTH: 9
<212> TYPE: PRT
<213> ORGANISM: Artificial sequence
<220> FEATURE:
<223> OTHER INFORMATION: modified junction sequence

<400> SEQUENCE: 18

Ala Thr Ala Thr Pro Gly Ala Ala Pro
1               5

<210> SEQ ID NO 19
<211> LENGTH: 9
<212> TYPE: PRT
<213> ORGANISM: Artificial sequence
<220> FEATURE:
<223> OTHER INFORMATION: modified junction sequence

<400> SEQUENCE: 19

Leu Asn Leu Ser Pro Gly Ala Ala Pro
1               5

<210> SEQ ID NO 20
<211> LENGTH: 13
<212> TYPE: PRT
<213> ORGANISM: Artificial sequence
<220> FEATURE:
<223> OTHER INFORMATION: synthetic peptide containing a reactive epitope

<400> SEQUENCE: 20

Lys Ser Leu Ser Leu Ser Pro Gly Lys Ala Pro Thr Ser
1               5                   10
```

<210> SEQ ID NO 21
<211> LENGTH: 13
<212> TYPE: PRT
<213> ORGANISM: Artificial sequence
<220> FEATURE:
<223> OTHER INFORMATION: modified synthetic peptide containing a
      reactive epitope

<400> SEQUENCE: 21

Lys Ser Ala Thr Ala Thr Pro Gly Lys Ala Pro Thr Ser
1               5                   10

<210> SEQ ID NO 22
<211> LENGTH: 39
<212> TYPE: PRT
<213> ORGANISM: Artificial sequence
<220> FEATURE:
<223> OTHER INFORMATION: albumin-CD4 junction sequence

<400> SEQUENCE: 22

Thr Cys Phe Ala Glu Glu Gly Lys Lys Leu Val Ala Ala Ser Gln Ala
1               5                   10                  15

Ala Leu Gly Leu Lys Lys Val Val Leu Gly Lys Lys Gly Asp Thr Val
            20                  25                  30

Glu Leu Thr Cys Thr Ala Ser
        35

<210> SEQ ID NO 23
<211> LENGTH: 13
<212> TYPE: PRT
<213> ORGANISM: Artificial sequence
<220> FEATURE:
<223> OTHER INFORMATION: potential T cell epitope in HSA-IFNalpha fusion

<400> SEQUENCE: 23

Lys Leu Val Ala Ala Ser Gln Ala Ala Leu Gly Leu Cys
1 5 10

<210> SEQ ID NO 24
<211> LENGTH: 13
<212> TYPE: PRT
<213> ORGANISM: Artificial sequence
<220> FEATURE:
<223> OTHER INFORMATION: potential T cell epitope in HSA-IFNalpha fusion

<400> SEQUENCE: 24

Leu Gly Leu Cys Asp Leu Pro Gln Thr His Ser Leu Gly
1 5 10

<210> SEQ ID NO 25
<211> LENGTH: 5
<212> TYPE: PRT
<213> ORGANISM: Artificial sequence
<220> FEATURE:
<223> OTHER INFORMATION: C-terminus albumin sequence

<400> SEQUENCE: 25

Ala Ala Leu Gly Leu
1 5

<210> SEQ ID NO 26
<211> LENGTH: 5
<212> TYPE: PRT
<213> ORGANISM: Artificial sequence
<220> FEATURE:
<223> OTHER INFORMATION: mutated C-terminus albumin sequence

```
<400> SEQUENCE: 26

Thr Ala Thr Thr Ala
1               5

<210> SEQ ID NO 27
<211> LENGTH: 19
<212> TYPE: PRT
<213> ORGANISM: Artificial sequence
<220> FEATURE:
<223> OTHER INFORMATION: modified albumin junction region

<400> SEQUENCE: 27

Cys Phe Ala Glu Glu Gly Lys Lys Leu Val Ala Ala Ser Gln Thr Ala
1               5                   10                  15

Thr Thr Ala

<210> SEQ ID NO 28
<211> LENGTH: 21
<212> TYPE: PRT
<213> ORGANISM: Artificial sequence
<220> FEATURE:
<223> OTHER INFORMATION: non-mutant Fc sequence

<400> SEQUENCE: 28

Glu Pro Lys Ser Cys Asp Lys Thr His Thr Cys Pro Pro Cys Pro Ala
1               5                   10                  15

Pro Glu Leu Leu Gly
            20

<210> SEQ ID NO 29
<211> LENGTH: 52
<212> TYPE: PRT
<213> ORGANISM: Artificial sequence
<220> FEATURE:
<223> OTHER INFORMATION: GLP-1-mutant Fc fusion junction

<400> SEQUENCE: 29

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Glu
            20                  25                  30

Pro Lys Ser Ser Asp Lys Thr His Thr Cys Pro Pro Cys Pro Ala Pro
        35                  40                  45

Glu Leu Leu Gly
    50

<210> SEQ ID NO 30
<211> LENGTH: 41
<212> TYPE: PRT
<213> ORGANISM: Artificial sequence
<220> FEATURE:
<223> OTHER INFORMATION: GLP-1-normal Fc fusion junction

<400> SEQUENCE: 30

Ser Tyr Leu Glu Gly Gln Ala Ala Lys Glu Phe Ile Ala Trp Leu Val
1               5                   10                  15

Lys Gly Arg Gly Glu Pro Lys Ser Cys Asp Lys Thr His Thr Cys Pro
            20                  25                  30

Pro Cys Pro Ala Pro Glu Leu Leu Gly
        35                  40
```

```
<210> SEQ ID NO 31
<211> LENGTH: 13
<212> TYPE: PRT
<213> ORGANISM: Artificial sequence
<220> FEATURE:
<223> OTHER INFORMATION: potential T cell epitope at the GLP-1-Fc fusion

<400> SEQUENCE: 31

Lys Glu Phe Ile Ala Trp Leu Val Lys Gly Arg Gly Glu
1               5                   10

<210> SEQ ID NO 32
<211> LENGTH: 13
<212> TYPE: PRT
<213> ORGANISM: Artificial sequence
<220> FEATURE:
<223> OTHER INFORMATION: potential T cell epitope at the GLP-1-Fc fusion
      junction

<400> SEQUENCE: 32

Glu Phe Ile Ala Trp Leu Val Lys Gly Arg Gly Glu Pro
1               5                   10

<210> SEQ ID NO 33
<211> LENGTH: 13
<212> TYPE: PRT
<213> ORGANISM: Artificial sequence
<220> FEATURE:
<223> OTHER INFORMATION: potential T cell epitope in GLP-1-Fc fusion
      junction

<400> SEQUENCE: 33

Ala Trp Leu Val Lys Gly Arg Gly Glu Pro Lys Ser Ser
1               5                   10

<210> SEQ ID NO 34
<211> LENGTH: 52
<212> TYPE: PRT
<213> ORGANISM: Artificial sequence
<220> FEATURE:
<223> OTHER INFORMATION: deimmunized GLP-1Fc fusion junction

<400> SEQUENCE: 34

His Ala Glu Gly Thr Phe Thr Ser Asp Val Ser Ser Tyr Leu Glu Gly
1               5                   10                  15

Gln Ala Ala Lys Glu Phe Ala Ala Trp Ala Val Thr Gly Thr Gly Glu
            20                  25                  30

Pro Lys Ser Ser Asp Lys Thr His Thr Cys Pro Pro Cys Pro Ala Pro
        35                  40                  45

Glu Leu Leu Gly
    50

<210> SEQ ID NO 35
<211> LENGTH: 41
<212> TYPE: PRT
<213> ORGANISM: Artificial sequence
<220> FEATURE:
<223> OTHER INFORMATION: GLP-1-Fc fusion junction with a glycosylation
      site

<400> SEQUENCE: 35

Ser Tyr Leu Glu Gly Gln Ala Ala Lys Glu Phe Ile Ala Trp Leu Val
1               5                   10                  15

Lys Gly Arg Asn Gly Ser Lys Ser Ser Asp Lys Thr His Thr Cys Pro
            20                  25                  30
```

```
Pro Cys Pro Ala Pro Glu Leu Leu Gly
        35                  40

<210> SEQ ID NO 36
<211> LENGTH: 41
<212> TYPE: PRT
<213> ORGANISM: Artificial sequence
<220> FEATURE:
<223> OTHER INFORMATION: TNF-R-gamma-1 fusion junction

<400> SEQUENCE: 36

Ser Thr Ser Phe Leu Leu Pro Met Gly Pro Ser Pro Ala Glu Gly
1               5                   10                  15

Ser Thr Gly Asp Glu Pro Lys Ser Cys Asp Lys Thr His Thr Cys Pro
            20                  25                  30

Pro Cys Pro Ala Pro Glu Leu Leu Gly
        35                  40

<210> SEQ ID NO 37
<211> LENGTH: 41
<212> TYPE: PRT
<213> ORGANISM: Artificial sequence
<220> FEATURE:
<223> OTHER INFORMATION: TNF-R-Fc fusion junction

<400> SEQUENCE: 37

Ser Thr Ser Phe Leu Leu Pro Met Gly Pro Ser Pro Ala Glu Gly
1               5                   10                  15

Ser Thr Gly Asn Gly Ser Lys Ser Cys Asp Lys Thr His Thr Cys Pro
            20                  25                  30

Pro Cys Pro Ala Pro Glu Leu Leu Gly
        35                  40

<210> SEQ ID NO 38
<211> LENGTH: 40
<212> TYPE: PRT
<213> ORGANISM: Artificial sequence
<220> FEATURE:
<223> OTHER INFORMATION: Fc-IL12p35 fusion junction

<400> SEQUENCE: 38

Met His Glu Ala Leu His Asn His Tyr Thr Gln Lys Ser Leu Ser Leu
1               5                   10                  15

Ser Pro Gly Lys Arg Asn Leu Pro Val Ala Thr Pro Asp Pro Gly Met
            20                  25                  30

Phe Pro Cys Leu His His Ser Gln
        35                  40

<210> SEQ ID NO 39
<211> LENGTH: 40
<212> TYPE: PRT
<213> ORGANISM: Artificial sequence
<220> FEATURE:
<223> OTHER INFORMATION: IL-12p40-IL2 fusion junction

<400> SEQUENCE: 39

Arg Ala Gln Asp Arg Tyr Tyr Ser Ser Ser Trp Ser Glu Trp Ala Ser
1               5                   10                  15

Val Pro Cys Ser Ala Pro Thr Ser Ser Ser Thr Lys Lys Thr Gln Leu
            20                  25                  30

Gln Leu Glu His Leu Leu Leu Asp
        35                  40
```

<210> SEQ ID NO 40
<211> LENGTH: 40
<212> TYPE: PRT
<213> ORGANISM: Artificial sequence
<220> FEATURE:
<223> OTHER INFORMATION: modified Fc-IL12p35 fusion junction

<400> SEQUENCE: 40

Met His Glu Ala Leu His Asn His Tyr Thr Gln Lys Ser Ala Thr Ala
1               5                   10                  15

Thr Pro Gly Lys Arg Asn Leu Pro Val Ala Thr Pro Asp Pro Gly Met
            20                  25                  30

Phe Pro Cys Leu His His Ser Gln
        35                  40

<210> SEQ ID NO 41
<211> LENGTH: 40
<212> TYPE: PRT
<213> ORGANISM: Artificial sequence
<220> FEATURE:
<223> OTHER INFORMATION: modified IL12p40-IL2 fusion junction

<400> SEQUENCE: 41

Arg Ala Gln Asp Arg Tyr Tyr Ser Ser Ser Trp Ser Glu Trp Ala Ser
1               5                   10                  15

Val Pro Cys Ser Asn Gly Thr Ser Ser Ser Thr Lys Lys Thr Gln Leu
            20                  25                  30

Gln Leu Glu His Leu Leu Leu Asp
        35                  40

<210> SEQ ID NO 42
<211> LENGTH: 13
<212> TYPE: PRT
<213> ORGANISM: Artificial sequence
<220> FEATURE:
<223> OTHER INFORMATION: potential T cell epitope in IL12p40-IL fusion

<400> SEQUENCE: 42

Ser Glu Trp Ala Ser Val Pro Cys Ser Asn Gly Thr Ser
1               5                   10

<210> SEQ ID NO 43
<211> LENGTH: 13
<212> TYPE: PRT
<213> ORGANISM: Artificial sequence
<220> FEATURE:
<223> OTHER INFORMATION: potential T cell epitope in IL12p40-IL2 fusion
      junction

<400> SEQUENCE: 43

Ala Ser Val Pro Cys Ser Asn Gly Thr Ser Ser Ser Thr
1               5                   10

<210> SEQ ID NO 44
<211> LENGTH: 41
<212> TYPE: PRT
<213> ORGANISM: Artificial sequence
<220> FEATURE:
<223> OTHER INFORMATION: IL4-Fc fusion junction

<400> SEQUENCE: 44

Glu Asn Phe Leu Glu Arg Leu Lys Thr Ile Met Arg Glu Lys Tyr Ser
1               5                   10                  15

Lys Cys Ser Ser Glu Pro Lys Ser Cys Asp Lys Thr His Thr Cys Pro

-continued

```
            20                  25                  30

Pro Cys Pro Ala Pro Glu Leu Leu Gly
        35                  40

<210> SEQ ID NO 45
<211> LENGTH: 40
<212> TYPE: PRT
<213> ORGANISM: Artificial sequence
<220> FEATURE:
<223> OTHER INFORMATION: Fc-GMCSF fusion junction

<400> SEQUENCE: 45

Met His Glu Ala Leu His Asn His Tyr Thr Gln Lys Ser Leu Ser Leu
1               5                   10                  15

Ser Pro Gly Lys Pro Ala Arg Ser Pro Ser Pro Ser Thr Gln Pro Trp
            20                  25                  30

Glu His Val Asn Ala Ile Gln Glu
        35                  40

<210> SEQ ID NO 46
<211> LENGTH: 13
<212> TYPE: PRT
<213> ORGANISM: Artificial sequence
<220> FEATURE:
<223> OTHER INFORMATION: potential T-cell epitope at IL4-Fc fusion
      junction

<400> SEQUENCE: 46

Glu Lys Tyr Ser Lys Cys Ser Ser Glu Pro Lys Ser Cys
1               5                   10

<210> SEQ ID NO 47
<211> LENGTH: 41
<212> TYPE: PRT
<213> ORGANISM: Artificial sequence
<220> FEATURE:
<223> OTHER INFORMATION: modified IL4-Fc fusion

<400> SEQUENCE: 47

Glu Asn Phe Leu Glu Arg Leu Lys Thr Ile Met Arg Glu Lys Tyr Ser
1               5                   10                  15

Lys Cys Ser Ser Thr Pro Lys Ser Cys Asp Lys Thr His Thr Cys Pro
            20                  25                  30

Pro Cys Pro Ala Pro Glu Leu Leu Gly
        35                  40

<210> SEQ ID NO 48
<211> LENGTH: 40
<212> TYPE: PRT
<213> ORGANISM: Artificial sequence
<220> FEATURE:
<223> OTHER INFORMATION: deimmunized Fc-GMCSF fusion junction

<400> SEQUENCE: 48

Met His Glu Ala Leu His Asn His Tyr Thr Gln Lys Ser Ala Thr Ala
1               5                   10                  15

Thr Pro Gly Lys Pro Ala Arg Ser Pro Ser Pro Ser Thr Gln Pro Trp
            20                  25                  30

Glu His Val Asn Ala Ile Gln Glu
        35                  40

<210> SEQ ID NO 49
<211> LENGTH: 35
```

```
<212> TYPE: PRT
<213> ORGANISM: Artificial sequence
<220> FEATURE:
<223> OTHER INFORMATION: IgG2CH1-IgG1hinge fusion junction

<400> SEQUENCE: 49

Gln Thr Tyr Thr Cys Asn Val Asp His Lys Pro Ser Asn Thr Lys Val
1               5                   10                  15

Asp Lys Thr Val Glu Pro Lys Ser Cys Asp Lys Thr His Thr Cys Pro
            20                  25                  30

Pro Cys Pro
        35

<210> SEQ ID NO 50
<211> LENGTH: 35
<212> TYPE: PRT
<213> ORGANISM: Artificial sequence
<220> FEATURE:
<223> OTHER INFORMATION: IgG1hinge-IgG2CH2 fusion junction

<400> SEQUENCE: 50

Glu Pro Lys Ser Cys Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu
        35

<210> SEQ ID NO 51
<211> LENGTH: 13
<212> TYPE: PRT
<213> ORGANISM: Artificial sequence
<220> FEATURE:
<223> OTHER INFORMATION: potential T cell epitope in the IgG2CH1-IgG1
      hinge fusion junction

<400> SEQUENCE: 51

Thr Lys Val Asp Lys Thr Val Glu Pro Lys Ser Cys Asp
1               5                   10

<210> SEQ ID NO 52
<211> LENGTH: 13
<212> TYPE: PRT
<213> ORGANISM: Artificial sequence
<220> FEATURE:
<223> OTHER INFORMATION: potential T cell epitope in the IgG2CH1-IgG1
      hinge fusion junction

<400> SEQUENCE: 52

Lys Thr Val Glu Pro Lys Ser Cys Asp Lys Thr His Thr
1               5                   10

<210> SEQ ID NO 53
<211> LENGTH: 35
<212> TYPE: PRT
<213> ORGANISM: Artificial sequence
<220> FEATURE:
<223> OTHER INFORMATION: modified IgG2CH1-IgG1hinge fusion junction

<400> SEQUENCE: 53

Gln Thr Tyr Thr Cys Asn Val Asp His Lys Pro Ser Asn Thr Lys Ala
1               5                   10                  15

Asp Lys Thr Ala Glu Pro Lys Ser Cys Asp Lys Thr His Thr Cys Pro
            20                  25                  30
```

Pro Cys Pro
        35

<210> SEQ ID NO 54
<211> LENGTH: 35
<212> TYPE: PRT
<213> ORGANISM: Artificial sequence
<220> FEATURE:
<223> OTHER INFORMATION: modified IgG2CH1-IgG1hinge fusion junction

<400> SEQUENCE: 54

Gln Thr Tyr Thr Cys Asn Val Asp His Lys Pro Ser Asn Thr Lys Val
1               5                   10                  15

Asp Lys Thr Val Glu Pro Lys Ser Ser Asp Lys Thr His Thr Cys Pro
            20                  25                  30

Pro Cys Pro
        35

<210> SEQ ID NO 55
<211> LENGTH: 35
<212> TYPE: PRT
<213> ORGANISM: Artificial sequence
<220> FEATURE:
<223> OTHER INFORMATION: modified IgG1hinge-IgG2CH2 fusion junction

<400> SEQUENCE: 55

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu
        35

<210> SEQ ID NO 56
<211> LENGTH: 166
<212> TYPE: PRT
<213> ORGANISM: Artificial sequence
<220> FEATURE:
<223> OTHER INFORMATION: mutant EPO sequence

<400> SEQUENCE: 56

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu Gly
            20                  25                  30

Pro Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Cys Glu Gly Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala

```
145                 150                 155                 160
Cys Arg Thr Gly Asp Arg
                165

<210> SEQ ID NO 57
<211> LENGTH: 17
<212> TYPE: PRT
<213> ORGANISM: Artificial sequence
<220> FEATURE:
<223> OTHER INFORMATION: CH3-EPO fusion junction

<400> SEQUENCE: 57

Thr Gln Lys Ser Ala Thr Ala Thr Pro Gly Ala Ala Pro Pro Arg Leu
1               5                   10                  15

Ile

<210> SEQ ID NO 58
<211> LENGTH: 8
<212> TYPE: PRT
<213> ORGANISM: Artificial sequence
<220> FEATURE:
<223> OTHER INFORMATION: IgG2 CH3 sequence

<400> SEQUENCE: 58

Lys Ser Leu Ser Leu Ser Pro Gly
1               5

<210> SEQ ID NO 59
<211> LENGTH: 8
<212> TYPE: PRT
<213> ORGANISM: Artificial sequence
<220> FEATURE:
<223> OTHER INFORMATION: modified IgG2CH3 sequence

<400> SEQUENCE: 59

Lys Ser Ala Thr Ala Thr Pro Gly
1               5
```